(12) United States Patent
Bruck et al.

(10) Patent No.: US 6,342,224 B1
(45) Date of Patent: Jan. 29, 2002

(54) RECOMBINANT PAPILLOMAVIRUS VACCINE AND METHOD FOR PRODUCTION AND TREATMENT

(75) Inventors: Claudine Bruck, Rixensart; Teresa Cabezon Silva, Lenkebeek; Anne-Marie Eva Fernande Delisse, Gosselies; Catherine Marie Ghislaine Gerard, Rhode Saint Genese; Angela Lombardo-Bencheikh, Wavre, all of (BE)

(73) Assignee: SmithKline Beecham Biologicals, S.A., Rixensart (BE)

( * ) Notice: Subject to any disclaimer, the term of this patent is extended or adjusted under 35 U.S.C. 154(b) by 0 days.

(21) Appl. No.: 09/485,885

(22) PCT Filed: Aug. 17, 1998

(86) PCT No.: PCT/EP98/05285

§ 371 Date: Feb. 18, 2000

§ 102(e) Date: Feb. 18, 2000

(87) PCT Pub. No.: WO99/10375

PCT Pub. Date: Mar. 4, 1999

(30) Foreign Application Priority Data

Aug. 22, 1997 (GB) .............................................. 9717953

(51) Int. Cl.[7] ........................ A61K 39/00; A61K 39/12; C07H 21/04; C07H 14/00
(52) U.S. Cl. .............................. 424/192.1; 424/185.1; 424/186.1; 424/204.1; 536/23.4; 536/23.72; 530/350; 435/69.3; 435/69.7; 435/325; 435/252.3; 435/320.1
(58) Field of Search ................... 530/350; 536/23.4, 536/23.72; 424/192.1, 204.1, 134.1, 185.1, 186.1; 435/252.3, 69.3, 69.7, 320.1, 325

(56) References Cited

U.S. PATENT DOCUMENTS

| | | | | |
|---|---|---|---|---|
| 5,869,445 | A | * | 2/1999 | Cheever ........................ 514/2 |
| 5,958,750 | A | * | 9/1999 | Au-Young ................... 435/201 |
| 6,224,870 | B1 | * | 5/2001 | Segal ....................... 424/192.1 |

FOREIGN PATENT DOCUMENTS

| | | |
|---|---|---|
| DE | 44 41 197 | 3/1996 |
| EP | 0 386 734 | 9/1990 |
| EP | 0 456 197 | 11/1991 |
| FR | 2 586 428 | 2/1987 |
| WO | WO 92/05248 | 4/1992 |
| WO | WO 93/22338 | 11/1993 |
| WO | WO 96/19496 | * 6/1996 |
| WO | WO-96/26277 | * 8/1996 |
| WO | WO 96/36702 | 11/1996 |

OTHER PUBLICATIONS

Ai–long Sun, et al., "Fusion Expression Of Human Pro–Urokinase With E. Coli Thioredoxin," *Biochemistry and Molecular Biology International,* 46:3 479–486 (1998).

Ullman, et al., "Transforming Proteins of Human Papillomarviruses," *Medical Virology,* 6: 39–55 (1996).

Lavallie, et al. Bio/Technology. 1993. vol. 11. pp. 187–193.*

Janson et al. 1993. Limited diversity of the protein D gene (hdp) among encapsulated and nonencapsulated *Haemophilis influezae* strains. Infection and Immunity. vol. 61. No. 11, pp. 4546–4552.*

Baier et al. 1995. Immunogeneic targeting of recombinant peptide vaccines to human antigen–presenting cells by chimeric anti–HLA–DR and anti–surface immunoglobulin D antibody Fab fragments in vitro. Journal of Virology. vol. 69. No. 4, pp. 2357–2365.*

Patrick. 1994. Biochemical characterization of the human papillomavirus type 16 E7 oncoprotein and its interaction with the retinoblastoma growth suppressor gene product. Diss. Abstr Int[B]. vol. 54. no. 12, p. 6186.*

Stoppler et al. 1996. The serine protease inhibitors TLCK and TPCK react with the Rb–binding core of HPV–18 E7 protein and abolish its Rb–bonding capability. Virology. vol. 217, pp. 542–553.*

* cited by examiner

*Primary Examiner*—Mary E. Mosher
*Assistant Examiner*—Shanon A. Foley
(74) *Attorney, Agent, or Firm*—William R. Majarian; Charles M. Kinzig; William T. King

(57) ABSTRACT

The present invention relates to fusions proteins, comprising a protein or part of a protein that provides T helper epitopes and an antigen from a human-papilloma virus. In particular the invention relates to fusion proteins comprising an E6 or E7 protein from HPV strain 16 or 18 linked to protein D from *Haemophilus influenza* B. The invention also provides vaccine compositions that are useful in the treatment or prophylaxis of human papilloma induced tumours.

43 Claims, 60 Drawing Sheets

Protein D1/3 E7 his

1   MDPSSHSSNM ANTQMKSDKI IIAHRGASGY LPEHTLESKA LAFAQQADYL

51  EQDLAMTKDG RLVVIHDHFL DGLTDVAKKF PHRHRKDGRY YVIDFTLKEI

101 QSLEMTENFE TMAMHGDTPT LHEYMLDLQP ETTDLYCYEQ LNDSSEEEDE

151 IDGPAGQAEP DRAHYNIVTF CCKCDSTLRL CVQSTHVDIR TLEDLLMGTL

201 GIVCPICSQK PTSGHHHHHH *

Figure 1A

Sequence of plasmid expressing fusion protein ProtDthr126-E7-His
tail (E7 from HPV16).

```
1   ATGGATCCAA GCAGCCATTC ATCAAATATG GCGAATACCC AAATGAAATC
51  AGACAAAATC ATTATTGCTC ACCGTGGTGC TAGCGGTTAT TTACCAGAGC
101 ATACGTTAGA ATCTAAAGCA CTTGCGTTTG CACAACAGGC TGATTATTTA
151 GAGCAAGATT TAGCAATGAC TAAGGATGGT CGTTTAGTGG TTATTCACGA
201 TCACTTTTTA GATGGCTTGA CTGATGTTGC GAAAAAATTC CCACATCGTC
251 ATCGTAAAGA TGGCCGTTAC TATGTCATCG ACTTTACCTT AAAAGAAATT
301 CAAAGTTTAG AAATGACAGA AAACTTTGAA ACCATGGCCA TGCATGGAGA
351 TACACCTACA TTGCATGAAT ATATGTTAGA TTTGCAACCA GAGACAACTG
401 ATCTCTACTG TTATGAGCAA TTAAATGACA GCTCAGAGGA GGAGGATGAA
451 ATAGATGGTC CAGCTGGACA AGCAGAACCG GACAGAGCCC ATTACAATAT
501 TGTAACCTTT TGTTGCAAGT GTGACTCTAC GCTTCGGTTG TGCGTACAAA
551 GCACACACGT AGACATTCGT ACTTTGGAAG ACCTGTTAAT GGGCACACTA
601 GGAATTGTGT GCCCCATCTG TTCTCAGAAA CCAACTAGTG CCACCATCA
651 CCATCACCAT TAA
```

Figure 1B

SEQUENCE OF PROT.D1/3 E6 His / HPV 16.

Nucleotidic sequence

ATGGATCCAAGCAGCCATTCATCAAATATGGCGAATACCCAAATGAAATC 50
AGACAAAATCATTATTGCTCACCGTGGTGCTAGCGGTTATTTACCAGAGC 100
ATACGTTAGAATCTAAAGCACTTGCGTTTGCACAACAGGCTGATTATTTA 150
GAGCAAGATTTAGCAATGACTAAGGATGGTCGTTTAGTGGTTATTCACGA 200
TCACTTTTAGATGGCTTGACTGATGTTGCGAAAAAATTCCCACATCGTC 250
ATCGTAAAGATGGCCGTTACTATGTCATCGACTTTACCTTAAAAGAAATT 300
CAAAGTTTAGAAATGACAGAAAACTTTGAAACCATGGCCATGTTTCAGGA 350
CCCACAGGAGCGACCCAGAAAGTTACCACAGTTATGCACAGAGCTGCAAA 400
CAACTATACATGATATAATATTAGAATGTGTGTACTGCAAGCAACAGTTA 450
CTGCGACGTGAGGTATATGACTTTGCTTTTCGGGATTATGCATAGTATA 500
TAGAGATGGGAATCCATATGCTGTATGTGATAAATGTTTAAAGTTTTATT 550
CTAAAATTAGTGAGTATAGACATTATTGTTATAGTTTGTATGGAACAACA 600
TTAGAACAGCAATACAACAAACCGTTGTGTGATTTGTTAATTAGGTGTAT 650
TAACTGTCAAAAGCCACTGTGTCCTGAAGAAAAGCAAAGACATCTGGACA 700
AAAAGCAAAGATTCCATAATATAAGGGGTCGGTGGACCGGTCGATGTATG 750
TCTTGTTGCAGATCATCAAGAACACGTAGAGAAACCCAGCTGACTAGTGG 800
CCACCATCACCATCACCATTAA 822

Figure 3A

Peptidic sequence

MDPSSHSSNMANTQMKSDKIIIAHRGASGYLPEHTLESKALAFAQQADYL 50
EQDLAMTKDGRLVVIHDHFLDGLTDVAKKFPHRHRKDGRYYVIDFTLKEI 100
QSLEMTENFETMAMFQDPQERPRKLPQLCTELQTTIHDIILECVYCKQQL 150
LRREVYDFAFRDLCIVYRDGNPYAVCDKCLKFYSKISEYRHYCYSLYGTT 200
LEQQYNKPLCDLLIRCINCQKPLCPEEKQRHLDKKQRFHNIRGRWTGRCM 250
SCCRSSRTRRETQLTSGHHHHHH. 274

Figure 3B

Construction of plasmid pRIT 14556 (TCA 309)
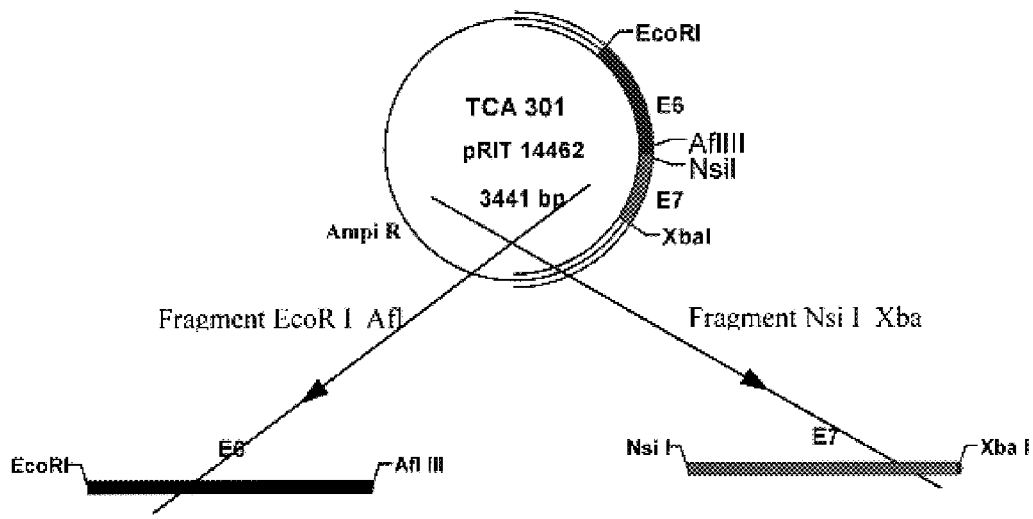
Constitution of a fusion protein between E6 and E7: deletion of 5 nucleotides by insertion of adaptor between Afl III and
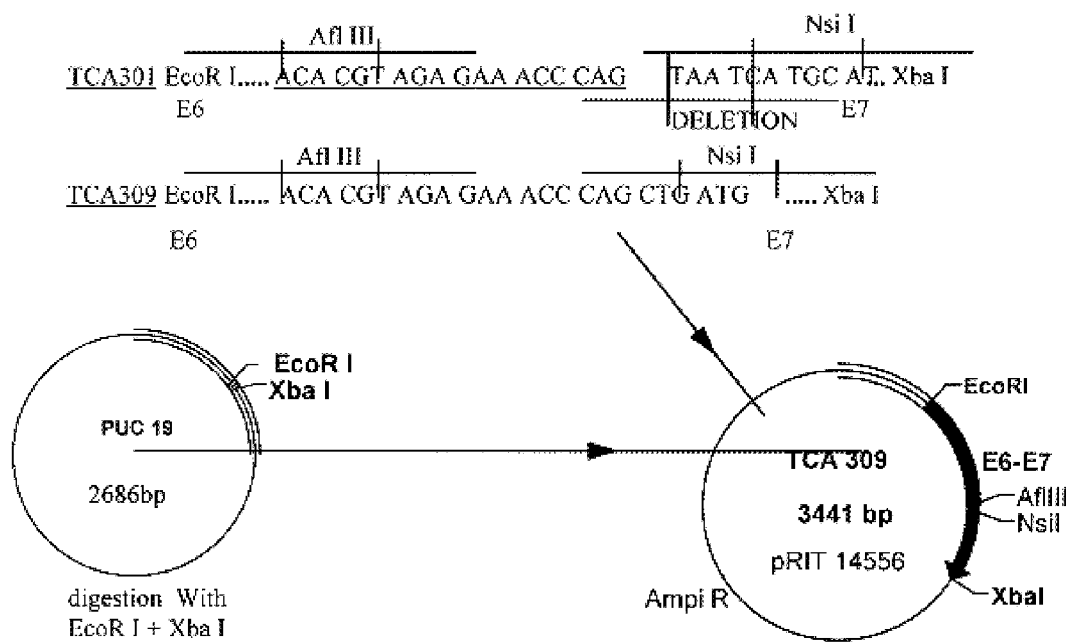
Figure 4

SEQUENCE OF PROT.D1/3 - E6 - E7 - His / HPV 16

Peptidic sequence

ATGGATCCAAGCAGCCATTCATCAAATATGGCGAATACCCAAATGAAATC 50
AGACAAAATCATTATTGCTCACCGTGGTGCTAGCGGTTATTTACCAGAGC 100
ATACGTTAGAATCTAAAGCACTTGCGTTTGCACAACAGGCTGATTATTTA 150
GAGCAAGATTTAGCAATGACTAAGGATGGTCGTTTAGTGGTTATTCACGA 200
TCACTTTTTAGATGGCTTGACTGATGTTGCGAAAAAATTCCCACATCGTC 250
ATCGTAAAGATGGCCGTTACTATGTCATCGACTTTACCTTAAAAGAAATT 300
CAAAGTTTAGAAATGACAGAAAACTTTGAAACCATGGCCATGTTTCAGGA 350
CCCACAGGAGCGACCCAGAAAGTTACCACAGTTATGCACAGAGCTGCAAA 400
CAACTATACATGATATAATATTAGAATGTGTGTACTGCAAGCAACAGTTA 450
CTGCGACGTGAGGTATATGACTTTGCTTTTCGGGATTTATGCATAGTATA 500
TAGAGATGGGAATCCATATGCTGTATGTGATAAATGTTTAAAGTTTTATT 550
CTAAAATTAGTGAGTATAGACATTATTGTTATAGTTTGTATGGAACAACA 600
TTAGAACAGCAATACAACAAACCGTTGTGTGATTTGTTAATTAGGTGTAT 650
TAACTGTCAAAAGCCACTGTGTCCTGAAGAAAAGCAAAGACATCTGGACA 700
AAAAGCAAAGATTCCATAATATAAGGGGTCGGTGGACCGGTCGATGTATG 750
TCTTGTTGCAGATCATCAAGAACACGTAGAGAAACCCAGCTGATGCATGG 800
AGATACACCTACATTGCATGAATATATGTTAGATTTGCAACCAGAGACAA 850
CTGATCTCTACTGTTATGAGCAATTAAATGACAGCTCAGAGGAGGAGGAT 900
GAAATAGATGGTCCAGCTGGACAAGCAGAACCGGACAGAGCCCATTACAA 950
TATTGTAACCTTTTGTTGCAAGTGTGACTCTACGCTTCGGTTGTGCGTAC 1000
AAAGCACACACGTAGACATTCGTACTTTGGAAGACCTGTTAATGGGCACA 1050
CTAGGAATTGTGTGCCCCATCTGTTCTCAGAAACCAACTAGTGGCCACCA 1100
TCACCATCACCATTAA 1116

Figure 6A

Peptidic sequence

MDPSSHSSNMANTQMKSDKIIIAHRGASGYLPEHTLESKALAFAQQADYL 50
EQDLAMTKDGRLVVIHDHFLDGLTDVAKKFPHRHRKDGRYYVIDFTLKEI 100
QSLEMTENFETMAMFQDPQERPRKLPQLCTELQTTIHDIILECVYCKQQL 150
LRREVYDFAFRDLCIVYRDGNPYAVCDKCLKFYSKISEYRHYCYSLYGTT 200
LEQQYNKPLCDLLIRCINCQKPLCPEEKQRHLDKKQRFHNIRGRWTGRCM 250
SCCRSSRTRRETQLMHGDTPTLHEYMLDLQPETTDLYCYEQLNDSSEEED 300
EIDGPAGQAEPDRAHYNIVTFCCKCDSTLRLCVQSTHVDIRTLEDLLMGT 350
LGIVCPICSQKPTSGHHHHHH. 372

Figure 6B

SEQUENCE OF PROT.D1/3 - E7 mutated (cys24 → gly, glu26 → gln) HPV16.

Nucleotidic sequence:

ATGGATCCAAGCAGCCATTCATCAAATATGGCGAATACCCAAATGAAATC 50
AGACAAAATCATTATTGCTCACCGTGGTGCTAGCGGTTATTTACCAGAGC 100
ATACGTTAGAATCTAAAGCACTTGCGTTTGCACAACAGGCTGATTATTTA 150
GAGCAAGATTTAGCAATGACTAAGGATGGTCGTTTAGTGGTTATTCACGA 200
CACTTTTTAGATGGCTTGACTGATGTTGCGAAAAAATTCCCACATCGTC 250
ATCGTAAAGATGGCCGTTACTATGTCATCGACTTTACCTTAAAAGAAATT 300
CAAAGTTTAGAAATGACAGAAAACTTTGAAACCATGGCCATGCATGGAGA 350
TACACCTACATTGCATGAATATATGTTAGATTTGCAACCAGAGACAACTG 400
ATCTCTACGGTTATCAGCAATTAAATGACAGCTCAGAGGAGGAGGATGAA 450
ATAGATGGTCCAGCTGGACAAGCAGAACCGGACAGAGCCCATTACAATAT 500
TGTAACCTTTTGTTGCAAGTGTGACTCTACGCTTCGGTTGTGCGTACAAA 550
GCACACACGTAGACATTCGTACTTTGGAAGACCTGTTAATGGGCACACTA 600
GGAATTGTGTGCCCCATCTGTTCTCAGAAACCAACTAGTGGCCACCATCA 650
CCATCACCATTAA 663

Mutations: T409 → G
G415 → C

Figure 8A

Peptidic sequence:

MDPSSHSSNMANTQMKSDKIIIAHRGASGYLPEHTLESKALAFAQQADYL
EQDLAMTKDGRLVVIHDHFLDGLTDVAKKFPHRHRKDGRYYVIDFTLKEI
QSLEMTENFETMAMHGDTPTLHEYMLDLQPETTDLYGYQQLNDSSEEEDE
IDGPAGQAEPDRAHYNIVTFCCKCDSTLRLCVQSTHVDIRTLEDLLMGTL
GIVCPICSQKPTSGHHHHHH. 221 mutated amino acids: cys24 → gly (=C24→G), glu26 → gln (=E26→Q) of E7 are residues 137 and 139 of the fusion protein.

N term M D P -ProtD1/3(aa4 --> 111)-M A-mutated E7(aa 114 --> 211)-TSGHHHHHH Cterm.

Figure 8B

SEQUENCE OF CLYTA - E6 - His
Nucleotidic sequence

ATGAAAGGGGGAATTGTACATTCAGACGGCTCTTATCCAAAAGACAAGTT 50
TGAGAAAATCAATGGCACTTGGTACTACTTTGACAGTTCAGGCTATATGC 100
TTGCAGACCGCTGGAGGAAGCACACAGACGGCAACTGGTACTGGTTCGAC 150
AACTCAGGCGAAATGGCTACAGGCTGGAAGAAAATCGCTGATAAGTGGTA 200
CTATTTCAACGAAGAAGGTGCCATGAAGACAGGCTGGGTCAAGTACAAGG 250
ACACTTGGTACTACTTAGACGCTAAAGAAGGCGCCATGGTATCAAATGCC 300
TTTATCCAGTCAGCGGACGGAACAGGCTGGTACTACCTCAAACCAGACGG 350
AACACTGGCAGACAGGCCAGAATTGGCCAGCATGCTGGACATGGCCATGT 400
TCAGGACCCACAGGAGCGACCCAGAAAGTTACCACAGTTATGCACAGAG 450
CTGCAAACAACTATACATGATATAATATTAGAATGTGTGTACTGCAAGCA 500
ACAGTTACTGCGACGTGAGGTATATGACTTTGCTTTTCGGGATTTATGCA 550
TAGTATATAGAGATGGGAATCCATATGCTGTATGTGATAAATGTTTAAAG 600
TTTTATTCTAAAATTAGTGAGTATAGACATTATTGTTATAGTTTGTATGG 650
AACAACATTAGAACAGCAATACAACAAACCGTTGTGTGATTTGTTAATTA 700
GGTGTATTAACTGTCAAAAGCCACTGTGTCCTGAAGAAAGCAAAGACAT 750
CTGGACAAAAAGCAAAGATTCCATAATATAAGGGGTCGGTGGACCGGTCG 800
ATGTATGTCTTGTTGCAGATCATCAAGAACACGTAGAGAAACCCAGCTGA 850
CTAGTGGCCACCATCACCATCACCATTAA 879

Figure 10A

Peptidic sequence

MKGGIVHSDGSYPKDKFEKINGTWYYFDSSGYMLADRWRKHTDGNWYWFD 50
NSGEMATGWKKIADKWYYFNEEGAMKTGWVKYKDTWYYLDAKEGAMVSNA 100
FIQSADGTGWYYLKPDGTLADRPELASMLDMAMFQDPQERPRKLPQLCTE 150
LQTTIHDIILECVYCKQQLLRREVYDFAFRDLCIVYRDGNPYAVCDKCLK 200
FYSKISEYRHYCYSLYGTTLEQQYNKPLCDLLIRCINCQKPLCPEEKQRH 250
LDKKQRFHNIRGRWTGRCMSCCRSSRTRRETQLTSGHHHHHH. 293

Figure 10B

SEQUENCE OF CLYTA - E7 - His.

Nucleotidic sequence

ATGAAAGGGGGAATTGTACATTCAGACGGCTCTTATCCAAAAGACAAGTT 50
TGAGAAAATCAATGGCACTTGGTACTACTTTGACAGTTCAGGCTATATGC 100
TTGCAGACCGCTGGAGGAAGCACACAGACGGCAACTGGTACTGGTTCGAC 150
AACTCAGGCGAAATGGCTACAGGCTGGAAGAAAATCGCTGATAAGTGGTA 200
CTATTTCAACGAAGAAGGTGCCATGAAGACAGGCTGGGTCAAGTACAAGG 250
ACACTTGGTACTACTTAGACGCTAAAGAAGGCGCCATGGTATCAAATGCC 300
TTTATCCAGTCAGCGGACGGAACAGGCTGGTACTACCTCAAACCAGACGG 350
AACACTGGCAGACAGGCCAGAATTGGCCAGCATGCTGGACATGGCCATGC 400
ATGGAGATACACCTACATTGCATGAATATATGTTAGATTTGCAACCAGAG 450
ACAACTGATCTCTACTGTTATGAGCAATTAAATGACAGCTCAGAGGAGGA 500
GGATGAAATAGATGGTCCAGCTGGACAAGCAGAACCGGACAGAGCCCATT 550
ACAATATTGTAACCTTTGTTGCAAGTGTGACTCTACGCTTCGGTTGTGC 600
GTACAAAGCACACACGTAGACATTCGTACTTTGGAAGACCTGTTAATGGG 650
CACACTAGGAATTGTGTGCCCCATCTGTTCTCAGAAACCAACTAGTGGCC 700
ACCATCACCATCACCATTAA 720

Figure 12A

Peptidic sequence

MKGGIVHSDGSYPKDKFEKINGTWYYFDSSGYMLADRWRKHTDGNWYWFD 50
NSGEMATGWKKIADKWYYFNEEGAMKTGWVKYKDTWYYLDAKEGAMVSNA 100
FIQSADGTGWYYLKPDGTLADRPELASMLDMAMHGDTPTLHEYMLDLQPE 150
TTDLYCYEQLNDSSEEEDEIDGPAGQAEPDRAHYNIVTFCCKCDSTLRLC 200
VQSTHVDIRTLEDLLMGTLGIVCPICSQKPTSGHHHHHH. 240

Figure 12B

SEQUENCE OF CLYTA - E6E7 - His.

Nucleotidic sequence

ATGAAAGGGGGAATTGTACATTCAGACGGCTCTTATCCAAAAGACAAGTT 50
TGAGAAAATCAATGGCACTTGGTACTACTTTGACAGTTCAGGCTATATGC 100
TTGCAGACCGCTGGAGGAAGCACACAGACGGCAACTGGTACTGGTTCGAC 150
AACTCAGGCGAAATGGCTACAGGCTGGAAGAAAATCGCTGATAAGTGGTA 200
CTATTTCAACGAAGAAGGTGCCATGAAGACAGGCTGGGTCAAGTACAAGG 250
ACACTTGGTACTACTTAGACGCTAAAGAAGGCGCCATGGTATCAAATGCC 300
TTTATCCAGTCAGCGGACGGAACAGGCTGGTACTACCTCAAACCAGACGG 350
AACACTGGCAGACAGGCCAGAATTGGCCAGCATGCTGGACATGGCCATGT 400
TCAGGACCCACAGGAGCGACCCAGAAAGTTACCACAGTTATGCACAGAG 450
CTGCAAACAACTATACATGATATAATATTAGAATGTGTGTACTGCAAGCA 500
ACAGTTACTGCGACGTGAGGTATATGACTTTGCTTTTCGGGATTTATGCA 550
TAGTATATAGAGATGGGAATCCATATGCTGTATGTGATAAATGTTTAAAG 600
TTTTATTCTAAAATTAGTGAGTATAGACATTATTGTTATAGTTTGTATGG 650
AACAACATTAGAACAGCAATACAACAAACCGTTGTGTGATTTGTTAATTA 700
GGTGTATTAACTGTCAAAAGCCACTGTGTCCTGAAGAAAGCAAAGACAT 750
CTGGACAAAAAGCAAAGATTCCATAATATAAGGGGTCGGTGGACCGGTCG 800
ATGTATGTCTTGTTGCAGATCATCAAGAACACGTAGAGAAACCCAGCTGA 850
TGCATGGAGATACACCTACATTGCATGAATATATGTTAGATTTGCAACCA 900
GAGACAACTGATCTCTACTGTTATGAGCAATTAAATGACAGCTCAGAGGA 950
GGAGGATGAAATAGATGGTCCAGCTGGACAAGCAGAACCGGACAGAGCCC 1000
ATTACAATATTGTAACCTTTTGTTGCAAGTGTGACTCTACGCTTCGGTTG 1050
TGCGTACAAAGCACACACGTAGACATTCGTACTTTGGAAGACCTGTTAAT 1100
GGGCACACTAGGAATTGTGTGCCCCATCTGTTCTCAGAAACCAACTAGTG 1150
GCCACCATCACCATCACCATTAA 1173

Figure 14A

Peptidic sequence

MKGGIVHSDGSYPKDKFEKINGTWYYFDSSGYMLADRWRKHTDGNWYWFD 50
NSGEMATGWKKIADKWYYFNEEGAMKTGWVKYKDTWYYLDAKEGAMVSNA 100
FIQSADGTGWYYLKPDGTLADRPELASMLDMAMFQDPQERPRKLPQLCTE 150
LQTTIHDIILECVYCKQQLLRREVYDFAFRDLCIVYRDGNPYAVCDKCLK 200
FYSKISEYRHYCYSLYGTTLEQQYNKPLCDLLIRCINCQKPLCPEEKQRH 250
LDKKQRFHNIRGRWTGRCMSCCRSSRTRRETQLMHGDTPTLHEYMLDLQP 300
ETTDLYCYEQLNDSSEEEDEIDGPAGQAEPDRAHYNIVTFCCKCDSTLRL 350
CVQSTHVDIRTLEDLLMGTLGIVCPICSQKPTSGHHHHHH. 391

Figure 14B

SEQUENCE OF PROT.D1/3 -E7-HIS /HPV18

Nucleotidic Sequence

ATGGATCCAAGCAGCCATTCATCAAATATGGCGAATACCCAAATGAAATC 50
AGACAAAATCATTATTGCTCACCGTGGTGCTAGCGGTTATTTACCAGAGC 100
ATACGTTAGAATCTAAAGCACTTGCGTTTGCACAACAGGCTGATTATTTA 150
GAGCAAGATTTAGCAATGACTAAGGATGGTCGTTTAGTGGTTATTCACGA 200
TCACTTTTTAGATGGCTTGACTGATGTTGCGAAAAAATTCCCACATCGTC 250
ATCGTAAAGATGGCCGTTACTATGTCATCGACTTTACCTTAAAAGAAATT 300
CAAAGTTTAGAAATGACAGAAACTTTGAAACCATGGCCATGCATGGACC 350
TAAGGCAACATTGCAAGACATTGTATTGCATTTAGAGCCCCAAAATGAAA 400
TTCCGGTTGACCTTCTATGTCACGAGCAATTAAGCGACTCAGAGGAAGAA 450
AACGATGAAATAGATGAAGTTAATCATCAACATTTACCAGCCCGACGAGC 500
CGAACCACAACGTCACACAATGTTGTGTATGTGTTGTAAGTGTGAAGCCA 550
GAATTGAGCTAGTAGTAGAAAGCTCAGCAGACGACCTTCGAGCATTCCAG 600
CAGCTGTTTCTGAACACCCTGTCCTTTGTGTGTCCGTGGTGTGCATCCCA 650
GCAGACTAGTGGCCACCATCACCATCACCATTAA 684

Figure 16A

Peptidic Sequence

MDPSSHSSNMANTQMKSDKIIIAHRGASGYLPEHTLESKA
40LAFAQQADYLEQDLAMTKDGRLVVIHDHFLDGLTDVAKKF
80PHRHRKDGRYYVIDFTLKEIQSLEMTENFETMAMHGPKAT
120LQDIVLHLEPQNEIPVDLLCHEQLSDSEEENDEIDEVNHQ
160HLPARRAEPQRHTMLCMCCKCEARIELVVESSADDLRAFQ
200QLFLNTLSFVCPWCASQQTSGHHHHHH. 228

Figure 16B

SEQUENCE OF THIOREDOXIN

MSDKIIHLTDDSFDTDVLKADGAILVDFWAEWCGPCKMIA 40
PILDEIADEYQGKLTVAKLNIDQNPGTAPKYGIRGIPTLL 80
LFKNGEVAATKVGALSKGQLKEFLDANLA. 110

Figure 18

SEQUENCE OF PROT.D1/3 - E7 mutated (cys27 → gly, glu29 → gln) HPV18.

Nucleotidic sequence:

ATGGATCCAAGCAGCCATTCATCAAATATGGCGAATACCCAAATGAAATC 50
AGACAAAATCATTATTGCTCACCGTGGTGCTAGCGGTTATTTACCAGAGC 100
ATACGTTAGAATCTAAAGCACTTGCGTTTGCACAACAGGCTGATTATTTA 150
GAGCAAGATTTAGCAATGACTAAGGATGGTCGTTTAGTGGTTATTCACGA 200
TCACTTTTTAGATGGCTTGACTGATGTTGCGAAAAAATTCCCACATCGTC 250
ATCGTAAAGATGGCCGTTACTATGTCATCGACTTTACCTTAAAAGAAATT 300
CAAAGTTTAGAAATGACAGAAACTTTGAAACCATGGCCATGCATGGACC 350
TAAGGCAACATTGCAAGACATTGTATTGCATTTAGAGCCCCAAAATGAAA 400
TTCCGGTTGACCTTCTAGGTCACCAGCAATTAAGCGACTCAGAGGAAGAA 450
AACGATGAAATAGATGGAGTTAATCATCAACATTTACCAGCCCGACGAGC 500
CGAACCACAACGTCACACAATGTTGTGTATGTGTTGTAAGTGTGAAGCCA 550
GAATTGAGCTAGTAGTAGAAAGCTCAGCAGACGACCTTCGAGCATTCCAG 600
CAGCTGTTTCTGAACACCCTGTCCTTTGTGTGTCCGTGGTGTGCATCCCA 650
GCAGACTAGTGGCCACCATCACCATCACCATTAA 684

Mutations: T418 → G
  G424 → C

Figure 20A

Peptidic sequence:

MDPSSHSSNMANTQMKSDKIIIAHRGASGYLPEHTLESKALAFAQQADYL
EQDLAMTKDGRLVVIHDHFLDGLTDVAKKFPHRHRKDGRYYVIDFTLKEI
QSLEMTENFETMAMHGPKATLQDIVLHLEPQNEIPVDLLGHQQLSDSEEE
NDEIDGVNHQHLPARRAEPQRHTMLCMCCKCEARIELVVESSADDLRAFQ
QLFLNTLSFVCPWCASQQTSGHHHHHH. 228 mutated amino acids: cys27 → gly (=C27→G), glu29 → gln (=E29→Q) of E7 are residues 140 and 142 of the fusion protein.

N term M D P -ProtD1/3(aa4 --> 111)-M A-mutated E7(aa 114 --> 218)-TSGHHHHHH Cterm.

Figure 20B

SEQUENCE OF PROT.D1/3 - E6 - His / HPV18.

Nucleotidic sequence

```
ATGGATCCAAGCAGCCATTCATCAAATATGGCGAATACCCAAATGAAATC 50
AGACAAAATCATTATTGCTCACCGTGGTGCTAGCGGTTATTTACCAGAGC 100
ATACGTTAGAATCTAAAGCACTTGCGTTTGCACAACAGGCTGATTATTTA 150
GAGCAAGATTTAGCAATGACTAAGGATGGTCGTTTAGTGGTTATTCACGA 200
TCACTTTTTAGATGGCTTGACTGATGTTGCGAAAAAATTCCCACATCGTC 250
ATCGTAAAGATGGCCGTTACTATGTCATCGACTTTACCTTAAAAGAAATT 300
CAAAGTTTAGAAATGACAGAAACTTTGAAACCATGGCGCGCTTTGAGGA 350
TCCAACACGGCGACCCTACAAGCTACCTGATCTGTGCACGGAACTGAACA 400
CTTCACTGCAAGACATAGAAATAACCTGTGTATATTGCAAGACAGTATTG 450
GAACTTACAGAGGTATTTGAATTTGCATTTAAAGATTTATTTGTGGTGTA 500
TAGAGACAGTATACCGCATGCTGCATGCCATAAATGTATAGATTTTATT 550
CTAGAATTAGAGAATTAAGACATTATTCAGACTCTGTGTATGGAGACACA 600
TTGGAAAAACTAACTAACACTGGGTTATACAATTTATTAATAAGGTGCCT 650
GCGGTGCCAGAAACCGTTGAATCCAGCAGAAAACTTAGACACCTTAATG 700
AAAAACGACGATTTCACAACATAGCTGGGCACTATAGAGGCCAGTGCCAT 750
TCGTGCTGCAACCGAGCACGACAGGAACGACTCCAACGACGCAGAGAAAC 800
ACAAGTAACTAGTGGCCACCATCACCATCACCATTAA 837
```

Figure 22A

Peptidic sequence

MDPSSHSSNMANTQMKSDKIIIAHRGASGYLPEHTLESKALAFAQQADYL 50
EQDLAMTKDGRLVVIHDHFLDGLTDVAKKFPHRHRKDGRYYVIDFTLKEI 100
QSLEMTENFETMARFEDPTRRPYKLPDLCTELNTSLQDIEITCVYCKTVL 150
ELTEVFEFAFKDLFVVYRDSIPHAACHKCIDFYSRIRELRHYSDSVYGDT 200
LEKLTNTGLYNLLIRCLRCQKPLNPAEKLRHLNEKRRFHNIAGHYRGQCH 250
SCCNRARQERLQRRRETQVTSGHHHHHH. 279

Figure 22B

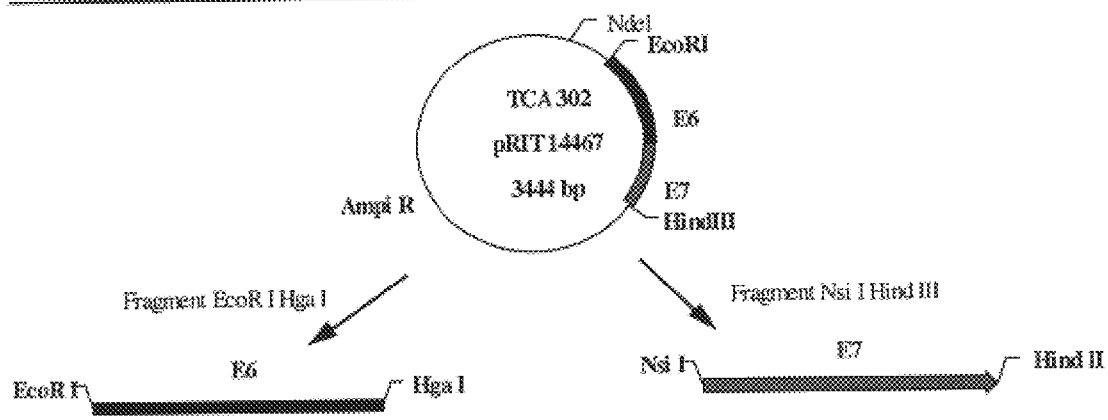
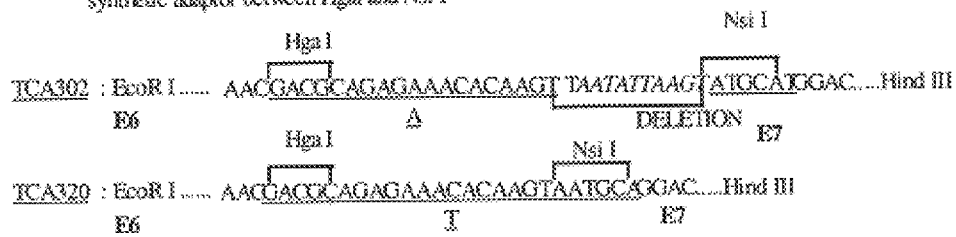
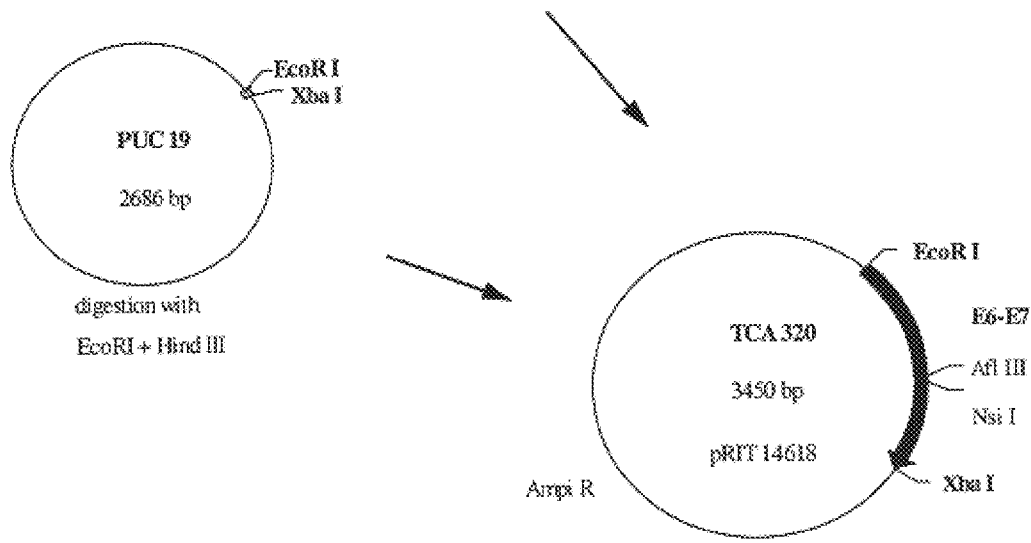
Figure 23

SEQUENCE OF PROT.D1/3 - E6 - E7 - His / HPV18.

Nucleotidic sequence

ATGGATCCAAGCAGCCATTCATCAAATATGGCGAATACCCAAATGAAATC 50
AGACAAAATCATTATTGCTCACCGTGGTGCTAGCGGTTATTTACCAGAGC 100
ATACGTTAGAATCTAAAGCACTTGCGTTTGCACAACAGGCTGATTATTTA 150
GAGCAAGATTTAGCAATGACTAAGGATGGTCGTTTAGTGGTTATTCACGA 200
TCACTTTTAGATGGCTTGACTGATGTTGCGAAAAAATTCCCACATCGTC 250
ATCGTAAAGATGGCCGTTACTATGTCATCGACTTTACCTTAAAAGAAATT 300
CAAAGTTTAGAAATGACAGAAAACTTTGAAACCATGGCGCGCTTTGAGGA 350
TCCAACACGGCGACCCTACAAGCTACCTGATCTGTGCACGGAACTGAACA 400
CTTCACTGCAAGACATAGAAATAACCTGTGTATATTGCAAGACAGTATTG 450
GAACTTACAGAGGTATTTGAATTTGCATTTAAAGATTTATTTGTGGTGTA 500
TAGAGACAGTATACCGCATGCTGCATGCCATAAATGTATAGATTTTATT 550
CTAGAATTAGAGAATTAAGACATTATTCAGACTCTGTGTATGGAGACACA 600
TTGGAAAAACTAACTAACACTGGGTTATACAATTTATTAATAAGGTGCCT 650
GCGGTGCCAGAAACCGTTGAATCCAGCAGAAAAACTTAGACACCTTAATG 700
AAAAACGACGATTTCACAACATAGCTGGGCACTATAGAGGCCAGTGCCAT 750
TCGTGCTGCAACCGAGCACGACAGGAACGACTCCAACGACGCAGAGAAAC 800
ACAAGTAATGCATGGACCTAAGGCAACATTGCAAGACATTGTATTGCATT 850
TAGAGCCCCAAAATGAAATTCCGGTTGACCTTCTATGTCACGAGCAATTA 900
AGCGACTCAGAGGAAGAAAACGATGAAATAGATGGAGTTAATCATCAACA 950
TTTACCAGCCCGACGAGCCGAACCACAACGTCACACAATGTTGTGTATGT 1000
GTTGTAAGTGTGAAGCCAGAATTGAGCTAGTAGTAGAAAGCTCAGCAGAC 1050
GACCTTCGAGCATTCCAGCAGCTGTTTCTGAACACCCTGTCCTTTGTGTG 1100
TCCGTGGTGTGCATCCCAGCAGACTAGTGGCCACCATCACCATCACCATT 1150
AA 1152

Figure 25A

Peptidic sequence

MDPSSHSSNMANTQMKSDKIIIAHRGASGYLPEHTLESKALAFAQQADYL 50
EQDLAMTKDGRLVVIHDHFLDGLTDVAKKFPHRHRKDGRYYVIDFTLKEI 100
QSLEMTENFETMARFEDPTRRPYKLPDLCTELNTSLQDIEITCVYCKTVL 150
ELTEVFEFAFKDLFVVYRDSIPHAACHKCIDFYSRIRELRHYSDSVYGDT 200
LEKLTNTGLYNLLIRCLRCQKPLNPAEKLRHLNEKRRFHNIAGHYRGQCH 250
SCCNRARQERLQRRRETQVMHGPKATLQDIVLHLEPQNEIPVDLLCHEQL 300
SDSEEENDEIDGVNHQHLPARRAEPQRHTMLCMCCKCEARIELVVESSAD 350
DLRAFQQLFLNTLSFVCPWCASQQTSGHHHHHH. 384

Figure 25B

Therapeutic effect of vaccination with ProtD1/3 E7 of HPV16 formulations, on TC1 tumor growth Lymphoproliferation on spleen cells
(stimulation index)
72 Hrs in vitro restimulation with ProtD1/3E7 (0.1; 1 µg/ml)
(exp 96533)

Group 1: ProtD 1/3 E7
Group 2: ProtD 1/3 E7 + SB 62 Qs21 & 3 D MPL
Group 3: SB 62 Qs21 & 3 D MPL
Group 4: PBS Lymphoproliferation on lymph node cells
(stimulation index)
72 Hrs *in vitro* restimulation with ProtD1/3E7 ( 1 µg/ml)
(exp 96533)

Group 1: ProtD 1/3 E7
Group 2: ProtD 1/3 E7 + SB 62 Qs21 & 3 D MPL
Group 3: SB 62 Qs21 & 3 D MPL
Group 4: PBS Subclass-specific antibody response (exp 96533)

group 1: ProtD1/3 E7 HPV16
group 2: ProtD1/3 E7 HPV16+ SB 62 Qs21 & 3 D MPL
group 3: SB 62 Qs21 & 3 D MPL
group 4: PBS Subclass-specific antibody response (exp 96533)

group 1:   ProtD1/3 E7 HPV16
group 2:   ProtD1/3 E7 HPV16+ SB 62 Qs21 & 3 D MPL
group 3:   SB 62 Qs21 & 3 D MPL
group 4:   PBS Subclass-specific antibody response (exp 96533)

group 1: ProtD1/3 E7 HPV16
group 2: ProtD1/3 E7 HPV16+ SB 62 Qs21 & 3 D MPL
group 3: SB 62 Qs21 & 3 D MPL
group 4: PBS Subclass-specific antibody response (exp 96533)

group 1: ProtD1/3 E7 HPV16
group 2: ProtD1/3 E7 HPV16+ SB 62 Qs21 & 3 D MPL
group 3: SB 62 Qs21 & 3 D MPL
group 4: PBS Protective effect of vaccination with ProtD1/3 E7 HPV16 formulations against a
TC1 tumor challenge (2 10e5 cells) (exp 96532)

Lymphoproliferation on spleen cells (Stimulation index) (Exp. 96532)
72 Hrs in vitro re-stimulation with
   A) ProtD1/3 E7 (1; 0.1 μg/ml)
   B) ProtD1/3 E7 (0.1; 0.01 μg/ml) coated on latex μbeads
Group 1: ProtD1/3 E7 HPV16
Group 2: ProtD1/3 E7 HPV16 + SB 62 Qs21 & 3 D MPL
Group 3: SB 62 Qs21 & 3 D MPL
Group 4: PBS Lymphoproliferation on spleen cells (Stimulation index) (Exp. 96532)
72 Hrs *in vitro* re-stimulation with
    A) ProtD1/3 E7 (1; 0.1 µg/ml)
    B) ProtD1/3 E7 (0.1; 0.01 µg/ml) coated on latex µbeads
Group 1: ProtD1/3 E7 HPV16
Group 2: ProtD1/3 E7 HPV16 + SB 62 Qs21 & 3 D MPL
Group 3: SB 62 Qs21 & 3 D MPL
Group 4: PBS Lymphoproliferation on lymph node cells
(Stimulation index) (Exp. 96532)
72 Hrs *in vitro* re-stimulation with A) ProtD1/3 E7 (0.01 µg/ml)
  B) ProtD1/3 E7 (0.01 µg/ml) coated on latex µbeads Group 1: ProtD1/3 E7 HPV16
Group 2: ProtD1/3 E7 HPV16 + SB 62 Qs21 & 3 D MPL
Group 3: SB 62 Qs21 & 3 D MPL
Group 4: PBS

A

Lymphoproliferation on lymph node cells
(Stimulation index) (Exp. 96532)
72 Hrs *in vitro* re-stimulation with A) ProtD1/3 E7 (0.01 µg/ml)
    B) ProtD1/3 E7 (0.01 µg/ml) coated on latex µbeads Group 1: ProtD1/3 E7 HPV16
Group 2: ProtD1/3 E7 HPV16 + SB 62 Qs21 & 3 D MPL
Group 3: SB 62 Qs21 & 3 D MPL
Group 4: PBS

B

Subclass-specific antibody response (exp 96832)

group 1: ProtD/3 E7 HPV16
group 2: ProtD1/3 E7 HPV16 + SB 62 Qs21 & 3 D MPL
group 3: SB 62 Qs21 & 3 D MPL
group 4: medium Subclass-specific antibody response (exp 96532)

group 1: ProtD/3 E7 HPV16
group 2: ProtD1/3 E7 HPV16 + SB 62 Qs21 & 3 D MPL
group 3: SB 62 Qs21 & 3 D MPL
group 4: medium Subclass-specific antibody response (exp 96532)

group 1: ProtD/3 E7 HPV16
group 2: ProtD1/3 E7 HPV16 + SB 62 Qs21 & 3 D MPL
group 3: SB 62 Qs21 & 3 D MPL
group 4: medium Subclass-specific antibody response (exp 96532)

group 1: ProtD/3 E7 HPV16
group 2: ProtD1/3 E7 HPV16 + SB 62 Qs21 & 3 D MPL
group 3: SB 62 Qs21 & 3 D MPL
group 4: medium Lymphoproliferation on spleen cells (stimulation index)
72HRs in vitro re-stimulation with PD1/3 18E7 (10, 1, 0.1, 0.01 µg/ml)
(Exp 98038)

Group 1: ProtD 1/3 18 E7
Group 2: ProtD 1/3 18 E7 + DQS21 + 3D-MPL
Group 3: ProtD 1/3 18 E7 + QS21 + 3D-MPL + SB62 O/W
Group 4: ProtD 1/3 18 E7 + DQS21 alum

| spleen Gr   | 1    | 2    | 3    | 4    |
|-------------|------|------|------|------|
| 18E7 10µg   | 6    | 27   | 23   | 20   |
| 18E7 1µg    | 5    | 23   | 25   | 23   |
| 18E7 0.1µg  | 5    | 21   | 21   | 23   |
| 18 E7 0.01µg| 4    | 14   | 15   | 18   |
| baseline/cpm| 1168 | 1359 | 1025 | 1268 |

Lymphoproliferation on popliteal Lymph nodes
72HRs in vitro re-stimulation with PD1/3 18E7 (10, 1, 0.1, 0.01 µg/ml)
(Exp 98038)

Group 1: ProtD 1/3 18 E7
Group 2: ProtD 1/3 18 E7 + DQS21 + 3D-MPL
Group 3: ProtD 1/3 18 E7 + QS21 + 3D-MPL + SB62 O/W
Group 4: ProtD 1/3 18 E7 + DQS21 alum

| LN Group | 1 | 2 | 3 | 4 |
|---|---|---|---|---|
| 18 E7 10 | 33 | 117 | 108 | 203 |
| 18E7 1 | 8 | 110 | 108 | 208 |
| 18 E7 0.1 | 4 | 95 | 95 | 196 |
| 18 E7 0.01 | 2 | 75 | 81 | 141 |
| baseline | 325 | 161 | 131 | 607 |

Cytokine production in the culture supernatant of spleen cells after 96 Hrs in vitro re-stimulation (ProtD1/3 18E7 1, 3µg/ml)

Group 1: ProtD 1/3 18 E7
Group 2: ProtD 1/3 18 E7 + DQ 3D-MPL
Group 3: ProtD 1/3 18 E7 + QS21, 3D-MPL, SB62 O/W
Group 4: ProtD 1/3 18 E7 + DQ, 3D-MPL alum Cytokine production in the culture supernatant of spleen cells after 96 Hrs in vitro re-stimulation
(ProtD1/3 18E7 1, 3μg/ml)

Group 1: ProtD 1/3 18 E7
Group 2: ProtD 1/3 18 E7 + DQ 3D-MPL
Group 3: ProtD 1/3 18 E7 + QS21, 3D-MPL, SB62 O/W
Group 4: ProtD 1/3 18 E7 + DQ, 3D-MPL alum Antibody response and Isotypic  (exp 98038)

Group 1: ProtD 1/3 18 E7
Group 2: ProtD 1/3 18 E7 + DQS21 3DMPL
Group 3: ProtD 1/3 18 E7 + SB62 QS21/3DMPL
Group 4: ProtD 1/3 18 E7 + MPL DQ alum

| Groups | mid. Dil IgGt tot | IgG1 % | IgG2a % | IgG2b % |
|---|---|---|---|---|
| 1 | 1500 | 46 | 32 | 22 |
| 2 | 84172 | 28 | 48 | 23 |
| 3 | 80545 | 43 | 44 | 13 |
| 4 | 213685 | 82 | 8 | 10 |

Antibody response and Isotypic (exp 98038)

Group 1: ProtD 1/3 18 E7
Group 2: ProtD 1/3 18 E7 + DQS21 3DMPL
Group 3: ProtD 1/3 18 E7 + SB62 QS21/3DMPL
Group 4: ProtD 1/3 18 E7 + MPL DQ alum

| Groups | mid. Dil IgGt tot | IgG1 % | IgG2a % | IgG2b % |
|---|---|---|---|---|
| 1 | 1500 | 46 | 32 | 22 |
| 2 | 84172 | 28 | 48 | 23 |
| 3 | 80545 | 43 | 44 | 13 |
| 4 | 213685 | 82 | 8 | 10 |

SEQUENCE LISTING

<160> NUMBER OF SEQ ID NOS: 23

<210> SEQ ID NO 1
<211> LENGTH: 220
<212> TYPE: PRT
<213> ORGANISM: Homo sapien

<400> SEQUENCE: 1

Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45 yr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80 ro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Met

-continued

```
         100                 105                 110
Ala Met His Gly Asp Thr Pro Thr Leu His Glu Tyr Met Leu Asp Leu
        115                 120                 125

Gln Pro Glu Thr Thr Asp Leu Tyr Cys Tyr Glu Gln Leu Asn Asp Ser
    130                 135                 140

Ser Glu Glu Asp Glu Ile Asp Gly Pro Ala Gly Gln Ala Glu Pro
145                 150                 155                 160

Asp Arg Ala His Tyr Asn Ile Val Thr Phe Cys Cys Lys Cys Asp Ser
                165                 170                 175

Thr Leu Arg Leu Cys Val Gln Ser Thr His Val Asp Ile Arg Thr Leu
            180                 185                 190

Glu Asp Leu Leu Met Gly Thr Leu Gly Ile Val Cys Pro Ile Cys Ser
        195                 200                 205

Gln Lys Pro Thr Ser Gly His His His His His His
    210                 215                 220
```

<210> SEQ ID NO 2
<211> LENGTH: 663
<212> TYPE: DNA
<213> ORGANISM: Homo sapien

<400> SEQUENCE: 2

```
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc      240
ccacatcgtc atcgtaaaga tggccgttac tatgtcatcg actttacctt aaaagaaatt     300
caaagtttag aaatgacaga aaactttgaa accatggcca tgcatggaga tacacctaca    360
ttgcatgaat atatgttaga tttgcaacca gagacaactg atctctactg ttatgagcaa    420
ttaaatgaca gctcagagga ggaggatgaa atagatggtc cagctggaca agcagaaccg    480
gacagagccc attacaatat tgtaaccttt tgttgcaagt gtgactctac gcttcggttg    540
tgcgtacaaa gcacacacgt agacattcgt actttggaag acctgttaat gggcacacta    600
ggaattgtgt gccccatctg ttctcagaaa ccaactagtg gccaccatca ccatcaccat    660
taa                                                                   663
```

<210> SEQ ID NO 3
<211> LENGTH: 822
<212> TYPE: DNA
<213> ORGANISM: Homo sapien

<400> SEQUENCE: 3

```
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc      240
ccacatcgtc atcgtaaaga tggccgttac tatgtcatcg actttacctt aaaagaaatt     300
caaagtttag aaatgacaga aaactttgaa accatggcca tgtttcagga cccacaggag    360
cgacccagaa agttaccaca gttatgcaca gagctgcaaa caactataca tgatataata    420
ttagaatgtg tgtactgcaa gcaacagtta ctgcgacgtg aggtatatga ctttgctttt    480
```

```
cgggatttat gcatagtata tagagatggg aatccatatg ctgtatgtga taaatgttta      540 aagtttatt  ctaaaattag tgagtataga cattattgtt atagtttgta tggaacaaca      600
ttagaacagc aatacaacaa accgttgtgt gatttgttaa ttaggtgtat taactgtcaa      660
aagccactgt gtcctgaaga aaagcaaaga catctggaca aaaagcaaag attccataat      720
ataaggggtc ggtggaccgg tcgatgtatg tcttgttgca gatcatcaag aacacgtaga      780
gaaacccagc tgactagtgg ccaccatcac catcaccatt aa                         822
```

<210> SEQ ID NO 4
<211> LENGTH: 273
<212> TYPE: PRT
<213> ORGANISM: Homo sapien

<400> SEQUENCE: 4

```
Met Asp Pro Ser Ser His Ser Ser Asn Met Ala Asn Thr Gln Met Lys
  1               5                  10                  15

Ser Asp Lys Ile Ile Ala His Arg Gly Ala Ser Gly Tyr Leu Pro
                 20                  25                  30

Glu His Thr Leu Glu Ser Lys Ala Leu Ala Phe Ala Gln Gln Ala Asp
             35                  40                  45

Tyr Leu Glu Gln Asp Leu Ala Met Thr Lys Asp Gly Arg Leu Val Val
         50                  55                  60

Ile His Asp His Phe Leu Asp Gly Leu Thr Asp Val Ala Lys Lys Phe
 65                  70                  75                  80

Pro His Arg His Arg Lys Asp Gly Arg Tyr Tyr Val Ile Asp Phe Thr
                 85                  90                  95

Leu Lys Glu Ile Gln Ser Leu Glu Met Thr Glu Asn Phe Glu Thr Met
            100                 105                 110

Ala Met Phe Gln Asp Pro Gln Glu Arg Pro Arg Lys Leu Pro Gln Leu
        115                 120                 125

Cys Thr Glu Leu Gln Thr Thr Ile His Asp Ile Ile Leu Glu Cys Val
    130                 135                 140

Tyr Cys Lys Gln Gln Leu Leu Arg Arg Glu Val Tyr Asp Phe Ala Phe
145                 150                 155                 160

Arg Asp Leu Cys Ile Val Tyr Arg Asp Gly Asn Pro Tyr Ala Val Cys
                165                 170                 175

Asp Lys Cys Leu Lys Phe Tyr Ser Lys Ile Ser Glu Tyr Arg His Tyr
            180                 185                 190

Cys Tyr Ser Leu Tyr Gly Thr Thr Leu Glu Gln Gln Tyr Asn Lys Pro
        195                 200                 205

Leu Cys Asp Leu Leu Ile Arg Cys Ile Asn Cys Gln Lys Pro Leu Cys
    210                 215                 220

Pro Glu Glu Lys Gln Arg His Leu Asp Lys Lys Gln Arg Phe His Asn
225                 230                 235                 240

Ile Arg Gly Arg Trp Thr Gly Arg Cys Met Ser Cys Cys Arg Ser Ser
                245                 250                 255

Arg Thr Arg Arg Glu Thr Gln Leu Thr Ser Gly His His His His His
            260                 265                 270

His
```

<210> SEQ ID NO 5
<211> LENGTH: 1116
<212> TYPE: DNA
<213> ORGANISM: Homo sapien

```
<400> SEQUENCE: 5
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc      240
ccacatcgtc atcgtaaaga tggccgttac tatgtcatcg actttacctt aaaagaaatt     300
caaagtttag aaatgacaga aactttgaa accatggcca tgtttcagga cccacaggag      360
cgacccagaa agttaccaca gttatgcaca gagctgcaaa caactataca tgatataata     420
ttagaatgtg tgtactgcaa gcaacagtta ctgcgacgtg aggtatatga ctttgctttt     480
cgggatttat gcatagtata tagagatggg aatccatatg ctgtatgtga taatgtttta     540
aagtttatt ctaaaattag tgagtataga cattattgtt atagtttgta tggaacaaca      600
ttagaacagc aatacaacaa accgttgtgt gatttgttaa ttaggtgtat taactgtcaa     660
aagccactgt gtcctgaaga aaagcaaaga catctggaca aaaagcaaag attccataat     720
ataaggggtc ggtggaccgg tcgatgtatg tcttgttgca gatcatcaag aacacgtaga     780
gaaacccagc tgatgcatgg agatacacct acattgcatg aatatatgtt agatttgcaa     840
ccagagacaa ctgatctcta ctgttatgag caattaaatg acagctcaga ggaggaggat     900
gaaatagatg gtccagctgg acaagcagaa ccggacagag cccattacaa tattgtaacc     960
ttttgttgca agtgtgactc tacgcttcgg ttgtgcgtac aaagcacaca cgtagacatt    1020
cgtactttgg aagacctgtt aatgggcaca ctaggaattg tgtgccccat ctgttctcag    1080
aaaccaacta gtggccacca tcaccatcac cattaa                              1116

<210> SEQ ID NO 6
<211> LENGTH: 371
<212> TYPE: PRT
<213> ORGANISM: Homo sapien

<400> SEQUENCE: 6

Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Met
            100                 105                 110

Ala Met Phe Gln Asp Pro Gln Glu Arg Pro Arg Lys Leu Pro Gln Leu
        115                 120                 125

Cys Thr Glu Leu Gln Thr Thr Ile His Asp Ile Leu Glu Cys Val
    130                 135                 140

Tyr Cys Lys Gln Gln Leu Leu Arg Arg Glu Val Tyr Asp Phe Ala Phe
145                 150                 155                 160

Arg Asp Leu Cys Ile Val Tyr Arg Asp Gly Asn Pro Tyr Ala Val Cys
```

```
                         165                 170                 175
Asp Lys Cys Leu Lys Phe Tyr Ser Lys Ile Ser Glu Tyr Arg His Tyr
                    180                 185                 190

Cys Tyr Ser Leu Tyr Gly Thr Thr Leu Glu Gln Gln Tyr Asn Lys Pro
                195                 200                 205

Leu Cys Asp Leu Leu Ile Arg Cys Ile Asn Cys Gln Lys Pro Leu Cys
            210                 215                 220

Pro Glu Glu Lys Gln Arg His Leu Asp Lys Lys Gln Arg Phe His Asn
225                 230                 235                 240

Ile Arg Gly Arg Trp Thr Gly Arg Cys Met Ser Cys Cys Arg Ser Ser
                245                 250                 255

Arg Thr Arg Arg Glu Thr Gln Leu Met His Gly Asp Thr Pro Thr Leu
                260                 265                 270

His Glu Tyr Met Leu Asp Leu Gln Pro Glu Thr Thr Asp Leu Tyr Cys
                275                 280                 285

Tyr Glu Gln Leu Asn Asp Ser Ser Glu Glu Glu Asp Glu Ile Asp Gly
                290                 295                 300

Pro Ala Gly Gln Ala Glu Pro Asp Arg Ala His Tyr Asn Ile Val Thr
305                 310                 315                 320 he Cys Cys Lys Cys Asp Ser Thr Leu Arg Leu Cys Val Gln Ser Thr
                325                 330                 335

His Val Asp Ile Arg Thr Leu Glu Asp Leu Leu Met Gly Thr Leu Gly
                340                 345                 350

Ile Val Cys Pro Ile Cys Ser Gln Lys Pro Thr Ser Gly His His His
                355                 360                 365

His His His
        370

<210> SEQ ID NO 7
<211> LENGTH: 663
<212> TYPE: DNA
<213> ORGANISM: Homo sapien

<400> SEQUENCE: 7
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc     240
ccacatcgtc atcgtaaaga tggccgttac tatgtcatcg actttacctt aaaagaaatt     300
caaagtttag aaatgacaga aactttgaa accatggcca tgcatggaga tacacctaca     360
ttgcatgaat atatgttaga tttgcaacca gagacaactg atctctacgg ttatcagcaa     420
ttaaatgaca gctcagagga ggaggatgaa atagatggtc cagctggaca agcagaaccg     480
gacagagccc attacaatat tgtaaccttt tgttgcaagt gtgactctac gcttcggttg     540
tgcgtacaaa gcacacacgt agacattcgt actttggaag acctgttaat gggcacacta     600
ggaattgtgt gccccatctg ttctcagaaa ccaactagtg gccaccatca ccatcaccat     660
taa                                                                  663

<210> SEQ ID NO 8
<211> LENGTH: 220
<212> TYPE: PRT
<213> ORGANISM: Homo sapien
```

-continued

```
<400> SEQUENCE: 8

Met Asp Pro Ser Ser His Ser Asn Met Ala Asn Thr Gln Met Lys
  1               5                  10                  15

Ser Asp Lys Ile Ile Ala His Arg Gly Ala Ser Gly Tyr Leu Pro
             20                  25                  30

Glu His Thr Leu Glu Ser Lys Ala Leu Ala Phe Ala Gln Gln Ala Asp
         35                  40                  45

Tyr Leu Glu Gln Asp Leu Ala Met Thr Lys Asp Gly Arg Leu Val Val
 50                  55                  60

Ile His Asp His Phe Leu Asp Gly Leu Thr Asp Val Ala Lys Lys Phe
 65                  70                  75                  80

Pro His Arg His Arg Lys Asp Gly Arg Tyr Tyr Val Ile Asp Phe Thr
                 85                  90                  95

Leu Lys Glu Ile Gln Ser Leu Glu Met Thr Glu Asn Phe Glu Thr Met
                100                 105                 110

Ala Met His Gly Asp Thr Pro Thr Leu His Glu Tyr Met Leu Asp Leu
            115                 120                 125

Gln Pro Glu Thr Thr Asp Leu Tyr Gly Tyr Gln Leu Asn Asp Ser
        130                 135                 140

Ser Glu Glu Glu Asp Glu Ile Asp Gly Pro Ala Gly Gln Ala Glu Pro
145                 150                 155                 160

Asp Arg Ala His Tyr Asn Ile Val Thr Phe Cys Cys Lys Cys Asp Ser
                165                 170                 175

Thr Leu Arg Leu Cys Val Gln Ser Thr His Val Asp Ile Arg Thr Leu
            180                 185                 190

Glu Asp Leu Leu Met Gly Thr Leu Gly Ile Val Cys Pro Ile Cys Ser
        195                 200                 205

Gln Lys Pro Thr Ser Gly His His His His His
    210                 215                 220

<210> SEQ ID NO 9
<211> LENGTH: 879
<212> TYPE: DNA
<213> ORGANISM: Homo sapien

<400> SEQUENCE: 9
atgaaagggg gaattgtaca ttcagacggc tcttatccaa agacaagtt tgagaaaatc      60 aatggcactt ggtactactt tgacagttca ggctatatgc ttgcagaccg ctggaggaag    120
cacacagacg gcaactggta ctggttcgac aactcaggcg aaatggctac aggctggaag    180
aaaatcgctg ataagtggta ctatttcaac gaagaaggtg ccatgaagac aggctgggtc    240
aagtacaagg acacttggta ctacttagac gctaaagaag gcgccatggt atcaaatgcc    300
tttatccagt cagcggacgg aacaggctgg tactacctca aaccgacgg aacactggca    360 gacaggccag aattggccag catgctggac atggccatgt tcaggaccc acaggagcga    420 cccagaaagt taccacagtt atgcacagag ctgcaaacaa ctatacatga tataatatta    480
gaatgtgtgt actgcaagca acagttactg cgacgtgagg tatatgactt tgctttcgg    540 gatttatgca tagtatatag agatgggaat ccatatgctg tatgtgataa atgtttaaag    600
ttttattcta aaattagtga gtatagacat tattgttata gtttgtatgg aacaacatta    660
gaacagcaat acaacaaacc gttgtgtgat ttgttaatta ggtgtattaa ctgtcaaaag    720
ccactgtgtc ctgaagaaaa gcaaagacat ctggacaaaa agcaaagatt ccataatata    780
aggggtcggt ggaccggtcg atgtatgtct tgttgcagat catcaagaac acgtagagaa    840
```
acccagctga ctagtggcca ccatcaccat caccattaa                              879

<210> SEQ ID NO 10
<211> LENGTH: 292
<212> TYPE: PRT
<213> ORGANISM: Homo sapien

<400> SEQUENCE: 10

Met Lys Gly Gly Ile Val His Ser Asp Gly Ser Tyr Pro Lys Asp Lys
1               5                   10                  15

Phe Glu Lys Ile Asn Gly Thr Trp Tyr Tyr Phe Asp Ser Ser Gly Tyr
            20                  25                  30

Met Leu Ala Asp Arg Trp Arg Lys His Thr Asp Gly Asn Trp Tyr Trp
        35                  40                  45

Phe Asp Asn Ser Gly Glu Met Ala Thr Gly Trp Lys Lys Ile Ala Asp
    50                  55                  60

Lys Trp Tyr Tyr Phe Asn Glu Glu Gly Ala Met Lys Thr Gly Trp Val
65                  70                  75                  80

Lys Tyr Lys Asp Thr Trp Tyr Tyr Leu Asp Ala Lys Glu Gly Ala Met
                85                  90                  95

Val Ser Asn Ala Phe Ile Gln Ser Ala Asp Gly Thr Gly Trp Tyr Tyr
            100                 105                 110

Leu Lys Pro Asp Gly Thr Leu Ala Asp Arg Pro Glu Leu Ala Ser Met
        115                 120                 125

Leu Asp Met Ala Met Phe Gln Asp Pro Gln Glu Arg Pro Arg Lys Leu
    130                 135                 140

Pro Gln Leu Cys Thr Glu Leu Gln Thr Thr Ile His Asp Ile Ile Leu
145                 150                 155                 160

Glu Cys Val Tyr Cys Lys Gln Gln Leu Leu Arg Arg Glu Val Tyr Asp
                165                 170                 175

Phe Ala Phe Arg Asp Leu Cys Ile Val Tyr Arg Asp Gly Asn Pro Tyr
            180                 185                 190

Ala Val Cys Asp Lys Cys Leu Lys Phe Tyr Ser Lys Ile Ser Glu Tyr
        195                 200                 205

Arg His Tyr Cys Tyr Ser Leu Tyr Gly Thr Thr Leu Glu Gln Gln Tyr
    210                 215                 220

Asn Lys Pro Leu Cys Asp Leu Leu Ile Arg Cys Ile Asn Cys Gln Lys
225                 230                 235                 240

Pro Leu Cys Pro Glu Glu Lys Gln Arg His Leu Asp Lys Lys Gln Arg
                245                 250                 255

Phe His Asn Ile Arg Gly Arg Trp Thr Gly Arg Cys Met Ser Cys Cys
            260                 265                 270

Arg Ser Ser Arg Thr Arg Arg Glu Thr Gln Leu Thr Ser Gly His His
        275                 280                 285

His His His His
    290

<210> SEQ ID NO 11
<211> LENGTH: 720
<212> TYPE: DNA
<213> ORGANISM: Homo sapien

<400> SEQUENCE: 11
atgaaagggg gaattgtaca ttcagacggc tcttatccaa aagacaagtt tgagaaaatc    60
aatggcactt ggtactactt tgacagttca ggctatatgc ttgcagaccg ctggaggaag   120

```
cacacagacg gcaactggta ctggttcgac aactcaggcg aaatggctac aggctggaag      180
aaaatcgctg ataagtggta ctatttcaac gaagaaggtg ccatgaagac aggctgggtc      240
aagtacaagg acacttggta ctacttagac gctaaagaag cgccatggt atcaaatgcc       300 tttatccagt cagcggacgg aacaggctgg tactacctca aaccagacgg aacactggca      360
gacaggccag aattggccag catgctggac atggccatgc atggagatac acctacattg      420
catgaatata tgttagattt gcaaccagag acaactgatc tctactgtta tgagcaatta      480
aatgacagct cagaggagga ggatgaaata gatggtccag ctggacaagc agaaccggac      540
agagcccatt acaatattgt aaccttttgt tgcaagtgtg actctacgct tcggttgtgc      600
gtacaaagca cacgtaga cattcgtact ttggaagacc tgttaatggg cacactagga       660
attgtgtgcc ccatctgttc tcagaaacca actagtggcc accatcacca tcaccattaa     720
```

<210> SEQ ID NO 12
<211> LENGTH: 239
<212> TYPE: PRT
<213> ORGANISM: Homo sapien

<400> SEQUENCE: 12

```
Met Lys Gly Gly Ile Val His Ser Asp Gly Ser Tyr Pro Lys Asp Lys
 1               5                  10                  15

Phe Glu Lys Ile Asn Gly Thr Trp Tyr Tyr Phe Asp Ser Ser Gly Tyr
                20                  25                  30

Met Leu Ala Asp Arg Trp Arg Lys His Thr Asp Gly Asn Trp Tyr Trp
            35                  40                  45

Phe Asp Asn Ser Gly Glu Met Ala Thr Gly Trp Lys Lys Ile Ala Asp
        50                  55                  60

Lys Trp Tyr Tyr Phe Asn Glu Glu Gly Ala Met Lys Thr Gly Trp Val
 65                  70                  75                  80

Lys Tyr Lys Asp Thr Trp Tyr Tyr Leu Asp Ala Lys Glu Gly Ala Met
                85                  90                  95

Val Ser Asn Ala Phe Ile Gln Ser Ala Asp Gly Thr Gly Trp Tyr Tyr
            100                 105                 110

Leu Lys Pro Asp Gly Thr Leu Ala Asp Arg Pro Glu Leu Ala Ser Met
        115                 120                 125

Leu Asp Met Ala Met His Gly Asp Thr Pro Thr Leu His Glu Tyr Met
130                 135                 140

Leu Asp Leu Gln Pro Glu Thr Thr Asp Leu Tyr Cys Tyr Glu Gln Leu
145                 150                 155                 160

Asn Asp Ser Ser Glu Glu Glu Asp Glu Ile Asp Gly Pro Ala Gly Gln
                165                 170                 175

Ala Glu Pro Asp Arg Ala His Tyr Asn Ile Val Thr Phe Cys Cys Lys
            180                 185                 190

Cys Asp Ser Thr Leu Arg Leu Cys Val Gln Ser Thr His Val Asp Ile
        195                 200                 205

Arg Thr Leu Glu Asp Leu Leu Met Gly Thr Leu Gly Ile Val Cys Pro
    210                 215                 220

Ile Cys Ser Gln Lys Pro Thr Ser Gly His His His His His His
225                 230                 235
```

<210> SEQ ID NO 13
<211> LENGTH: 1173
<212> TYPE: DNA
<213> ORGANISM: Homo sapien

<400> SEQUENCE: 13

```
atgaaagggg gaattgtaca ttcagacggc tcttatccaa agacaagtt tgagaaaatc      60
aatggcactt ggtactactt tgacagttca ggctatatgc ttgcagaccg ctggaggaag    120
cacacagacg gcaactggta ctggttcgac aactcaggcg aaatggctac aggctggaag    180
aaaatcgctg ataagtggta ctatttcaac gaagaaggtg ccatgaagac aggctgggtc    240
aagtacaagg acacttggta ctacttagac gctaaagaag gcgccatggt atcaaatgcc    300
tttatccagt cagcggacgg aacaggctgg tactacctca aaccagacgg aacactggca    360
gacaggccag aattggccag catgctggac atggccatgt tcaggaccc acaggagcga     420
cccagaaagt taccacagtt atgcacagag ctgcaaacaa ctatacatga tataatatta    480
gaatgtgtgt actgcaagca acagttactg cgacgtgagg tatatgactt tgcttttcgg    540
gatttatgca tagtatatag agatgggaat ccatatgctg tatgtgataa atgtttaaag    600
ttttattcta aaattagtga gtatagacat tattgttata gtttgtatgg aacaacatta    660
gaacagcaat acaacaaacc gttgtgtgat ttgttaatta ggtgtattaa ctgtcaaaag    720
ccactgtgtc ctgaagaaaa gcaaagacat ctggacaaaa gcaaagatt ccataatata     780
aggggtcggt ggaccggtcg atgtatgtct tgttgcagat catcaagaac acgtagagaa    840
acccagctga tgcatggaga tacacctaca ttgcatgaat atatgttaga tttgcaacca    900
gagacaactg atctctactg ttatgagcaa ttaaatgaca gctcagagga ggaggatgaa    960
atagatggtc cagctggaca agcagaaccg gacagagccc attacaatat tgtaacctt    1020
tgttgcaagt gtgactctac gcttcggttg tgcgtacaaa gcacacacgt agacattcgt    1080
actttggaag acctgttaat gggcacacta ggaattgtgt gccccatctg ttctcagaaa    1140
ccaactagtg gccaccatca ccatcaccat taa                                 1173
```

<210> SEQ ID NO 14
<211> LENGTH: 390
<212> TYPE: PRT
<213> ORGANISM: Homo sapien

<400> SEQUENCE: 14

```
Met Lys Gly Gly Ile Val His Ser Asp Gly Ser Tyr Pro Lys Asp Lys
 1               5                  10                  15

Phe Glu Lys Ile Asn Gly Thr Trp Tyr Tyr Phe Asp Ser Ser Gly Tyr
                20                  25                  30

Met Leu Ala Asp Arg Trp Arg Lys His Thr Asp Gly Asn Trp Tyr Trp
            35                  40                  45

Phe Asp Asn Ser Gly Glu Met Ala Thr Gly Trp Lys Lys Ile Ala Asp
        50                  55                  60

Lys Trp Tyr Tyr Phe Asn Glu Glu Gly Ala Met Lys Thr Gly Trp Val
    65                  70                  75                  80

Lys Tyr Lys Asp Thr Trp Tyr Tyr Leu Asp Ala Lys Glu Gly Ala Met
                85                  90                  95

Val Ser Asn Ala Phe Ile Gln Ser Ala Asp Gly Thr Gly Trp Tyr Tyr
            100                 105                 110

Leu Lys Pro Asp Gly Thr Leu Ala Asp Arg Pro Glu Leu Ala Ser Met
        115                 120                 125

Leu Asp Met Ala Met Phe Gln Asp Pro Gln Glu Arg Pro Arg Lys Leu
    130                 135                 140

Pro Gln Leu Cys Thr Glu Leu Gln Thr Thr Ile His Asp Ile Ile Leu
```

```
                145                 150                 155                 160
Glu Cys Val Tyr Cys Lys Gln Gln Leu Leu Arg Arg Glu Val Tyr Asp
                    165                 170                 175
Phe Ala Phe Arg Asp Leu Cys Ile Val Tyr Arg Asp Gly Asn Pro Tyr
                180                 185                 190
Ala Val Cys Asp Lys Cys Leu Lys Phe Tyr Ser Lys Ile Ser Glu Tyr
                195                 200                 205
Arg His Tyr Cys Tyr Ser Leu Tyr Gly Thr Thr Leu Glu Gln Gln Tyr
                210                 215                 220
Asn Lys Pro Leu Cys Asp Leu Leu Ile Arg Cys Ile Asn Cys Gln Lys
225                 230                 235                 240
Pro Leu Cys Pro Glu Glu Lys Gln Arg His Leu Asp Lys Lys Gln Arg
                245                 250                 255
Phe His Asn Ile Arg Gly Arg Trp Thr Gly Arg Cys Met Ser Cys Cys
                260                 265                 270
Arg Ser Ser Arg Thr Arg Arg Glu Thr Gln Leu Met His Gly Asp Thr
                275                 280                 285
Pro Thr Leu His Glu Tyr Met Leu Asp Leu Gln Pro Glu Thr Thr Asp
                290                 295                 300
Leu Tyr Cys Tyr Glu Gln Leu Asn Asp Ser Ser Glu Glu Glu Asp Glu
305                 310                 315                 320
Ile Asp Gly Pro Ala Gly Gln Ala Glu Pro Asp Arg Ala His Tyr Asn
                325                 330                 335
Ile Val Thr Phe Cys Cys Lys Cys Asp Ser Thr Leu Arg Leu Cys Val
                340                 345                 350
Gln Ser Thr His Val Asp Ile Arg Thr Leu Glu Asp Leu Leu Met Gly
                355                 360                 365
Thr Leu Gly Ile Val Cys Pro Ile Cys Ser Gln Lys Pro Thr Ser Gly
                370                 375                 380
His His His His His His
385                 390

<210> SEQ ID NO 15
<211> LENGTH: 684
<212> TYPE: DNA
<213> ORGANISM: Homo sapien

<400> SEQUENCE: 15
atggatccaa gcagccattc atcaaatatg gcgaatacc  aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc     240
ccacatcgtc atcgtaaaga tggccgttac tatgtcatcg actttacctt aaaagaaatt     300
caaagtttag aaatgacaga aaactttgaa accatggcca tgcatggacc taaggcaaca     360
ttgcaagaca ttgtattgca tttagagccc caaaatgaaa ttccggttga ccttctatgt     420
cacgagcaat taagcgactc agaggaagaa acgatgaaa  tagatgaagt taatcatcaa     480
catttaccag cccgacgagc cgaaccacaa cgtcacacaa tgttgtgtat gtgttgtaag     540
tgtgaagcca gaattgagct agtagtagaa agctcagcag acgaccttcg agcattccag     600
cagctgtttc tgaacaccct gtcctttgtg tgtccgtggt gtgcatccca gcagactagt     660
ggccaccatc accatcacca ttaa                                             684
```

```
<210> SEQ ID NO 16
<211> LENGTH: 227
<212> TYPE: PRT
<213> ORGANISM: Homo sapien

<400> SEQUENCE: 16

Met Asp Pro Ser Ser His Ser Ser Asn Met Ala Asn Thr Gln Met Lys
 1               5                  10                  15

Ser Asp Lys Ile Ile Ala His Arg Gly Ala Ser Gly Tyr Leu Pro
                20                  25                  30

Glu His Thr Leu Glu Ser Lys Ala Leu Ala Phe Ala Gln Gln Ala Asp
                35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Met
                100                 105                 110

Ala Met His Gly Pro Lys Ala Thr Leu Gln Asp Ile Val Leu His Leu
            115                 120                 125

Glu Pro Gln Asn Glu Ile Pro Val Asp Leu Leu Cys His Glu Gln Leu
130                 135                 140

Ser Asp Ser Glu Glu Asn Asp Glu Ile Asp Glu Val Asn His Gln
145                 150                 155                 160

His Leu Pro Ala Arg Arg Ala Glu Pro Gln Arg His Thr Met Leu Cys
                165                 170                 175

Met Cys Cys Lys Cys Glu Ala Arg Ile Glu Leu Val Val Glu Ser Ser
            180                 185                 190

Ala Asp Asp Leu Arg Ala Phe Gln Gln Leu Phe Leu Asn Thr Leu Ser
            195                 200                 205

Phe Val Cys Pro Trp Cys Ala Ser Gln Gln Thr Ser Gly His His His
    210                 215                 220

His His His
225

<210> SEQ ID NO 17
<211> LENGTH: 109
<212> TYPE: PRT
<213> ORGANISM: Homo sapien

<400> SEQUENCE: 17

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95
```

```
Lys Gly Gln Leu Lys Glu Phe Leu Asp Ala Asn Leu Ala
            100                 105
```

<210> SEQ ID NO 18
<211> LENGTH: 684
<212> TYPE: DNA
<213> ORGANISM: Homo sapien

<400> SEQUENCE: 18

```
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcacttttta gatggcttga ctgatgttgc gaaaaaattc     240
ccacatcgtc atcgtaaaga tggccgttac tatgtcatcg actttacctt aaaagaaatt     300
caaagtttag aaatgacaga aactttgaa accatggcca tgcatggacc taaggcaaca     360
ttgcaagaca ttgtattgca tttagagccc caaaatgaaa ttccggttga ccttctaggt     420
caccagcaat taagcgactc agaggaagaa acgatgaaa tagatggagt taatcatcaa     480
catttaccag cccgacgagc cgaaccacaa cgtcacacaa tgttgtgtat gtgttgtaag     540
tgtgaagcca gaattgagct agtagtagaa agctcagcag acgaccttcg agcattccag     600
cagctgtttc tgaacaccct gtcctttgtg tgtccgtggt gtgcatccca gcagactagt     660
ggccaccatc accatcacca ttaa                                            684
```

<210> SEQ ID NO 19
<211> LENGTH: 227
<212> TYPE: PRT
<213> ORGANISM: Homo sapien

<400> SEQUENCE: 19

```
Met Asp Pro Ser Ser His Ser Ser Asn Met Ala Asn Thr Gln Met Lys
 1               5                  10                  15
Ser Asp Lys Ile Ile Ile Ala His Arg Gly Ala Ser Gly Tyr Leu Pro
             20                  25                  30
Glu His Thr Leu Glu Ser Lys Ala Leu Ala Phe Ala Gln Gln Ala Asp
         35                  40                  45
Tyr Leu Glu Gln Asp Leu Ala Met Thr Lys Asp Gly Arg Leu Val Val
     50                  55                  60
Ile His Asp His Phe Leu Asp Gly Leu Thr Asp Val Ala Lys Lys Phe
 65                  70                  75                  80
Pro His Arg His Arg Lys Asp Gly Arg Tyr Tyr Val Ile Asp Phe Thr
                 85                  90                  95
Leu Lys Glu Ile Gln Ser Leu Glu Met Thr Glu Asn Phe Glu Thr Met
            100                 105                 110
Ala Met His Gly Pro Lys Ala Thr Leu Gln Asp Ile Val Leu His Leu
        115                 120                 125
Glu Pro Gln Asn Glu Ile Pro Val Asp Leu Leu Gly His Gln Gln Leu
    130                 135                 140
Ser Asp Ser Glu Glu Glu Asn Asp Glu Ile Asp Gly Val Asn His Gln
145                 150                 155                 160
His Leu Pro Ala Arg Arg Ala Glu Pro Gln Arg His Thr Met Leu Cys
                165                 170                 175
et Cys Cys Lys Cys Glu Ala Arg Ile Glu Leu Val Val Glu Ser Ser
            180                 185                 190
```

```
Ala Asp Asp Leu Arg Ala Phe Gln Gln Leu Phe Leu Asn Thr Leu Ser
        195                 200                 205

Phe Val Cys Pro Trp Cys Ala Ser Gln Gln Thr Ser Gly His His His
    210                 215                 220

His His His
225
```

<210> SEQ ID NO 20
<211> LENGTH: 837
<212> TYPE: DNA
<213> ORGANISM: Homo sapien

<400> SEQUENCE: 20

```
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc      240
ccacatcgtc atcgtaaaga tggccgttac tatgtcatcg actttacctt aaaagaaatt     300
caaagtttag aaatgacaga aaactttgaa accatggcgc gctttgagga tccaacacgg     360
cgaccctaca gctacctga tctgtgcacg gaactgaaca cttcactgca agacatagaa      420
ataacctgtg tatattgcaa gacagtattg aacttacag aggtatttga atttgcattt      480
aaagatttat ttgtggtgta tagagacagt ataccgcatg ctgcatgcca taatgtata      540
gattttatt ctagaattag agaattaaga cattattcag actctgtgta tggagacaca     600
ttggaaaaac taactaacac tgggttatac aatttattaa taaggtgcct gcggtgccag     660
aaaccgttga atccagcaga aaaacttaga caccttaatg aaaaacgacg atttcacaac     720
atagctgggc actatagagg ccagtgccat tcgtgctgca accgagcacg acaggaacga     780
ctccaacgac gcagagaaac acaagtaact agtggccacc atcaccatca ccattaa        837
```

<210> SEQ ID NO 21
<211> LENGTH: 278
<212> TYPE: PRT
<213> ORGANISM: Homo sapien

<400> SEQUENCE: 21

```
Met Asp Pro Ser Ser His Ser Ser Asn Met Ala Asn Thr Gln Met Lys
  1               5                  10                  15

Ser Asp Lys Ile Ile Ile Ala His Arg Gly Ala Ser Gly Tyr Leu Pro
             20                  25                  30

Glu His Thr Leu Glu Ser Lys Ala Leu Ala Phe Ala Gln Gln Ala Asp
         35                  40                  45

Tyr Leu Glu Gln Asp Leu Ala Met Thr Lys Asp Gly Arg Leu Val Val
     50                  55                  60

Ile His Asp His Phe Leu Asp Gly Leu Thr Asp Val Ala Lys Lys Phe
 65                  70                  75                  80

Pro His Arg His Arg Lys Asp Gly Arg Tyr Tyr Val Ile Asp Phe Thr
                 85                  90                  95

Leu Lys Glu Ile Gln Ser Leu Glu Met Thr Glu Asn Phe Glu Thr Met
            100                 105                 110

Ala Arg Phe Glu Asp Pro Thr Arg Arg Pro Tyr Lys Leu Pro Asp Leu
        115                 120                 125

Cys Thr Glu Leu Asn Thr Ser Leu Gln Asp Ile Glu Ile Thr Cys Val
    130                 135                 140
```

```
Tyr Cys Lys Thr Val Leu Glu Leu Thr Glu Val Phe Glu Phe Ala Phe
145                 150                 155                 160

Lys Asp Leu Phe Val Val Tyr Arg Asp Ser Ile Pro His Ala Ala Cys
            165                 170                 175

His Lys Cys Ile Asp Phe Tyr Ser Arg Ile Arg Glu Leu Arg His Tyr
        180                 185                 190

Ser Asp Ser Val Tyr Gly Asp Thr Leu Glu Lys Leu Thr Asn Thr Gly
    195                 200                 205

Leu Tyr Asn Leu Leu Ile Arg Cys Leu Arg Cys Gln Lys Pro Leu Asn
210                 215                 220

Pro Ala Glu Lys Leu Arg His Leu Asn Glu Lys Arg Arg Phe His Asn
225                 230                 235                 240

Ile Ala Gly His Tyr Arg Gly Gln Cys His Ser Cys Cys Asn Arg Ala
                245                 250                 255

Arg Gln Glu Arg Leu Gln Arg Arg Glu Thr Gln Val Thr Ser Gly
            260                 265                 270

His His His His His His
        275

<210> SEQ ID NO 22
<211> LENGTH: 1152
<212> TYPE: DNA
<213> ORGANISM: Homo sapien

<400> SEQUENCE: 22
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcactttta gatggcttga ctgatgttgc gaaaaaattc     240
ccacatcgtc atcgtaaaga tggccgttac tatgtcatcg actttacctt aaaagaaatt     300
caaagtttag aaatgacaga aactttgaa accatggcgc gctttgagga tccaacacgg     360
cgaccctaca agctacctga tctgtgcacg gaactgaaca cttcactgca agacatagaa     420
ataacctgtg tatattgcaa gacagtattg aacttacag aggtatttga atttgcattt     480
aaagatttat tgtggtgta tagagacagt ataccgcatg ctgcatgcca taatgtata     540 gatttttatt ctagaattag agaattaaga cattattcag actctgtgta tggagacaca     600
ttggaaaaac taactaacac tgggttatac aatttattaa taaggtgcct gcggtgccag     660
aaaccgttga atccagcaga aaacttaga caccttaatg aaaaacgacg atttcacaac     720
atagctgggc actatagagg ccagtgccat cgtgctgca accgagcacg acaggaacga     780
ctccaacgac gcagagaaac acaagtaatg catggaccta aggcaacatt gcaagacatt     840
gtattgcatt tagagcccca aaatgaaatt ccggttgacc ttctatgtca cgagcaatta     900
agcgactcag aggaagaaaa cgatgaaata gatggagtta atcatcaaca tttaccagcc     960
cgacgagccg aaccacaacg tcacacaatg ttgtgtatgt gttgtaagtg tgaagccaga    1020
attgagctag tagtagaaag ctcagcagac gaccttcgag cattccagca gctgtttctg    1080
aacaccctgt cctttgtgtg tccgtggtgt gcatcccagc agactagtgg ccaccatcac    1140
catcaccatt aa                                                        1152

<210> SEQ ID NO 23
<211> LENGTH: 383
```

```
<212> TYPE: PRT
<213> ORGANISM: Homo sapien

<400> SEQUENCE: 23
```

| | | | | | | | | | | | | | | |
|---|---|---|---|---|---|---|---|---|---|---|---|---|---|---|
| Met | Asp | Pro | Ser | Ser | His | Ser | Asn | Met | Ala | Asn | Thr | Gln | Met | Lys |
| 1 | | | | 5 | | | | | 10 | | | | | 15 |
| Ser | Asp | Lys | Ile | Ile | Ile | Ala | His | Arg | Gly | Ala | Ser | Gly | Tyr | Leu | Pro |
| | | | 20 | | | | | 25 | | | | | 30 | | |
| Glu | His | Thr | Leu | Glu | Ser | Lys | Ala | Leu | Ala | Phe | Ala | Gln | Gln | Ala | Asp |
| | | | 35 | | | | | 40 | | | | | 45 | | |
| Tyr | Leu | Glu | Gln | Asp | Leu | Ala | Met | Thr | Lys | Asp | Gly | Arg | Leu | Val | Val |
| | 50 | | | | | 55 | | | | | 60 | | | | |
| Ile | His | Asp | His | Phe | Leu | Asp | Gly | Leu | Thr | Asp | Val | Ala | Lys | Lys | Phe |
| 65 | | | | | 70 | | | | | 75 | | | | | 80 |
| Pro | His | Arg | His | Arg | Lys | Asp | Gly | Arg | Tyr | Tyr | Val | Ile | Asp | Phe | Thr |
| | | | | 85 | | | | | 90 | | | | | 95 | |
| Leu | Lys | Glu | Ile | Gln | Ser | Leu | Glu | Met | Thr | Glu | Asn | Phe | Glu | Thr | Met |
| | | | 100 | | | | | 105 | | | | | 110 | | |
| Ala | Arg | Phe | Glu | Asp | Pro | Thr | Arg | Pro | Tyr | Lys | Leu | Pro | Asp | Leu |
| | | 115 | | | | | 120 | | | | | 125 | | |
| Cys | Thr | Glu | Leu | Asn | Thr | Ser | Leu | Gln | Asp | Ile | Glu | Ile | Thr | Cys | Val |
| 130 | | | | | 135 | | | | | 140 | | | | | |
| Tyr | Cys | Lys | Thr | Val | Leu | Glu | Leu | Thr | Glu | Val | Phe | Glu | Phe | Ala | Phe |
| 145 | | | | | 150 | | | | | 155 | | | | | 160 |
| Lys | Asp | Leu | Phe | Val | Val | Tyr | Arg | Asp | Ser | Ile | Pro | His | Ala | Ala | Cys |
| | | | | 165 | | | | | 170 | | | | | 175 | |
| His | Lys | Cys | Ile | Asp | Phe | Tyr | Ser | Arg | Ile | Arg | Glu | Leu | Arg | His | Tyr |
| | | | 180 | | | | | 185 | | | | | 190 | | |
| Ser | Asp | Ser | Val | Tyr | Gly | Asp | Thr | Leu | Glu | Lys | Leu | Thr | Asn | Thr | Gly |
| | | 195 | | | | | 200 | | | | | 205 | | | |
| Leu | Tyr | Asn | Leu | Leu | Ile | Arg | Cys | Leu | Arg | Cys | Gln | Lys | Pro | Leu | Asn |
| | 210 | | | | | 215 | | | | | 220 | | | | |
| Pro | Ala | Glu | Lys | Leu | Arg | His | Leu | Asn | Glu | Lys | Arg | Arg | Phe | His | Asn |
| 225 | | | | | 230 | | | | | 235 | | | | | 240 |
| Ile | Ala | Gly | His | Tyr | Arg | Gly | Gln | Cys | His | Ser | Cys | Cys | Asn | Arg | Ala |
| | | | | 245 | | | | | 250 | | | | | 255 | |
| Arg | Gln | Glu | Arg | Leu | Gln | Arg | Arg | Glu | Thr | Gln | Val | Met | His | Gly |
| | | | 260 | | | | | 265 | | | | | 270 | | |
| Pro | Lys | Ala | Thr | Leu | Gln | Asp | Ile | Val | Leu | His | Leu | Glu | Pro | Gln | Asn |
| | | 275 | | | | | 280 | | | | | 285 | | | |
| Glu | Ile | Pro | Val | Asp | Leu | Leu | Cys | His | Glu | Gln | Leu | Ser | Asp | Ser | Glu |
| | 290 | | | | | 295 | | | | | 300 | | | | |
| Glu | Glu | Asn | Asp | Glu | Ile | Asp | Gly | Val | Asn | His | Gln | His | Leu | Pro | Ala |
| 305 | | | | | 310 | | | | | 315 | | | | | 320 |
| Arg | Arg | Ala | Glu | Pro | Gln | Arg | His | Thr | Met | Leu | Cys | Met | Cys | Lys |
| | | | | 325 | | | | | 330 | | | | | 335 |
| Cys | Glu | Ala | Arg | Ile | Glu | Leu | Val | Val | Glu | Ser | Ser | Ala | Asp | Asp | Leu |
| | | | 340 | | | | | 345 | | | | | 350 | | |
| Arg | Ala | Phe | Gln | Gln | Leu | Phe | Leu | Asn | Thr | Leu | Ser | Phe | Val | Cys | Pro |
| | | 355 | | | | | 360 | | | | | 365 | | | |
| Trp | Cys | Ala | Ser | Gln | Gln | Thr | Ser | Gly | His | His | His | His |
| 370 | | | | | 375 | | | | | 380 | | |

RECOMBINANT PAPILLOMAVIRUS VACCINE AND METHOD FOR PRODUCTION AND TREATMENT

The present invention relates to fusions proteins, comprising a protein or part of a protein that provides T helper epitopes and an antigen from a human-papilloma virus that find utility in the treatment or prophylaxis of human papilloma induced tumours. In particular the invention relates to fusion proteins comprising an E6 or E7 protein from HPV strain 16 or 18 linked to protein D from Heamophilius influenza B.

Papillomaviruses are small naked DNA tumour viruses (7.9 kilobases, double strand), which are highly species-specific. Over 70 individual human papillomavirus (HPV) genotypes have been described. Papillomaviruses are classified on the basis of species of origin (human, bovine etc.) and of the degree of genetic relatedness with other papillomaviruses from the same species. HPVs are generally specific for the skin or mucosal surfaces and have been broadly classified into "low" and "high" risk on the basis of rare and common, respectively, detection in abnormal or tumour tissue. Low risk HPVs usually cause benign lesions (warts or papillomas) that persist for several months or years. High risk HPVs are associated with cancer. The strongest positive association between an HPV virus and human cancer is that which exist between HPV 16 and 18 and cervical carcinoma. More than ten other HPV types have also been found in cervical carcinomas including HPV 31 and HPV 33 although at less frequency.

Genital HPV infection in young sexually active women is common and most individuals either clear the infection, or if lesions develop, these regress. Only a subset of infected individuals has lesions which progress to high grade intraephithelial neoplasia and only a fraction of these progress further to invasive carcinoma.

The molecular events leading to HPV infection have not been clearly established. The lack of an adequate in vitro system to propagate human papillomaviruses has hampered the progress to a best information about the viral cycle.

Today, the different types of HPVs have been isolated and characterised with the help of cloning systems in bacteria and more recently by PCR amplification. The molecular organisation of the HPV genomes has been defined on a comparative basis with that of the well characterised bovine papillomavirus type 1 (BPV1).

Although minor variations do occur, all HPVs genomes described have at least seven early genes, E1 to E7 and two late genes L1 and L2. In addition, an upstream regulatory region harbors the regulatory sequences which appears to control most transcriptional events of the HPV genome.

E1 and E2 genes are involved in viral replication and transcriptional control, respectively and tend to be disrupted by viral integration. E6 and E7 are involved in viral transformation. E5 has also been implicated in this process.

In the HPVs involved in cervical carcinoma such as HPV 16 and 18, the oncogenic process starts after integration of viral DNA. The integration results in the inactivation of genes coding for the capsid proteins L1 and L2 and loss of E2 repressor function leads to deregulation of the E6/E7 open reading frame installing continuously overexpression of the two early proteins E6 and E7 that will lead to gradually loss of the normal cellular differentiation and the development of the carcinoma. E6 and E7 overcome normal cell cycle by inactivating major tumor suppressor proteins, p53 and pRB, the retinoblastoma gene product, respectively.

Carcinoma of the cervix is common in women and develops through a pre-cancerous intermediate stage to the invasive carcinoma which frequently leads to death. The intermediate stages of the disease is known as cervical intraepithelial neoplasia and is graded I to III in terms of increasing severity (CIN I–III).

Clinically, HPV infection of the female anogenital tract manifests as cervical flat condylomas, the hallmark of which is the koilocytosis affecting predominantly the superficial and intermediate cells of the cervical squamous epithelium.

Koilocytes which are the consequence of a cytopathic effect of the virus, appear as multinucleated cells with a perinuclear clear haloe. The epithelium is thickened with abnormal keratinisation responsible for the warty appearance of the lesion.

Such flat condylomas when positive for the HPV 16 or 18 serotypes, are high-risk factors for the evolution toward cervical intraepithelial neoplasia (CIN) and carcinoma in situ (CIS) which are themselves regarded as precursor lesions of invasive cervix carcinoma.

The natural history of oncogenic HPV infection presents 3 consecutive phases, namely:
(1) a latent infection phase,
(2) a phase of intranuclear viral replication with product of complete virions, which corresponds to the occurrence of koilocytes. At this stage, the HPV is producing its full range of proteins including E2, E5, E6, E7, L1 and L2.
(3) a phase of viral integration into the cellular genome, which triggers the onset of malignant transformation, and corresponds to CIN II and CIN III/CIS with progressive disappearance of koilocytes. At this stage, the expression of E2 is down-regulated, the expression of E6 and E7 is enhanced. Between CIN II/III and CIN III/Cervix carcinoma the viral DNA changes from being episomal in the basal cells to integration of E6 and E7 genes only (tumoral cells). 85% of all cervix carcinomas are squamos cell carcinomas most predominantly related to the HPV16 serotype. 10% and 5% are adenocarcinomas and adenos-quamos cell carcinomas respectively, and both types are predominantly related to HPV 18 serotype. Nevertheless other oncogenic HPV's exist.

International Patent Application No. WO 96/19496 discloses variants of human papilloma virus E6 and E7 proteins, particularly fusion proteins of E6/E7 with a deletion in both the E6 and E7 proteins. These deletion fusion proteins are said to be immunogenic.

The present invention provides compositions comprising either an E6 or E7 or an E6/E7 fusion protein linked to an immunological fusion partner having T cell epitopes.

In a preferred form of the invention, the immunological fusion partner is derived from protein D of Heamophilus influenza B. Preferably the protein D derivative comprises approximately the first 1/3 of the protein, in particular approximately the first N-terminal 100–110 amino acids. The protein D may be lipidated (Lipo Protein D). Other immunological fusion partners include the non-structural protein from influenzae virus, NSI (hemagglutinin). Typically the N terminal 81 amino acids are utilised, although different fragments may be used provided they include T-helper epitopes.

In another embodiment the immunological fusion partner is the protein known as LYTA. Preferably the C terminal portion of the molecule is used. Lyta is derived from Streptococcus pneumoniae which synthesize an N-acetyl-L-alanine amidase, amidase LYTA, (coded by the lytA gen {Gene, 43 (1986) page 265–272} an autolysin that specifically degrades certain bonds in the peptidoglycan backbone. The C-terminal domain of the LYTA protein is responsible for the affinity to the choline or to some choline analogues such as DEAE. This property has been exploited for the development of *E.coli* C-LYTA expressing plasmids useful for expression of fusion proteins. Purification of hybrid proteins containing the C-LYTA fragment at its amino terminus has been described {Biotechnology: 10, (1992) page 795–798}. As used herein a preferred embodiment utilises the repeat portion of the Lyta molecule found in the C terminal end starting at residue 178. A particularly preferred form incorporates residues 188–305.

Accordingly, the present invention in preferred embodiment provides fusion proteins comprising Protein D-E6 from HPV 16, Protein D-E7 from HPV 16 Protein D-E7 from HPV 18, Protein D-E6 from HPV 18, and Protein D E6 E7 from both HPV 16 and 18. The protein D part preferably comprises the first 1/3 of protein D. It will be appreciated that other E6 and E7 proteins may be utilised from other HPV subtypes.

The proteins of the present invention preferably are expressed in *E. coli*. In a preferred embodiment the proteins are expressed with a Histidine tail comprising between 5 to 9 and preferably six Histidine residues. These are advantageous in aiding purification.

The protein E7 may in a preferred embodiment carry a mutation to reduce the binding for the rb site (retinoblastoma gene product) and hence eliminate any potential transforming capacity. Preferred mutations for HPV 16 E7 involve replacing $Cys_{24}$ with Glycine, or Glutamic $acid_{26}$ with Glutamine. In a preferred embodiment the E7 protein contains both these mutations.

Preferred mutations for the HPV 18 $E_7$ involve replacing $Cys_{27}$ with Glycine and/or Glutamic $acid_{29}$ with Glutamine. Again preferably both mutations are present.

Single or double mutations may also be introduced p53 region of $E_6$ to eliminate any potential transforming ability.

In a further embodiment of the invention there is provided and E6 E7 fusion protein from HPV linked to an immunological fusion partner. A preferred Immunological fusion partner is Protein D, more preferable the first 1/3 of protein D.

The present invention also provides a DNA encoding the proteins of the present invention. Such sequences can be inserted into a suitable expression vector and expressed in a suitable host.

A DNA sequence encoding the proteins of the present invention can be synthesized using standard DNA synthesis techniques, such as by enzymatic ligation as described by D. M. Roberts et al. in Biochemistry 1985, 24, 5090–5098, by chemical synthesis, by in vitro enzymatic polymerization, or by PCR technology utilising for example a heat stable polymerase, or by a combination of these techniques.

Enzymatic polymerisation of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10°–37° C., generally in a volume of 50µl or less. Enzymatic ligation of DNA fragments may be carried out using a DNA ligase such as T4 DNA ligase in an appropriate buffer, such as 0.05M Tris (pH 7.4), 0.01M $MgCl_2$, 0.01M dithiothreitol, 1 mM spermidine, 1 mM ATP and 0.1 mg/ml bovine serum albumin, at a temperature of 4° C. to ambient, generally in a volume of 50 ml or less. The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J. Gait, H. W. D. Matthes, M. Singh, B. S. Sproat, and R. C. Titmas, Nucleic Acids Research, 1982, 10, 6243; B. S. Sproat, and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society, 1983, 105, 661; N. D. Sinha, J. Biernat, J. McMannus, and H. Koester, Nucleic Acids Research, 1984, 12, 4539; and H. W. D. Matthes et al., EMBO Journal, 1984, 3, 801.

The process of the invention may be performed by conventional recombinant techniques such as described in Maniatis et al., Molecular Cloning—A Laboratory Manual; Cold Spring Harbor, 1982–1989.

In particular, the process may comprise the steps of:
 i) preparing a replicable or integrating expression vector capable, in a host cell, of expressing a DNA polymer comprising a nucleotide sequence that encodes the protein or an immunogenic derivative thereof;
 ii) transforming a host cell with said vector;
 iii) culturing said transformed host cell under conditions permitting expression of said DNA polymer to produce said protein; and
 iv) recovering said protein.

The term 'transforming' is used herein to mean the introduction of foreign DNA into a host cell. This can be achieved for example by transformation, transfection or infection with an appropriate plasmid or viral vector using e.g. conventional techniques as described in Genetic Engineering; Eds. S. M. Kingsman and A. J. Kingsman; Blackwell Scientific Publications; Oxford, England, 1988. The term 'transformed' or 'transformant' will hereafter apply to the resulting host cell containing and expressing the foreign gene of interest.

Preferably recombinant antigen of the invention are expressed in E. coli. The expression strategy include fusion of E7, E6 or E6/E7 fusion to the 1/3-N-terminal portion of protein D from *Haemophilus influenzae* B, an immunological fusion partner providing T cell helper epitopes. An affinity polyhistidine tail is engineered at the carboxy terminus of the fusion protein allowing for simplified purification. Such recombinant antigen is overexpressed in *E. coli* as insoluble protein.

Preferably the proteins of the invention are coexpressed with thioredoxin in trans (TIT). Coexpression of thioredoxin in trans versus in cis is preferred to keep antigen free of thioredoxin without the need for protease. Thioredoxin coexpression eases the solubilisation of the proteins of the invention. Thioredoxin coexpression has also a significant impact on protein purification yield, on purified-protein solubility and quality.

The expression vectors are novel and also form part of the invention.

The replicable expression vectors may be prepared in accordance with the invention, by cleaving a vector compatible with the host cell to provide a linear DNA segment having an intact replicon, and combining said linear segment with one or more DNA molecules which, together with said linear segment encode the desired product, such as the DNA polymer encoding the protein of the invention, or derivative thereof, under ligating conditions.

Thus, the DNA polymer may be preformed or formed during the construction of the vector, as desired.

The choice of vector will be determined in part by the host cell, which may be prokaryotic or eukaryotic but preferably is *E. coli*. Suitable vectors include plasmids, bacteriophages, cosmids and recombinant viruses.

The preparation of the replicable expression vector may be carried out conventionally with appropriate enzymes for restriction, polymerisation and ligation of the DNA, by procedures described in, for example, Maniatis et al. cited above.

The recombinant host cell is prepared, in accordance with the invention, by transforming a host cell with a replicable expression vector of the invention under transforming conditions. Suitable transforming conditions are conventional and are described in, for example, Maniatis et al. cited above, or "DNA Cloning" Vol. II, D. M. Glover ed., IRL Press Ltd, 1985.

The choice of transforming conditions is determined by the host cell. Thus, a bacterial host such as *E. coli* may be treated with a solution of $CaCl_2$ (Cohen et al., Proc. Nat. Acad. Sci., 1973, 69, 2110) or with a solution comprising a mixture of RbC1, $MnCl_2$, potassium acetate and glycerol, and then with 3-[N-morpholino]-propane-sulphonic acid, RbC1 and glycerol. Mammalian cells in culture may be transformed by calcium co-precipitation of the vector DNA onto the cells. The invention also extends to a host cell transformed with a replicable expression vector of the invention.

Culturing the transformed host cell under conditions permitting expression of the DNA polymer is carried out conventionally, as described in, for example, Maniatis et al. and "DNA Cloning" cited above. Thus, preferably the cell is supplied with nutrient and cultured at a temperature below 50° C.

The product is recovered by conventional methods according to the host cell. Thus, where the host cell is bacterial, such as *E. coli* it may be lysed physically, chemically or enzymaticaly and the protein product isolated from the resulting lysate. Where the host cell is mammalian, the product may generally be isolated from the nutrient medium or from cell free extracts. Conventional protein isolation techniques include selective precipitation, adsorption chromatography, and affinity chromatography including a monoclonal antibody affinity column.

When the proteins of the present invention are expressed with a hisitidine tail (His tag). The proteins can easily be purified by affinity chromatography using an ion metal affinity chromatography column (IMAC) column.

A second chromatographic step, such as Q-sepharose may be utilised either before or after the IMAC column to yield highly purified protein. If the immunological fusion partner is C-LYTA, then it is possible to exploit the affinity of CLYTA for choline and/or DEAE to purify this product. Products containing both C-LYTA and his tags can be easily and efficiently purified in a two step process involving differential affinity chromatography. One step involves the affinity of the His tag to IMAC columns, the other involves the affinity of the C-terminal domain of LYTA for choline or DEAE.

Proteins comprising both a C-LYTA and Hisitidine tag are new and accordingly form one aspect of the invention. These may be purified to high levels (greater than 80% preferably greater than 90%) by a simple two step differential affinity procedure.

The proteins of the present invention are provided preferably at least 80% pure more preferably 90% pure as visualized by SDS PAGE. The protein present a major single band when analysed by SDS PAGE under reducing conditions, and western blot analysis show less than 5% host cell protein contamination.

The present invention also provides pharmaceutical composition comprising a protein of the present invention in a pharmaceutically acceptable excipient. A preferred vaccine composition comprises at least Protein D-E6 from HPV 16 or derivative thereof together with Protein D-E7 from HPV 16. Alternatively the E6 and E7 may be presented in a single molecule, preferably a Protein D E6/E7 fusion. Such vaccine may optionally contain either or both E6 and E7 proteins from HPV 18, preferably in the form of a Protein D-E6 or Protein D-E7 fusion protein or Protein D E6/E7 fusion protein. The vaccines of the present invention may contain other HPV antigens from HPV 16 or 18. In particular, the vaccine may contain L1 or L2 antigen monomers. Alternatively such L1 or L2 antigens may be presented together as a virus like particle or the L1 alone protein may be presented as virus like particle or caposmer structure. Such antigens, virus like particles and capsomer are per se known. See for example WO94/00152, WO94/20137, WO94/05792, & WO93/02184. Additional early proteins may be included such as E2 or preferably E5 for example The vaccine of the present invention may additionally comprise antigens from other HPV strains, preferably from strains HPV 6 11, HPV 31 or 33.

Vaccine preparation is generally described in Vaccine Design—The subunit and adjuvant approach (Ed. Powell and Newman) Pharmaceutical Biotechnology Vol. 6 Plenum Press 1995. Encapsulation within liposomes is described by Fullerton, U.S. Pat. No. 4,235,877.

The proteins of the present invention are preferably adjuvanted in the vaccine formulation of the invention. Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionically derivatised polysaccharides, or polyphosphazenes.

In the formulation of the inventions it is preferred that the adjuvant composition induces a preferential TH1 response. Suitable adjuvant systems include, 20 for example, a combination of monophosphoryl lipid A, preferably 3-de-O-acylated monophosphoryl lipid A (3D-MPL) together with an aluminium salt.

An enhanced system involves the combination of a monophosphoryl lipid A and a saponin derivative particularly the combination of QS21 and 3D-MPL as disclosed in WO 94/00153, or a less reactogenic composition where the QS21 is quenched with cholesterol as disclosed in WO 96/33739.

A particularly potent adjuvant formulation involving QS21, 3D-MPL & tocopherol in an oil in water emulsion is described in WO 95/17210 and is a preferred formulation.

Accordingly in one embodiment of the present invention there is provided a vaccine comprising a protein D (or derivative thereof)—E6 or protein D (or derivative thereof)—E7 adjuvanted with a monophosphoryl lipid A or derivative thereof.

Preferably the vaccine additionally comprises a saponin, more preferably QS21.

Preferably the formulation additional comprises an oil in water emulsion and tocopherol. The present invention also provides a method for producing a vaccine formulation comprising mixing a protein of the present invention together with a pharmaceutically acceptable excipient, such as 3D-MPL.

BRIEF DESCRIPTION OF THE DRAWINGS

FIG. 1*a* sets forth the amino acid sequence of the fusion protein Protein-D1/3-E7-His (HPV16). FIG. 1*b* sets forth the nucleotide sequence of the insert in plasmid TCA308 encoding the fusion protein Protein-D1/3-E7-His (HPV16).

FIG. 3a sets forth the nucleotide sequence of the insert in plasmid TCA307 encoding the fusion protein Protein-D1/3-E6-His /HPV16. FIG. 3b sets forth the amino acid sequence of the fusion protein Protein-D1/3-E6-His /HPV16.

FIG. 4 is a diagram describing the construction of plasmid TCA309.

FIG. 6a sets forth the nucleotide sequence of the insert in plasmid TCA311 encoding the fusion protein Protein-D1/3-E6E7-His /HPV16. FIG. 6b sets forth the amino acid sequence of the fusion protein Protein-D1/3-E6E7-His /HPV 16.

FIG. 8a sets forth the nucleotide sequence of the insert in plasmid TCA347 encoding the fusion protein Protein-D1/3-E7 mutated (cys24→gly, glu26→gln)-His /HPV16. FIG. 8b sets forth the amino acid sequence of the fusion protein Protein-D1/3-E7 mutated (cys24→gly, glu26→gln)-His/ HPV16.

FIG. 10a sets forth the nucleotide sequence of the insert in plasmid TCA332 encoding the fusion protein clyta-E6-His /HPV16. FIG. 10b sets forth the amino acid sequence of the fusion protein clyta-E6-His /HPV16.

FIG. 12a sets forth the nucleotide sequence of the insert in plasmid TCA330 encoding the fusion protein clyta-E7-His /HPV16. FIG. 12b sets forth the amino acid sequence of the fusion protein clyta-E7-His /HPV16.

FIG. 14a sets forth the nucleotide sequence of the insert in plasmid TCA331 encoding the fusion protein clyta-E6E7-His /HPV16. FIG. 14b sets forth the amino acid sequence of the fusion protein clyta-E6E7-His /HPV16.

FIG. 16a sets forth the nucleotide sequence of the insert in plasmid TCA316 encoding the fusion protein Protein-D1/3-E7-His /HPV18. FIG. 16b sets forth the amino acid sequence of the fusion protein Protein-D1/3-E7-His /HPV18.

FIG. 18 sets forth the amino acid sequence of thioredoxin.

FIG. 20a sets forth the nucleotide sequence of the insert in plasmid TCA355 encoding the fusion protein Protein-D1/3-E7 mutated (cys27→gly, glu29→gln)-His /HPV18. FIG. 20b sets forth the amino acid sequence of the fusion protein Protein-D1/3-E7 mutated (cys27+gly, glu294gln)-His /HPV18.

FIG. 22a sets forth the nucleotide sequence of the insert in plasmid TCA314 encoding the fusion protein Protein-D1/3-E6-His /HPV18. FIG. 22b sets forth the amino acid sequence of the fusion protein Protein-D1/3-E6-His /HPV18.

FIG. 23 is a diagram describing the construction of plasmid TCA320.

FIG. 25a sets forth the nucleotide sequence of the insert in plasmid TCA328 encoding the fusion protein Protein-D1/3-E6E7-His /HPV18. FIG. 25b sets forth the amino acid sequence of the fusion protein Protein-D1/3-E6E7-His /HPV18.

FIG. 29 presents data on E7-specific antibody titers obtained from mice treated with Protein-D1/3-E7-His /HPV16 formulations after tumor establishment.

FIG. 3lb presents data on lymphproliferation of splenocytes obtained from mice immunized with Protein-D1/3-E7-His /HPV16 formulations prior to tumor challenge, wherein the splenocytes were stimulated in vitro with latex microbeads coated with Protein-D1/3-E7-His /HPV 16.

FIG. 33 presents data on E7-specific antibody titers obtained from mice immunized with Protein-D1/3-E7-His /HPV16 formulations prior to tumor challenge.

His /HPV18 formulations.

FIG. 38 presents data on E7-specific antibody titers obtained from mice immunized with Protein-D1/3-E7-His /HPV16 formulations.

Figure 2:
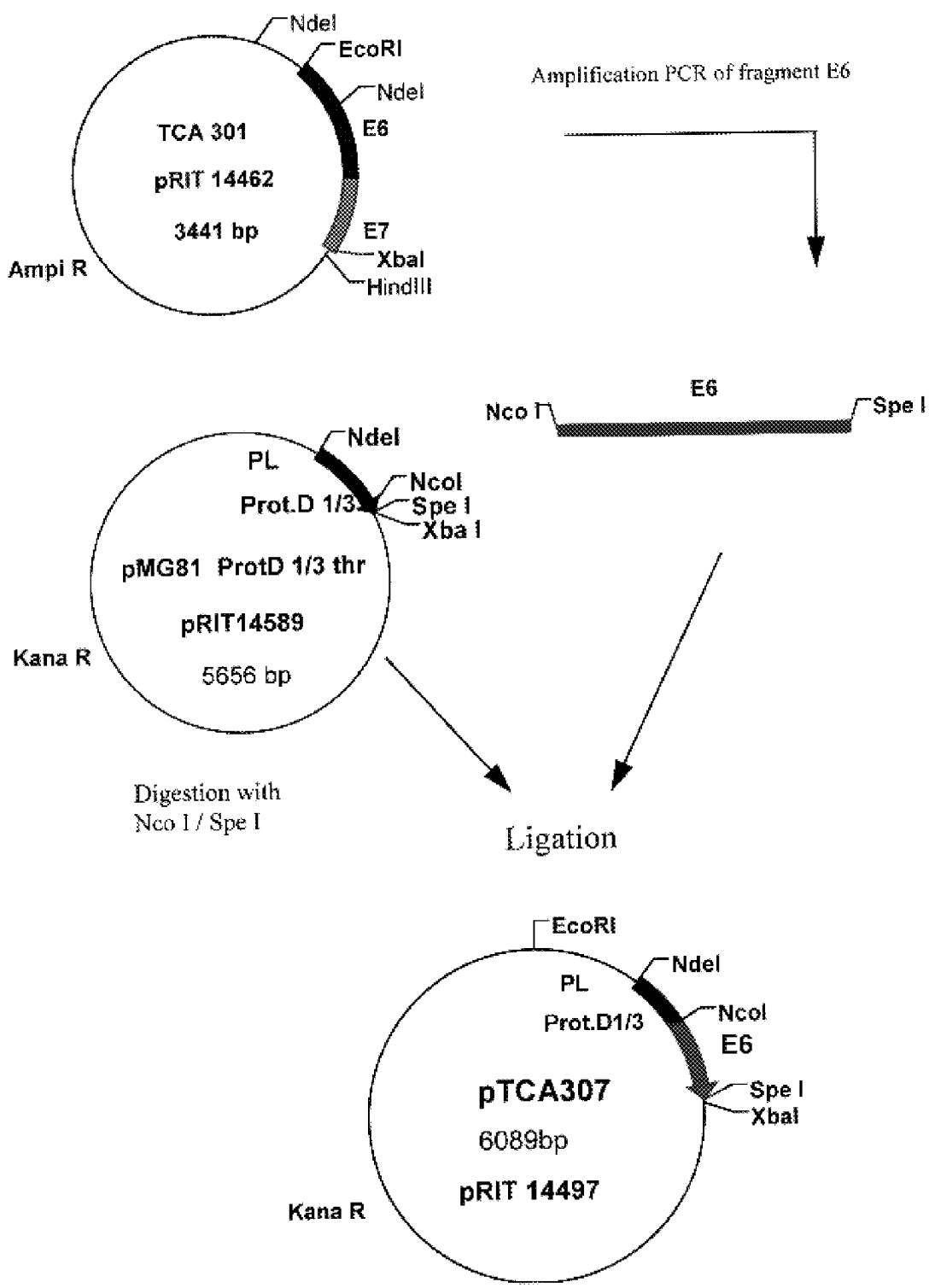
FIG. 2 is a diagram describing the construction of plasmid TCA307.

The invention will be further described by reference to the following examples:

EXAMPLE I

Construction of an *E. coli* Strain Expressing Fusion Protein-D1/3-E7-His (HPV16)

1)—Construction of Expression Plasmid a)—Plasmid pMG MCS prot D1/3 (=pRIT14589) is a derivative of pMG81 (described in UK patent application n°951 3261.9 published as WO97/01640) in which the codons 4–81 of NS1 coding region from Influenza were replaced by the iscodons corresponding to residues Ser 20→Thr127 of mature protein D of Haemophilus Influenzae strain 772, biotype 2 (H. Janson et al., 1991, Infection and Immunity, Jan. p 119–125). The sequence of Prot-D1/3 is followed by a multiple cloning site (11 residues) and a coding region for a C-terminal histidine tail (6 His). This plasmid is used to express the fusion protein D1/3-E7-His.

b)—HPV genomic E6 and E7 sequences type HPV 16 (See Dorf et al., Virology 1985, 145, p. 181–185) were amplified from HPV 16 full length genome cloned in pBR322 (obtained from Deutsches Krebsforschungszentrum (DKFZ), Referenzzentrum für human pathogen Papillomaviruses—D 69120 —Heidelberg) and were subconed into pUC19 to give TCA 301 (=pRIT14462).

Construction of Plasmid TCA 308 (=pRIT14501): a Plasmid expressing the fusion Protein-D1/3-E7-His The nucleotides sequences corresponding to amino acids 1→98 of E7 protein are amplified from pRIT14462. During the polymerase chain reaction, NcoI and SpeI restriction sites were generated at the 5' and 3' ends of the E7 sequences allowing insertion into the same sites of plasmid pMGMCS Prot D1/3 to give plasmid TCA308 (=pRIT14501). The insert was sequenced to verify that no modification had been generated during the polymerase chain reaction. The sequence for the fusion protein-D1/3-E7-His (HPV 16) is described in FIG. 1.

2)—Transformation of AR58 Strain

Plasmid pRIT14501 was introduced into *E. coli* AR58 (Mott et al., 1985, Proc. Natl. Acad. Sci., 82:88) a defective λ lysogen containing a thermosensitive repressor of the λ pL promoter.

3)—Growth and Induction of Bacterial Strain—Expression of Prot -D1/3-E7-His

Cells of AR58 transformed with plasmid pRIT14501 were grown in 100 ml of LB medium supplemented with 50 μgr/ml of Kanamycin at 30° C. During the logarithmic phase of growth bacteria were shifted to 39° C. to inactivate the λ repressor and turn on the synthesis of protein D1/3-E7-His. The incubation at 39° C. was continued for 4 hours. Bacteria were pelleted and stored at −20° C.

EXAMPLE II

Characterisation of Fusion Protein D1/3-E7-His (HPV 16)

Frozen cells are thawed and resuspended in 10 ml of PBS buffer. Cells are broken in a French pressure cell press SLM Aminco at 20.000 psi (three passages). The extract is centrifuged at 16.000 g for 30 minutes at 4° C.

After centrifugation of extracts described above, aliquots of supernatant and pellet were analysed by SDS-polyacrylamide gel electrophoresis and Western blotting. A major band of about 33 kDa, localised in the pellet fraction, was visualised by Coomassie stained gels and identified in Western blots by rabbit polyclonal anti-protein-D and by Ni-NTA conjugate coupled to calf intestinal alkaline phosphatase (Qiagen cat. n° 34510) which detects accessible histidine tail. The level of expression represents about 5 % of total protein as shown on a Coomassie-stained SDS-polyacrylamide gel.

EXAMPLE III

Protein -D1/3-E7-His (HPV 16) Purification

One liter culture of bacteria expressing protein -D1/3-E7-His, is centrifuged at 11,300 g for 30 min at 4° C. and cell pellet is kept at −80° C. until further treatment.

After resuspension in 75 ml PBS buffer, *E. coli* cells are broken in a French pressure cell press (SLM Aminco®) at 20,000 psi. Lysed cells are pelleted by centrifugation at 17,000 g for 30 minutes. Pellet, containing the protein-D1/3-E7-His, is washed once in 30 ml of 2M NaCl, 50 mM Phosphate pH 7.5, then twice in 30 ml 50 mM Phosphate pH 7.5. Proteins are solubilised after 2 hours incubation of the pellet in 30 ml of 8 M urea, 50 mM phosphate pH 7.5 at RT. Cells debris are eliminated by 15 min centrifugation at 17,000 g, 4° C. Protein purification is carried out at RT°, 15 ml of solubilised protein are applied onto a 5 ml Ni2+NTA (Qiagen) resin (Pharmacia column XK 16/20) preequilibrated in 8M urea, 50 mM phosphate pH 7.5 at a flow rate of 0.2 ml/min. The column is washed in the same buffer until the absorbance at 280 nm reaches the base line. The protein is eluted with a 0–600 mM Imidazole gradient in 8M urea, 50 mM phosphate pH 7.5. The flow rate of these two last steps is brought to 1 ml/min. Eluted fractions are analysed by SDS polyacrylamide gel electrophoresis and by Western blotting. ProtD1/3-E7-His, visualised by Coomassie blue staining, by a polyclonal anti protein D or by a monoclonal anti E7 antibody, appears as a major single band at about 32 kDalton and is estimated as a 95% pure protein. No *E. coli* contaminants, traced with a polyclonal anti *E. coli* proteins antibody, are observed.

In order to eliminate urea, 9 ml of purified antigen, at 1.33 mg/ml (Bradford), is dialysed against 3 liters of PBS buffer overnight at RT° followed by a 4 hours dialysis against a fresh PBS buffer. 80% of urea free protein is recovered as soluble protein. To eliminate contaminating endotoxins, 6 ml of dialysed protein are incubated with 1 ml of Affiprep polymixin gel (Biorad), for 3 hours at 4° C. under gentle stirring. A second incubation with 500 μl of Affiprep polymixin resin is performed to minimise the endotoxin level to 8.8 EU/μg protein. After sterile filtration on a 0.22 μm filter device (Millex 0.22 G V, Millipore), prot-D1/3-E7-His at 0.665 mg/ml is assayed for stability. SDS PAGE analysis showed no evolution of the protein after 7 days incubation at −20° C., 4° C., RT° or 37° C.

EXAMPLE IV

Construction of an *E.coli* Strain Expressing Fusion Protein-D1/3-E6-his / HPV16

1. Construction of Expression Plasmid a) Plasmid pMG MCS prot D1/3 (=pRIT14589) is a derivative of pMG81 (described in WO97/01640 in which the codons 4–81 of NS1 coding region from Influenza were replaced by the codons corresponding to residues Ser 20→Thr 127 of mature protein D of Haemophilus Influenzae strain 772, biotype 2 (H. Janson et al., 1991, Infection and Immunity, Jan. p.119–125). The sequence of Prot-D1/3 is followed by a multiple cloning site (11 residues) and a coding region for a C-terrninal histidine tail (6 His). This plasmid is used to express the fusion protein D1/3-E6-his.

b) HPV genomic E6 and E7 sequences type HPV16 (Seedorf et al., Virology 1985, 145, p.181–185) were amplified from HPV16 full length genome cloned in pBR322 (obtained from Deutsches Krebsforschungszentrum (DKFZ), Referenzzentrum für human pathogen Papillomaviruses.

c) D 69120—Heidelberg) and were subcloned into pUC19 to give TCA 301 (=pRIT14462).

Construction of Plasmid TCA 307 (=pRIT14497): a Plasmid Expressing the Fusion Protein-D1/3-E6-His /HPV16

The nucleotides sequences corresponding to amino acid. 1→151 of E6 protein were amplified from pRIT14462. During the polymerase chain reaction, NcoI and SpeI restriction sites were generated at the 5' and 3' ends of the E6 sequences allowing insertion into the same sites of plasmid pMGMCS Prot D1/3 to give plasmid TCA307 (=pRIT14497) (see FIG. 2). The insert was sequenced to verify that no modification had been generated during the polymerase chain reaction. The coding sequence for the fusion protein-D1/3-E6-His is described in FIG. 3.

2. Transformation of AR58 Strain

Plasmid pRIT14497 was introduced into *E. coli* AR58 (Mott et al., 1985, Proc. Natl. Acad. Sci., 82:88) a defective λ lysogen containing a thermosensitive repressor of the λ pL promoter.

3. Growth and Induction of Bacterial Strain—Expression of Prot-D1/3-E6-His

Cells of AR58 transformed with plasmid pRIT14497 were grown in 100 ml of LB medium supplemented with 50 μgr/ml of Kanamycin at 30° C. During the logarithmic phase of growth bacteria were shifted to 39° C. to inactivate the λ repressor and turn on the synthesis of protein D1/3-E6-his. The incubation at 39° C. was continued for 4 hours. Bacteria were pelleted and stored at −20C.

4. Characterization of Fusion Protein D1/3-E6-his (HPV 16)

Preparation of Extracts

Frozen cells are thawed and resuspended in 10 ml of PBS buffer. Cells are broken in a French pressure cell press SLM Aminco at 20.000 psi (three passages). The extract is centrifuged at 16.000 g for 30 minutes at 4° C.

Analysis on Coomassie-stained SDS-polyacrylamide Gels and Western Blots

After centrifugation of extracts described above, aliquots of supernatant and pellet were analysed by SDS-polyacrylamide gel electrophoresis and Western blotting.

A major band of about 32 kDa, localized in the pellet fraction, was visualised by Coomassie stained gels and identified in Western blots by rabbit polyclonal anti-protein-D and by Ni-NTA conjugate coupled to calf intestinal alkaline phosphatase (Qiagen cat. n° 34510) which detects accessible histidine tail. The level of expression represents about 5% of total protein.

5. Coexpression with Thioredoxin

In an analagons fashion to the expression of prot D 1/3 E7 His from HPV 18 (example XIII) an *E.coli* strain AR58 was transformed with a plasmid encoding thioredoxin and protein D 1/3 E7 His (HPV 16).

EXAMPLE V

Purification of Prot D 1/3 E6 His (HPV 16)

HPV-16 ProtD1/3 E6 recombinant antigen was expressed in *E. coli* (AR58). Expression strategy included fusion of E6 to the 1/3-N-terminal portion of protein D from Haemophilus influenzae, an immunological fusion partner providing T cell helper epitopes. An affinity polyhistidine tail was engineered at the carboxy terminus of the fusion protein. The recombinant antigen was overexpressed in *E. coli* as insoluble proteins.

Solubilisation of the antigen required denaturing agents. In absence of denaturing agent, ProtD1/3-E6His precipitated at neutral pH. To circumvent the solubility problems, co-expression of these proteins with Thioredoxin in Trans (TIT), a folding partner was carried out.

Bacterial expressions are conducted in LB media in presence of 0.05 mg/ml of kanamycin at 30° C. plus 0.2 mg/ml of Ampicillin when Thioredoxin is coexpressed. Recombinant protein expression is thermally induced by transferring the cells to 42° C., when cell optical density (OD$_{600\ nm}$) of 0.4 is reached. Protein expression is maintained for 4 hours. Purification was carried out according to the following protocol.

| | |
|---|---|
| Cell Culture | 60 OD$_{600}$ |
| Pellet | 1 mM pefabloc, 2M NaCl, PBS pH 7.4 (Buffer A) |
| French Press Disruptor | Three passes 20,000 psi |
| Centrifugation | 17,000 g 30 min, 4° C. |
| Pellet Washes | 2M NaCl, PBS pH 7.4 (Buffer B) x1 PBS pH 7.4 (Buffer C) x2 |
| Centrifugation | 17,000 g 30 min, 4° C. |
| Pellet Solubilisation | 6 M Guanidine Chloride, 20 mM PO4, pH 7.0 (Buffer D) Overnight at 4° C. |
| Centrifugation | 17,000 g 30 min, 4° C. |
| Supernatant on IMAC | Equilibration: 6 M Guanidine Chloride, 20 mM PO4, pH 7.0 (Buffer D) Elution: Imidazole steps (0.025M, 0.1M, 0.5M) in 8M Urea, 20 mM PO4, pH 7.O |
| Affiprep Polymyxin | 8M Urea, 20 mM PO, pH 7.0 (Buffer E) 2h RT° |
| Dialysis | 4M Urea, 0.5 M Arginine, 150 mM NaCl, 10 mM PO4, pH 6.8 (Buffer I) 2M Urea, 0.5 M Arginine, 150 mM NaCl, 10 mM PO4 pH 6.8, (Buffer J) 0M Urea, 0.5 M Arginine, 150 mM NaCl, 10 mM PO4 pH 6.8 (Buffer K) |

Cells are efficiently broken by high-pressure homogenisation using a French pressure cell device. Antigen is extracted with high concentration of protein denaturant. This first step breaks open the bacterial cell wall and antigen is extracted from the bacterial insoluble fraction. The following purification was carried out on 4 liter culture.

Buffers

A. PBS/2M NaCl/1 mM Pefabloc

B. PBS/2 M NaCl

C. PBS: 137 mM NaCl, 2.7 mM KCl, 8.1 mM NaH2PO4, 1.47 mM KH2PO4 pH 7.4.

D. 6 M Guanidium Chloride, 20 mM PO4 (NaH2PO4 (2 H2O)/K2HPO4 (3 H2O)) pH7.0

Starting material is 10 flasks of 400 ml culture each.

Cell paste is suspended to 60 OD$_{600}$ in Buffer A (240 ml of Buffer A in this case), prior cell lysis by three passes through a French press disrupter (20,000 psi). Lysed cells are pelleted 30 min at 15,000 g at 4° C. Bacterial cell pellet containing the recombinant protein is washed once in 240 ml Buffer B, then twice in 240 ml Buffer C.

Prot D E6-His (TIT) is solubilised by 240 ml Buffer D overnight at 4° C. on a rotating wheel. Cell debris are pelleted 30 min at 15,000 g at 4° C. Supernatant (230 ml) is stored at −20° C. The material is then subjected to IMAC chromatography.

The chelating ligand NTA (nitrilo-tri-acetic-acid) is attached to an Agarose support (Qiagen). NTA ligand is charged with nickel metal ion with which it interacts through 4 of the 6 coordination sites of the nickel. The two remaining coordination sites of nickel interact strongly with histidine residues of the 6×His-tagged protein. Elution is achieved by competition with Imidazole which bind to the Ni-NTA and displace the tagged antigen.

Ni-NTA Agarose Qiagen (catalogue number: 30 250) was used.

Solutions

D: 6 M Guanidium Chloride, 20 mM PO4 (NaH$_2$PO4 (2H$_2$O)/K$_2$HPO4 (3H2O)), pH 7.0

E: 8M Urea, 20 mM PO4 (NaH$_2$PO4 (2H$_2$O)/K$_2$HPO4 (3H$_2$O)), pH 7.0

F: E+0.025 M Imidazole

G: E+0.1 M Imidazole

H: E+0.5 M Imidazole 0.5 M NaOH

Deionized Water 0.02% NaN$_3$

Purification a) The resin (15 ml resin/230 ml sample) is packed and equilibrated in 10 column volumes (C.V.) of Buffer D at 15 cm h$^{-1}$.

b) Supernatant from solubilised fraction is injected onto the column at 15 cm h$^{-1}$.

c) Column is washed at 15 cm h$^{-1}$ with buffer D until OD 280 nm returns to the baseline.

d) Column is washed with 2 CV of Buffer E at 15 cm h$^{-1}$. The wash fraction is recovered.

e) Column is first eluted with 5 CV of Buffer F. Elimination of 25 kD major contaminant.

f) Column is then eluted with 2 CV of Buffer G.

g) Column is finally eluted with 3 CV of Buffer H. Elution of the antigen.

Antigen positive fractions are pooled (30 ml).

Endotoxin is removed by affiprep chromatography. Affi-Prep® Polymyxin support consists of USP Grade Polymyxin B coupled to the Affi-Prep® Matrix. Due to its high affinity to the lipid A moiety of endotoxins, polymixin B binds endotoxin molecules with high capacity and selectivity.

Solutions

E: 8M Urea, 20 mM PO4 (NaH$_2$PO4(2H$_2$O)/K$_2$HPO4 (3H$_2$O)), pH 7.0 (apyrogenic).

0.5 M Na OH

Deionized Apyrogenic Water

Procedure

1) Affi-Prep® Polymyxin resin is washed in 10 volumes of 0.1 M NaOH, followed by 10 volumes of pyrogen free water.

2) Resin is equilibrated in 10 volumes of Buffer E.

3) 15 ml (half-pool) of IMAC-eluted sample is incubated with 3 ml of Affi-Prep® Polymyxin resin in a batch mode.

4) Incubation is pursued 4 hours at Room Temperature or O/N at 4° C. on a rotating wheel.

5) Sample is centrifuged 10 min at 2000 g (Beckman GS-6R).

6) Supernatant containing the antigen is collected and submitted to endotoxins and protein assays.

7) Resin is discarded.

Small molecules diffuse through a semi-permeable membrane while large molecules are retained. The process of dialysis is driven by the difference in concentration of the solutes on the two sides of the membrane. New buffer solution is introduced until buffer composition on each side equalises.

Buffers

I: 4M Urea, 0.5 M Arginine, 0.15M NaCl; 10 mM PO4 (NaH$_2$PO4 (2H$_2$O)/K$_2$HPO4 (3H$_2$O)) pH 6.8

J: 2M Urea, 0.5 M Arginine, 0.15M NaCl, 10 mM PO4 (NaH$_2$PO4 (2H$_2$O)/K$_2$HPO4 (3H$_2$O)) pH 6.8

K: 0M Urea, 0.5 M Arginine, 0.15M NaCl, 10 mM PO4 (NaH$_2$PO4 (2H$_2$O)/K$_2$HPO4 (3H$_2$O)) pH 6.8

1) The Sample (15 ml) is introduced into a dialysis tubing (20.4 mm diameter and 6 cm height).

2) Dialysis tubing is placed in a 2 liters cylinder containing Buffer I under stirring at 4° C. for 2 hours.

3) Dialysis tubing is placed in a 2 liters cylinder (under stirring) containing Buffer J; at 4° C. for 2 hours.

4) Dialysis tubing is placed in a 2 liters cylinder containing Buffer K (under stirring) at 4° C. O/N. Buffer is changed and dialysis is pursued 2 more hours at 4° C.

Millipore Sterile Millex-GV 0.22$\mu$,13 mm. Catalogue number: SLGV0130S.

All steps are performed at room temperature (RT~22° C.), the antigen appears stable.

Antigen solution is filtered through a 0.2 $\mu$m filter to prevent any bacterial growth. Antigen is kept at −20° C. in Nunc vials.

Characterisation

Protein D1/3 E6 His is characterised as follows:

ProteinD1/3 -E6-His is a 273 amino acids long peptide with 112 amino acids coming from Protein D part. ProteinD1/3-E6-His has a theoretical Molecular Weight of 32 kD and migrates on SDS-PAGE as a 33 kD protein. ProteinD1/3-E6-His theoretical isoelectric point is 8.17.

The viral Protein E6 is a basic protein containing 14 cystein residues, eight of them (Cys 30,33,63,66 and Cys 103,106,136,139) are involved in two C-terminal zinc binding motifs.

Protein D 1/3-E6-His is expressed as insoluble protein, in E. coli-AR 58 strain, with Thioredoxin in Trans, a folding partner. Cell culture is produced in 400 ml flask.

5.4 mg of 95% pure protein is obtained per liter of culture.

EXAMPLE VI

Construction of an *E. coli* Strain Expressing Fusion Protein-D1/3-E6E7-his/HPV16

1. Construction of Expression Plasmid a) Plasmid pMG MCS prot D1/3 (=pRIT14589) is a derivative of pMG81 (described Supra) in which the codons 4–81 of NS1 coding region from Influenza were replaced by the codons corresponding to residues Ser 20→Thr 127 of mature protein D of Haemophilus Influenzae strain 772, biotype 2 (H. Janson et al., 1991, Infection and Immunity, Jan. p.119–125). The sequence of Prot-D1/3 is followed by a multiple cloning site (11 residues) and a coding region for a C-terminal histidine tail (6 His). This plasmid is used to express the fusion protein D1/3-E6E7-his.

b) HPV genomic E6 and E7 sequences type HPV16 (Seedorf et al, Virology 1985, 145, p.181–185) were amplified from HPV16 full length genome cloned in pBR322 (obtained from Deutsches Krebsforschungszentrum (DKFZ), Referenzzentrum für human pathogen Papillomaviruses - D 69120 - Heidelberg) and were subcloned into pUC19 to give TCA 301 (=pRIT14462).

c) The coding sequences for E6 and E7 in TCA301 (=pRIT 14462) were modified with a synthetic oligonucleotides adaptor (inserted between Afl III and Nsi I sites) introducing a deletion of 5 nucleotides between E6 and E7 genes to remove the stop codon of E6 and create fused E6 and E7 coding sequences in the plasmid TCA309(=pRIT 14556 ) see FIG. 4.

Construction of Plasmid TCA 311(=pRIT14512): a Plasmid Expressing the Fusion Protein-D1/3-E6E7-His /HPV16

Figure 5:
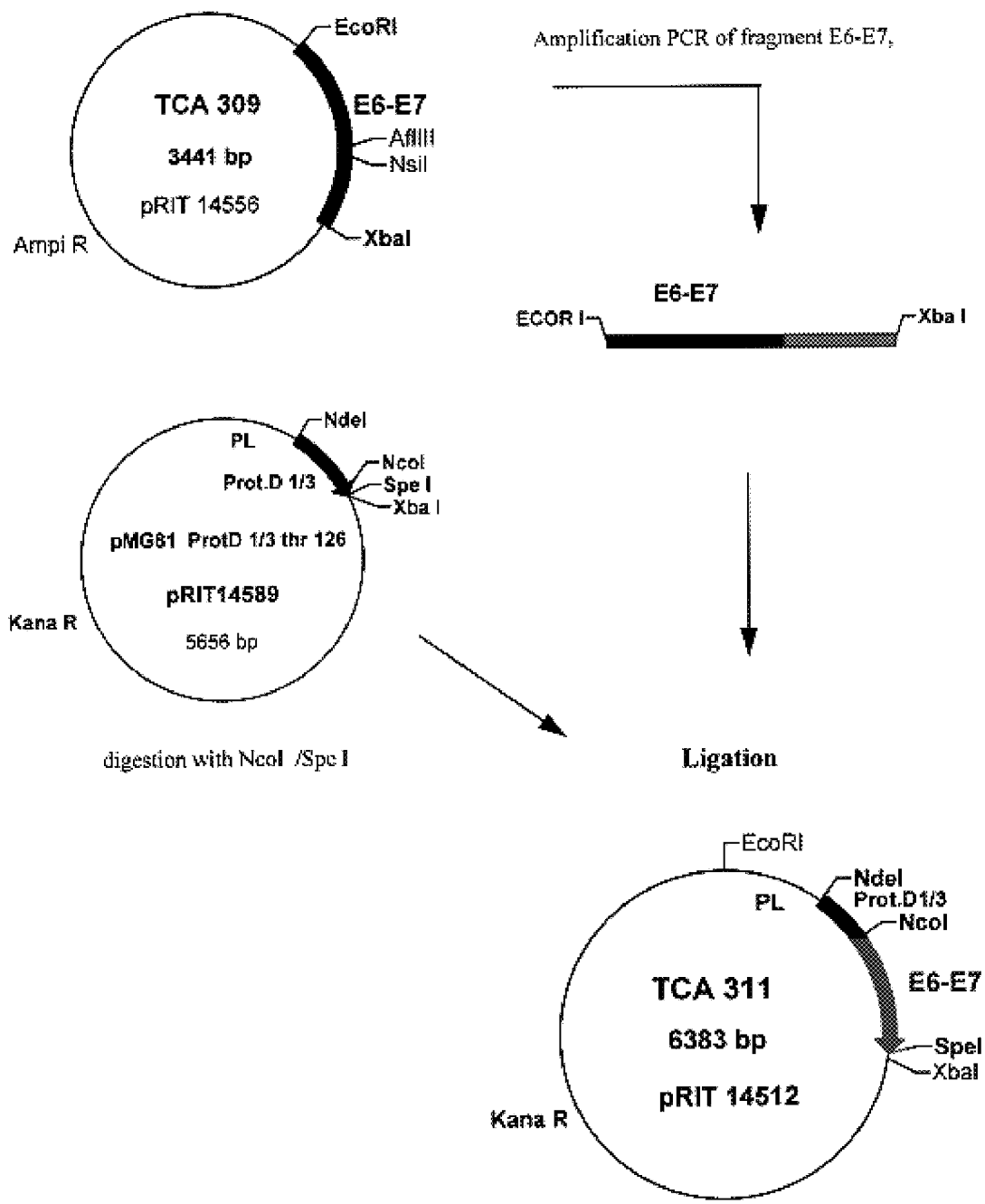
FIG. 5 is a diagram describing the construction of plasmid TCA3 11.
Figure 7:
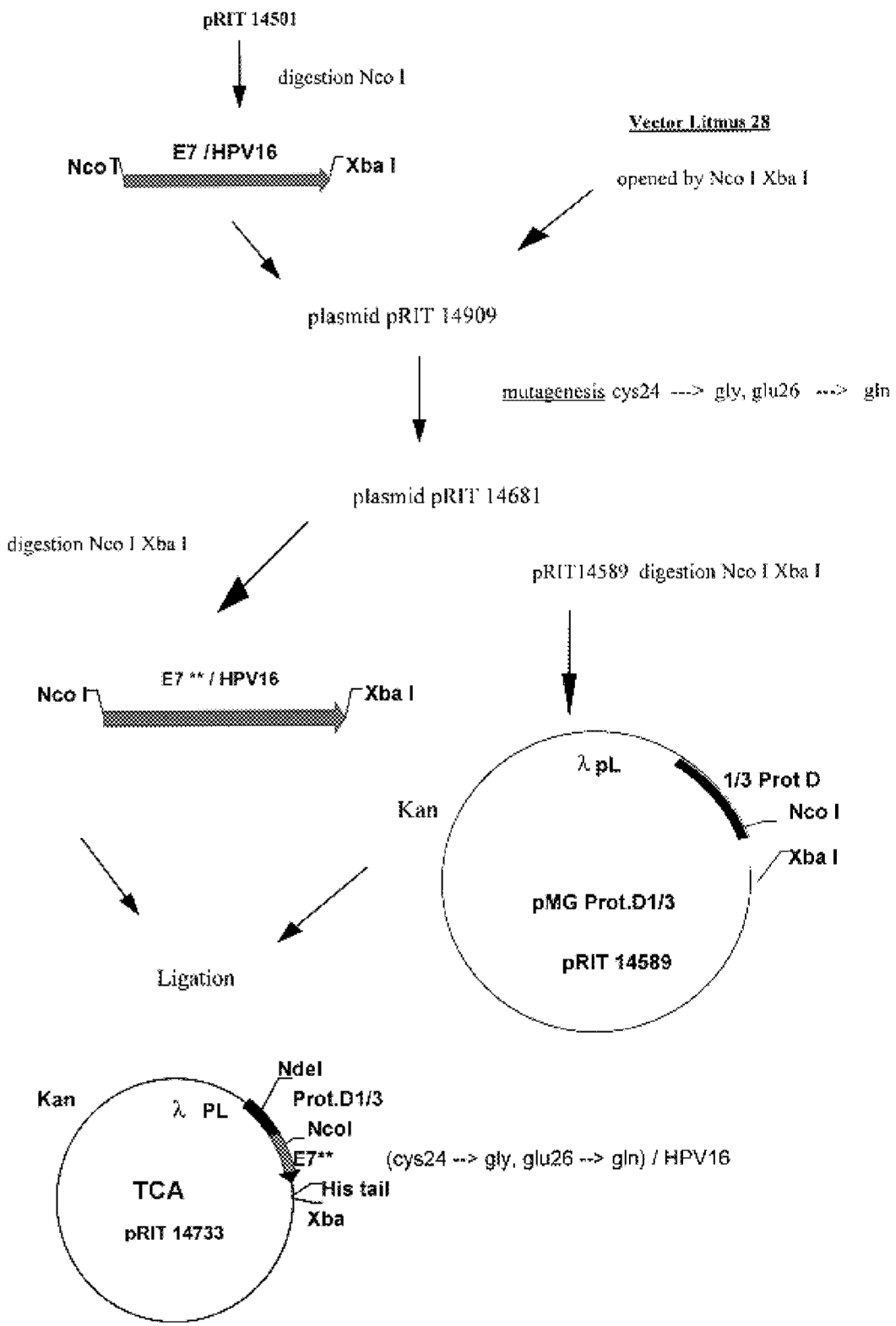
FIG. 7 is a diagram describing the construction of plasmid TCA347.

The nucleotides sequences corresponding to amino acids 1→249 of fused E6E7 protein were amplified from pRIT14556. During the polymerase chain reaction, NcoI and SpeI restriction sites were generated at the 5' and 3' ends of the E6E7 fused sequences allowing insertion into the same sites of plasmid pMGMCS Prot D1/3 to give plasmid TCA311 (=pRIT14512) (see FIG. 5). The insert was sequenced to verify that no modification had been generated during the polymerase chain reaction. The coding sequence for the fusion protein-D1/3-His is described FIG. 6.

2. Transformation of AR58 Strain

Plasmid pRIT14512 was introduced into *E. coli* AR58 (Mott et al., 1985, Proc. Natl. Acad. Sci., 82:88) a defective λ lysogen containing a thermosensitive repressor of the λ pL promoter.

3. Growth and Induction of Bacterial Strain—Expression of Prot-D1/3-E6E7-His

Cells of AR58 transformed with plasmid pRIT14512 were grown in 100 ml of LB medium supplemented with 50 μgr/ml of Kanamycin at 30° C. During the logarithmic phase of growth bacteria were shifted to 39° C. to inactivate the λ repressor and turn on the synthesis of protein D1/3-E6E7-his. The incubation at 39° C. was continued for 4 hours. Bacteria were pelleted and stored at −20C.

4. Characterization of Fusion Protein D1/3-E6E7-his

Frozen cells are thawed and resuspended in 10 ml of PBS buffer. Cells are broken in a French pressure cell press SLM Aminco at 20,000 psi (three passages). The extract is centrifuged at 16,000 g for 30 minutes at 4° C.

After centrifugation of extracts described above, aliquots of supernatant and pellet were analysed by SDS-polyacrylamide gel electrophoresis and Western blotting.

A major band of about 48 kDa, localized in the pellet fraction, was visualised by Coomassie stained gels and identified in Western blots by rabbit polyclonal anti-protein-D and by Ni-NTA conjugate coupled to calf intestinal alkaline phosphatase (Qiagen cat. n° 34510) which detects accessible histidine tail. The level of expression represents about 1% of total protein.

EXAMPLE: VIb

In an analagous fashion the fusion protein of Lipo D 1/3 and E6–E7 from HPV16 was expressed in *E. coli* in the presence of thioredoxin. The N-terminal of the pre-protein (388 aa) contains MDP residues followed by 16 amino acids of signal peptide of lipoprotein D (from Haemophilus Influenzae) which is cleaved in vivo to give the mature protein (370 aa). Lipoprotein portion (aa 1 to 127) is followed by the proteins E6 and E7 in fusion. The C terminal of the protein is elongated by TSGHHHHHH.

The protein was purified by the following protocol:

EXAMPLE VII

Lipoprotein D1/3-E6-E7-His (TIT) Purification

A) Solubilisation.

Cell paste is suspended to 60 $OD_{600}$ in 2 M NaCl, 20 mM Phosphate ($NaH_2PO_4/K_2HPO_4$) pH 7.5 in presence of 1 mM Pefabloc as protease inhibitor prior cell lysis by three passes through a French press disruptor (20,000 psi). Lysed cells are pelleted 30 min at 15,000 g at 4° C. In order to reduce endotoxin level, bacterial cell pellet containing the recombinant protein is washed twice in 4 M urea, 2 M NaCl, 20 mM Phosphate pH 7.5, once in 2% Empigen BB, 20 mM Phosphate pH 7.5 and finally twice in 20 mM Phosphate buffer pH 7.0 to eliminate trace of detergent (each wash is performed in the same volume used for cell suspension). LipoProt. D1/3-E6-E7-His (TIT) is solubilised (in the same volume used for cell suspension) by 8 M urea in 0.2 M βMercaptoEthanol (=βMeOH), 20 mM PO4 pH 12 overnight at 4 ° C. followed by a two hours incubation at RT° versus the same buffer. Cell debris are pelleted 30 min at 15,000 g at 4° C. Supernatant is kept at −20° C.

B) Purification

1) Anion Exchange Chromatography on Q-Sepharose Fast Flow.

225 ml of frozen sample is thawed at room temperature in a cold water bath and is applied onto a Q-Sepharose fast flow column (Pharmacia, XK 26/20) preequilibrated in 8 M urea, 0.2 M βMEOH, 20 mM PO4 pH 12 (30 ml resin/225 ml supernatant) at 45 cm/h. Column is washed by 8 M urea, 0.2 M βMEOH, 20 mM PO4 pH 12, until OD 280 nm reaches the baseline, followed by a second wash in 8 M urea, 20 mM Phosphate pH 12 (in 2 column volumes) Elution is performed by NaCl steps (0.1 M, 0.25 M, 0.5 M NaCl, each step in about 2 column volumes) in 8 M urea, 20 mM Phosphate pH 12, at 45 cm/h. 0.5 M NaCl-eluted fractions are pooled.

2) Ion Metal Affinity Chromatography (IMAC).

0.5 M NaCl-eluted fractions from Q Sepharose step are pooled and dialyzed versus 0.2 M NaCl, 8 M urea, 20 mM Phosphate pH 10 before loading onto a Ni2+-NTA (Qiagen) column (XK 26/20, Pharmacia) preequilibrated in 8 M urea, 20 mM PO4 pH 12 (30 ml resin/61 ml sample) at 5.6 cm/h. Column is washed in 8 M urea, 20 mM PO4 pH 12 until the base line is reached then by 8 M urea, 20 mM PO4 pH 10. Antigen is eluted by Imidazole steps (0.025 M, 0.05 M, 0.1 M, 0.15 M, 0.2 M, 0.5 M Imidazole, each step in two column volumes) in 8 M urea, 20 mM PO4 pH 10, at 45 cm/h. 0.05 M Imidazole-eluted fractions are pooled.

C) Concentration.

Imac sample is concentrated about 5 times (to 0.407 mg/ml) on a 5 kDa Filtron Omega membrane in a stirred cell from AMICON at RT°.

D) Dialysis

Concentrated sample is dialyzed at RT versus decreasing-urea-concentration steps (4 M, 2 M urea) in 0.5 M Arginine, 150 mM NaCl, 10 mM PO4 pH 6.8. Last dialysis against 0.5 M Arginine, 150 mM NaCl, 10 mM PO4 pH 6.8 is achieved at 4° C.

Results

IMAC step is able to eliminate a 32 kD contaminant at 0.025 M Imidazole which eluted also some antigen. 0.05 M Imidazole-eluted Antigen is estimated pure at 90% by Coomassie blue staining of SDS-PAGE . After these two purification steps, sample is free of *E. coli* contaminants. Western blotting analysis using specific antigen-N and/or C terminus antibodies shows a heterogeneous pattern of bands with higher and lower MW than the full length protein. This pattern suggests the presence of aggregates and incompletely processed protein and/or degraded one, copurified with the full length protein.

EXAMPLE VIII

Construction of *E.coli* Strain B1002 Expressing Fusion ProtD1/3-E7 Mutated (cys24→gly, glu26→gln ) type HPV16

1)—Construction of Expression Plasmid

Starting Material a)—Plasmid pRIT 14501 (=TCA 308) which codes for fusion ProtD1/3-E7 -His b)—Plasmid LITMUS 28 (New England Biolabs cat n°306–28 ), a cloning vector pUC-derived c)—Plasmid pMG MCS ProtD1/3 (pRIT 14589), a derivative of pMG81 (described Supra) in which the codons 4–81 of NS1 coding region from Influenza were replaced by the codons corresponding to residues Ser 20→Thr 127 of mature protein D of Ha Guanidine hydrochloride 8M buffer (concentration L$^{-1}$ Gu.HCl 764 g;

Empigen 30% 3.33 mL , PO$_4^{3-}$0.5M 40 mL) pH 7.5 recovery of the protein: Collection of the permeate—sample P3 during

Concentration to initial volume (300 mL) and

Diafiltration with 3 volume of Guanidine hydrochloride 4M buffer (concentration L$^{-1}$: Gu.HCl 328.12 g, Empigen (30%) 3.33 mL PO$_4^{3-}$0.5M 40.00 mL) pH 7.5.

All these steps are made in a cold room (2–8° C.), pH adjusted with 0.5M PO$_4^{3-}$.

The P3 fraction is store at –20° C. waiting for the next purification step.

2b) Zn-Chelating Sepharose Chromatography

The P3 fraction is thawed and injected in a packed and equilibrated Zn-chelating sepharose FF.

After that, the column is:

Washed with around 3 volumes of Guanidine hydrochloride 4M buffer (see above)—sample Zn-FT Washed with around 5 volumes of Urea 4M buffer (concentration L$^{-1}$: Urea 240.24 g Empigen 3.33 mL PO$_4^{3-}$ 0.5M 40.00 mL)—sample Zn-W Eluted with around 3volumes of Urea 4M-Imidazole 20 mM buffer (concentration L$^{-1}$ Urea 240.24 g, Empigen (30%) 3.33 mL Imidazole (1.36 g) PO$_4^{3-}$0.5M 40.00 mL pH 7.5) buffer as above, but concentration L$^{-1}$ of Imidazole 34.04 g—sample Zn-20

Eluted with Urea 4M-Imidazole 500 mM to the end of the UV peak—sample Zn-500

The column is the washed with EDTA 5 mM and NaOH 0.5M.

Zn chelating sepharose eluate (Zn-500) is stored between 2–8° c. before the next purification step.

The Zn-chelating sepharose chromatography operations are carried out at room temperature.

2c) Q-Sepharose Chromatography

The Zn-500 fraction is injected in a packed and equilibrated Q-sepharose FF.

After that, the column is:

Washed with around 7 volumes of Urea 4M buffer (see above)—sample QS-FT

Washed with around 10 volumes of Urea 4M buffer without empigen (concentration L$^{-1}$ Urea 240.24 g PO$_4^{3-}$ 0.5M 40.00 mL)—sample QS-WI Washed with around 10 volumes of Urea 6M buffer without empigen (Urea 360.36 g/L)—sample QS-W2

Eluted with around 5 volumes of Urea 6M-NaCl 200 mM buffer (concentration L$^{-1}$: Urea 360.36 g NaCl 11.69 g, 40.00 mL PO$_4^{3-}$.

Eluted with around 3 volumes of Urea 6M-NaCl 500 mM buffer (as above, but NaCl 29.22 g/L). The exact end of the fraction is determined by the end of the UV peak.—sample QS-500

Eluted with 4 volumes of Urea 4M-NaCl 1M buffer (concentration L$^{-1}$ Urea 360.36, NaCl 58.44 g 40.00 mL PO$_4^{3-}$(0.5)—sample QS-1M The column is then washed with NaOH 0.5M QS-sepharose eluate (QS-500) is stored between 2–8°c before the next purification step.

The Q-sepharose chromatography operations are carried out at room temperature.

2d) Ultrafiltration

The QS-500 fraction is then treated on a 10 kD ultrafiltration unit (Ultrasette—Pall Filtron)

The product is first concentrated to around 1 mg /mL of protein and then diafiltrated against 10 volumes of phosphate buffer.

The permeate (fraction UF-P) is discarded and the retentate (fraction UF-R) is stored at 2–8°c waiting for final filtration.

Ultrafiltration operations are carried out at 2–8° C.

2e) Final Filtration

The final bulk (UF-R fraction) is filtered through a 0.22 µm sterile filter (Millipak-Millipore) under laminar flow and in an aseptic class 100 room.

The final concentration is between 0.5 and 1.0 µg/mL.

The sterile bulk is stored at –20° C.

EXAMPLE X

Construction of an *E. coli* Strain Expressing Fusion Clyta-E6-his (HPV 16)

1. Construction of Expression Plasmid a)—Plasmid pRIT14497 (=TCA307), that codes for fusion ProtD1/3-E6-His/HPV16 b)—Plasmid pRIT14661 (=DVA2), an intermediate vector containing the coding sequence for the 117 C-terminal codons of LytA of *Streptococcus Pneumoniae*. Lyta is derived from *Streptococcus pneumoniae* which synthesize an N-acetyl-L-alanine amidase, amidase LYTA, (coded by the lytA gene {Gene, 43 (1986) pag 265–272} an autolysin that specifically degrades certain bonds in the peptidoglycan backbone. The C-terminal domain of the LYTA protein is responsible for the affinity to the choline or to some choline analogues such as DEAE.

Figure 9:
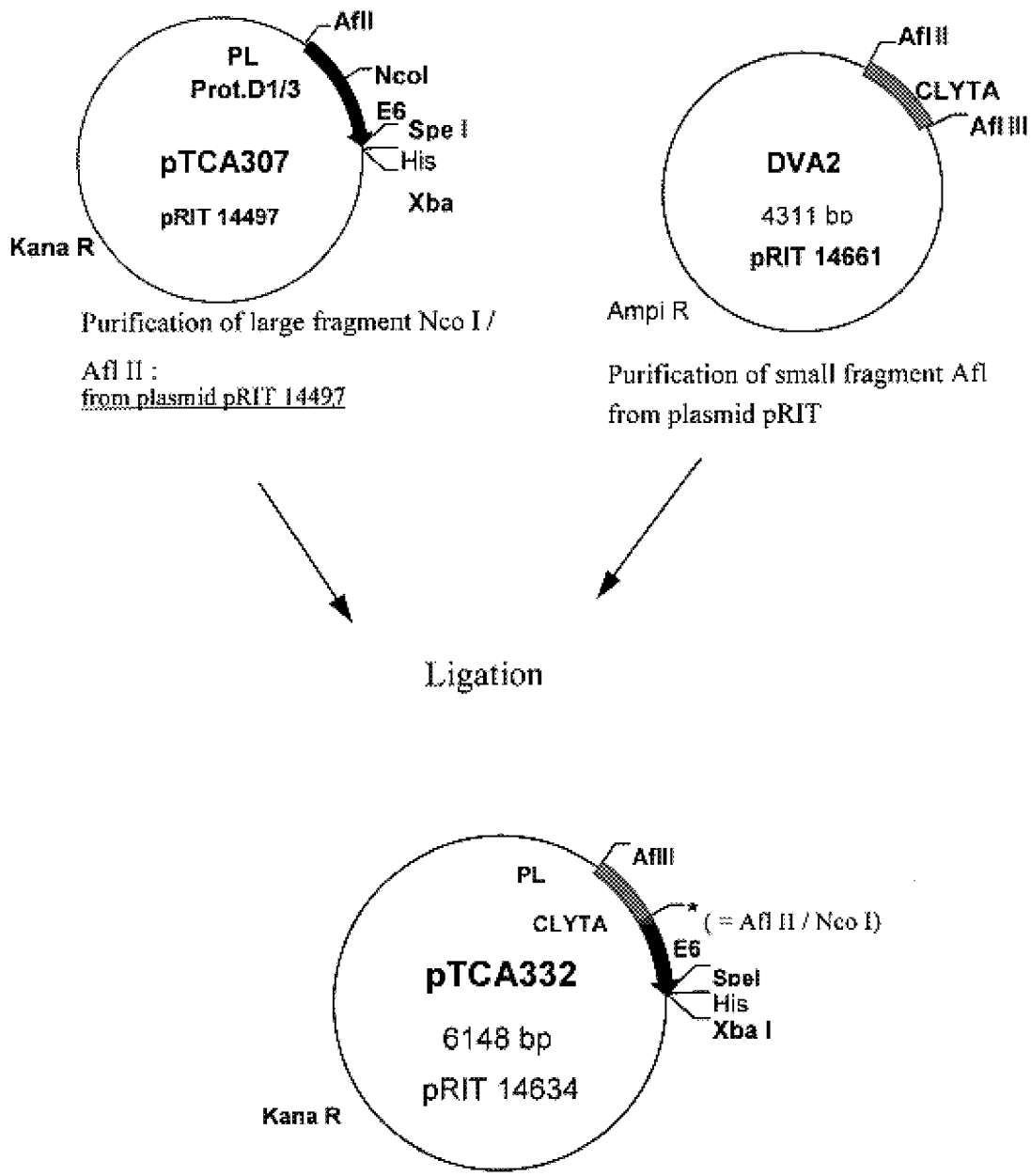
FIG. 9 is a diagram describing the construction of plasmid TCA332.

1.b Construction of Plasmid pRIT14634 (=TCA332): a Plasmid Expressing the Fusion Clyta-E6His/HPV16 a) The first step was the purification of the large NcoI-AflII restriction fragment from plasmid pRIT14497 and the purification of the small AflII-AflIII restriction fragment from pRIT14661 b) The second step was linking of clyta sequences to the E7-His sequences (NcoI and AflIII are compatible restriction sites) that gave rise to the plasmid pRIT 14634 (=TCA332), coding for the fusion protein clyta-E6-His under the control of the pL promoter. (see FIG. 9)

The coding sequence for the fusion protein clyta-E6-His is described in FIG. 10.

Transformation of AR58 Strain

Plasmid pRIT14634 was introduced into *E. coli* AR58 (Mott et al., 1985, Proc. Natl. Acad. Sci., 82:88) a defective λ lysogen containing a thermosensitive repressor of the λ pL promoter.

Growth and Induction of Bacterial Strain—Expression of Clyta-E6-His

Cells of AR58 transformed with plasmid pRIT14634 were grown in 100 ml of LB medium supplemented with 50 µgr/ml of Kanamycin at 30° C. During the logarithmic phase of growth bacteria were shifted to 39° C. to inactivate the λ repressor and turn on the synthesis of protein clyta-E6-his. The incubation at 39° C. was continued for 4 hours. Bacteria were pelleted and stored at –20° C.

Characterization of Fusion Clyta-E6-his

Frozen cells were thawed and resuspended in 10 ml of PBS buffer. Cells were broken in a French pressure cell press SLM Aminco at 20,000 psi (three passages). The extract was centrifuged at 16,000 g for 30 minutes at 4° C. After centrifugation of extracts described above, aliquots of supernatant and pellet were analysed by SDS-polyacrylamide gel electrophoresis and Western blotting.

A major band of about 33 kDa, localized in the pellet fraction, was visualised by Coomassie stained gels and identified in Western blots by rabbit polyclonal anti-clyta antibodies and by Ni-NTA conjugate coupled to calf intestinal alkaline phosphatase Plasmid pRIT14629 was introduced into *E. coli* AR58 (Mott et al., 1985, Proc. Natl. Acad. Sci., 82:88) a defective λ lysogen containing a thermosensitive repressor of the λ pL promoter.

3. Growth and Induction of Bacterial Strain—Expression of clyta-E6E7-His

Cells of AR58 transformed with plasmid pRIT14629 were grown in 100 ml of LB medium supplemented with 50 µgr/ml of Kanamycin at 30° C. During the logarithmic phase of growth bacteria were shifted to 39° C. to inactivate the λ repressor and turn on the synthesis of protein clyta-E6E7-his. The incubation at 39° C. was continued for 4 hours. Bacteria were pelleted and stored at −20° C.

Characterization of Fusion Clyta-E6E7-his

Frozen cells were thawed and resuspended in 10 ml of PBS buffer. Cells were broken in a French pressure cell press SLM Aminco at 20,000 psi (three passages). The extract was centrifuged at 16,000 g for 30 minutes at 4° C.

After centrifugation of extracts described above, aliquots of supernatant and pellet were analysed by SDS-polyacrylamide gel electrophoresis and Western blotting.

A major band of about 48 kDa, localized in the pellet fraction, was visualised by Coomassie stained gels and identified in Western blots by rabbit polyclonal anti-clyta antibodies and by Ni-NTA conjugate coupled to calf intestinal alkaline phosphatase (Qiagen cat n° 34510) which detects accessible histidine tail. The level of expression represents about 1% of total protein.

EXAMPLE XIII

Prot D1/3 E7 his (HPV 18) (*E.Coli* B1011) Protein D1/3 E7 His HPV Expressed with Thioredoxin inTrans (*E.Coli* B1012)

1)—Construction of Expression Plasmids

1).a. Construction of Plasmid TCA316(=pRIT 14532) a Plasmid Expressing the Fusion Protein-D1/3-E7-His/HPV18

Starting Materials a)—Plasmid pMG MCS prot D1/3 (=pRIT14589) is a derivative of pMG81 (described in UK patent application n° 951 3261.9 published as WO97/01640 in which the codons 4–81 of NS1 coding region from Influenza were replaced by the codons corresponding to residues Ser 20→Thr 127 of mature protein D of Haemophilus Influenzae strain 772, biotype 2 (H. Janson et al., 1991, Infection and Frozen cells were thawed and resuspended in 10 ml of PBS buffer. Cells were broken in a French pressure cell press SLM Aminco at 20,000 psi (three passages). The extract was centrifuged at 16,000 g for 30 minutes at 4° C. After centrifugation of extracts described above, aliquots of supernatant and pellet were analysed by SDS-polyacrylamide gel electrophoresis and Western blotting.

A major band of about 35 kDa, localized in the pellet fraction, was visualised by Coomassie stained gels and identified in Western blots by rabbit polyclonal anti-clyta antibodies and by Ni-NTA conjugate coupled to calf intestinal alkaline phosphatase (Qiagen cat. n° 34510) which detects accessible histidine tail. The level of expression represents about 5% of total protein.

EXAMPLE XII

Construction of an *E. coli* Strain Expressing Fusion Clyta-E6E7-his (HPV 16)

1. Construction of Expression Plasmid 1.a Starting Materials a)—Plasmid pRIT14512 (=TCA311), that codes for fusion ProtD1/3-E6E7-His/HPV 16 b)—Plasmid pRIT14661 (=DVA2), an intermediate vector containing the coding sequence for the 117 C-terminal codons of LytA of *Streptococcus Pneumoniae*.

Figure 13:
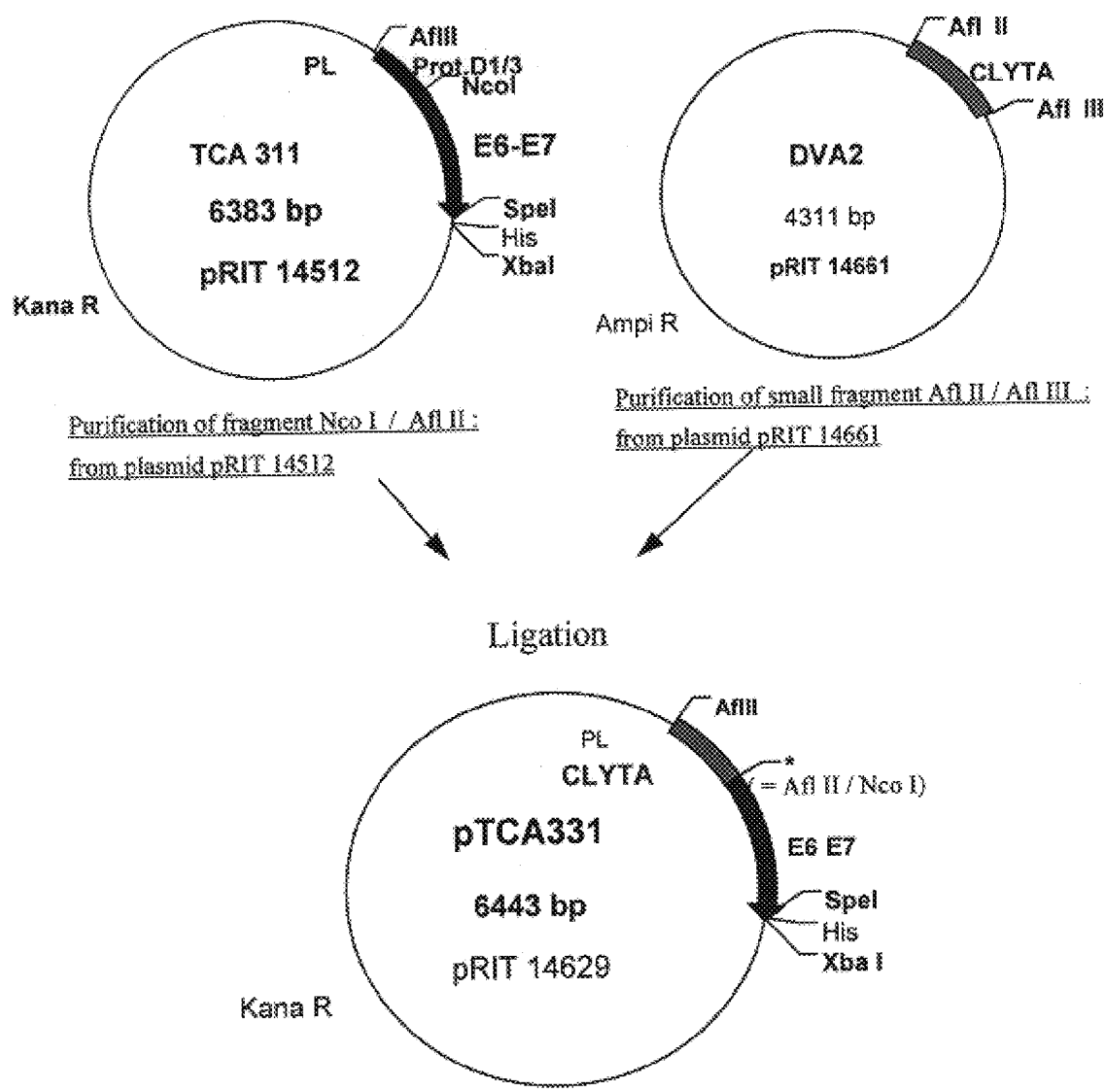
FIG. 13 is a diagram describing the construction of plasmid TCA331.

1.b Construction of Plasmid pRIT14629 (=TCA331): a Plasmid Expressing the Fusion Clyta-E6E7-His/HPV16 a) The first step was the purification of the large NcoI-AflII restriction fragment from plasmid pRIT14512 and the purification of the small AflII-AflIII restriction fragment from pRIT14661 b) The second step was linking of clyta sequences to the E7-His sequences (NcoI and AflIII are compatible restriction sites) that gave rise to the plasmid pRIT 14629 (=TCA331), coding for the fusion protein clyta-E6E7-His under the control of the pL promoter. (see FIG. 13)

The coding sequence for the fusion protein clyta-E6E7-His is described in FIG. 14.

2. Transformation of AR58 Strain (Qiagen cat. n° 34510) which detects accessible histidine tail. The level of expression represents about 3% of total protein

EXAMPLE XI

Construction of an *E. coli* Strain Expressing Fusion Clyta-E7-his (HPV 16)

1. Construction of Expression Plasmid 1.a Starting Materials a)—Plasmid pRIT14501 (=TCA308), that codes for fusion ProtD1/3-E7-His/HPV16 b)—Plasmid pRIT14661 (=DVA2), an intermediate vector containing the coding sequence for the 117 C-terminal codons of LytA of *Streptococcus Pneumoniae*.

Figure 11:
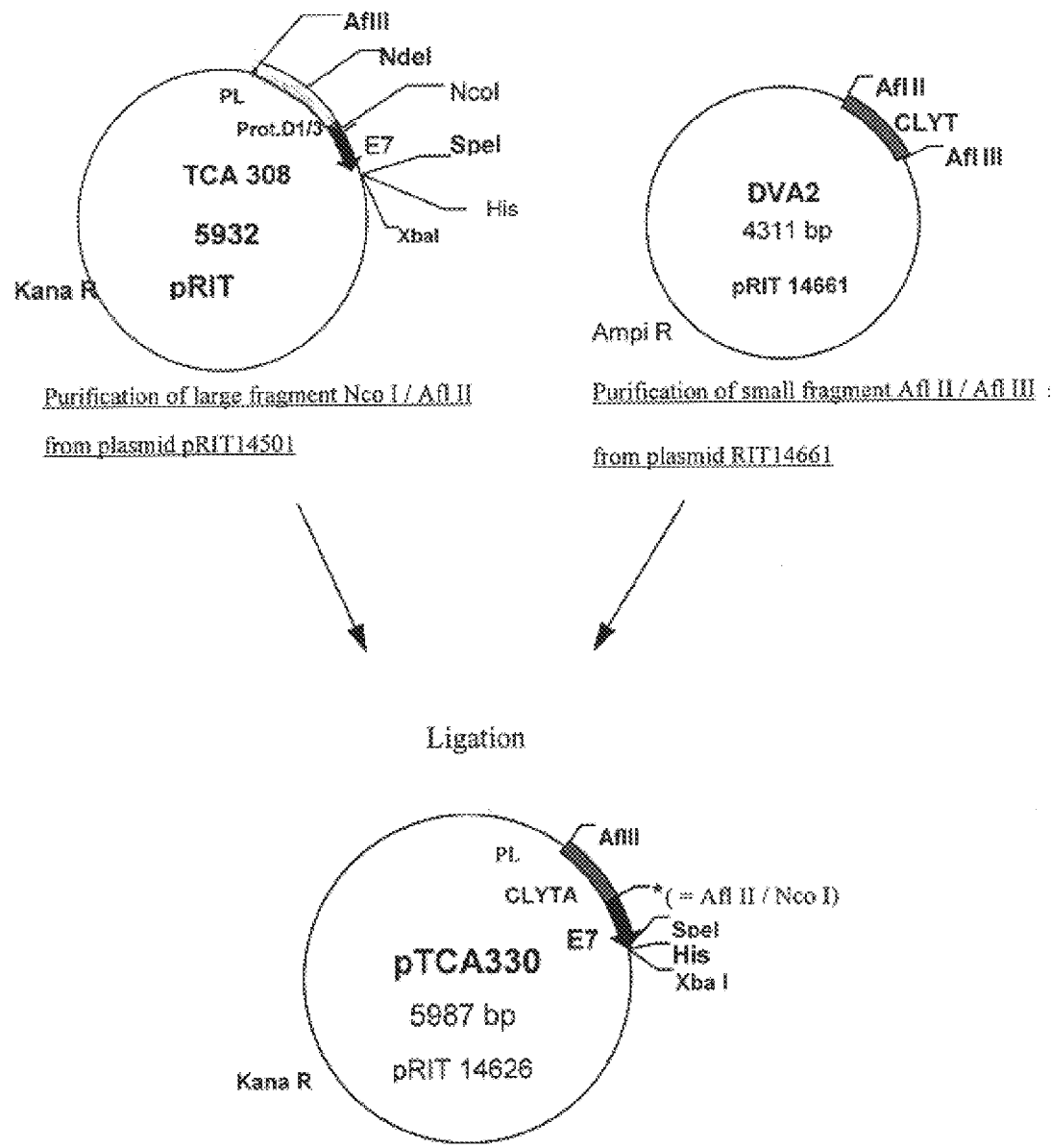
FIG. 11 is a diagram describing the construction of plasmid TCA330.

1.b Construction of Plasmid pRIT14626 (=TCA330): a Plasmid Expressing the Fusion Clyta-E7-His/HPV16 a) The first step was the purification of the large NcoI-AflII restriction fragment from plasmid pRIT14501 and the purification of the small AflII-AflIII restriction fragment from pRITI14661 b) The second step was linking of clyta sequences to the E7-His sequences (NcoI and AflIII are compatible restriction sites) that gave rise to the plasmid pRIT 14626 (=TCA330), coding for the fusion protein clyta-E7-His under the control of the pL promoter. (FIG. 11)

The coding sequence for the fusion protein clyta-E7-His is described in FIG. 12.

2. Transformation of AR58 Strain

Plasmid pRIT14626 was introduced into *E. coli* AR58 (Mott et al., 1985, Proc. Natl. Acad. Sci., 82:88) a defective λ lysogen containing a thermosensitive repressor of the λ pL promoter.

3. Growth and Induction of Bacterial Strain—Expression of clyta-E7-His

Cells of AR58 transformed with plasmid pRIT14626 were grown in 100 ml of LB medium supplemented with 50 µgr/ml of Kanamycin at 30° C. During the logarithmic phase of growth bacteria were shifted to 39° C. to inactivate the λ repressor and turn on the synthesis of protein clyta-E7-his. The incubation at 39° C. was continued for 4 hours. Bacteria were pelleted and stored at −20° C.

4. Characterization of Fusion Clyta-E7-his

Figure 15:
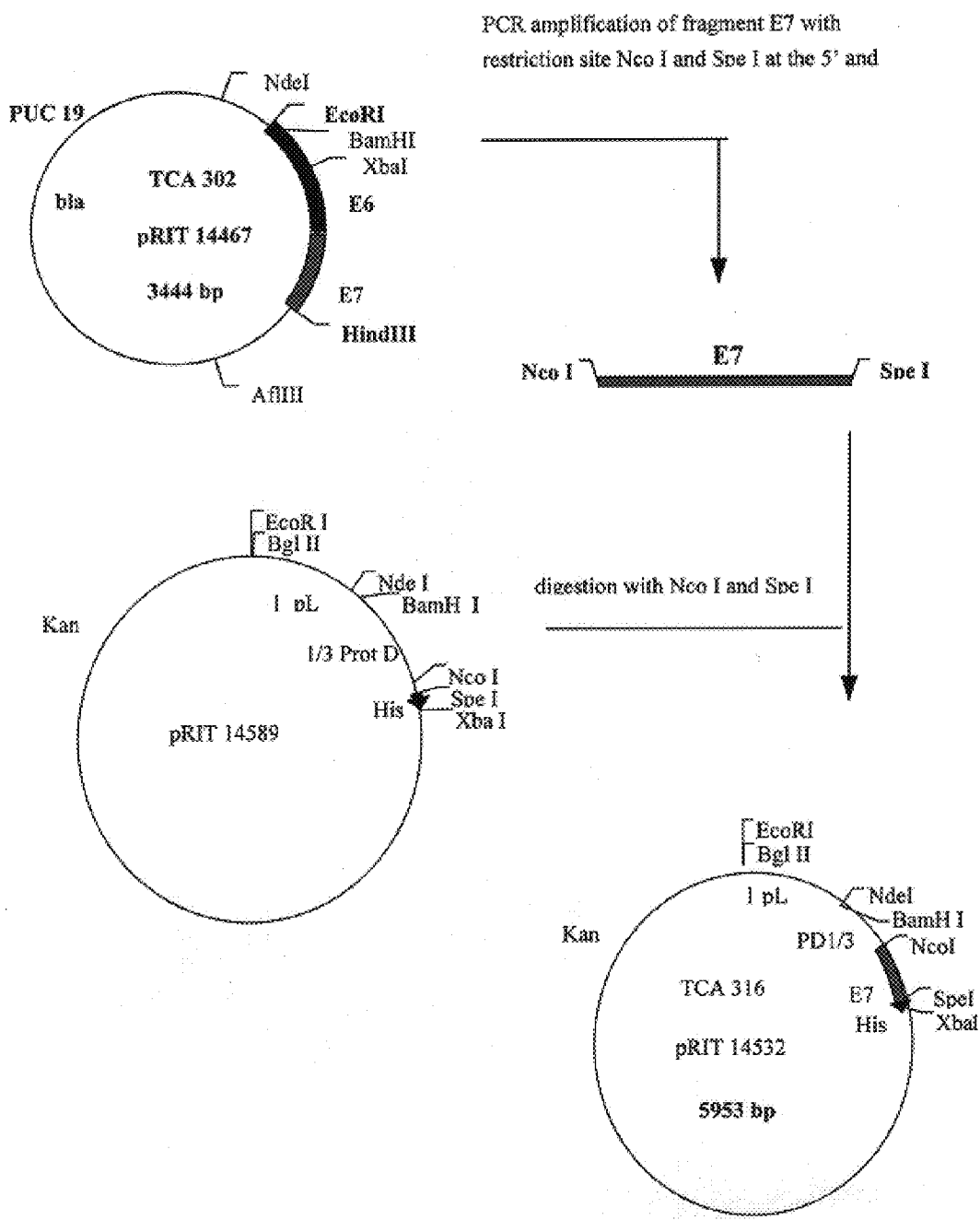
FIG. 15 is a diagram describing the construction of plasmid TCA316.

Immunity, Jan. p.119–125). The sequence of Prot-D1/3 is followed by a multiple cloning site (11 residues) and a coding region for a C-terminal histidine tail (6 His) (see FIG. 15). This plasmid is used to express the fusion protein D1/3-E7-his.

b)—HPV genomic E6 and E7 sequences of prototype HPV18(Cole et al,J.Mol.Biol.(1987)193,599–608) were amplified from HPV16 fill length genome cloned in pBR322 (obtained from Deutsche Krebsforschungszentrum (DKFZ), Referenzzentrum für human pathogen Papillomaviruses—D 69120—Heidelberg) and were subcloned into pUC19 to give TCA 302 (=pRIT14467).

Construction of Plasmid TCA 316(=pRIT14532)

The nucleotides sequences corresponding to amino acids 1→105 of E7 protein were amplified from pRIT14467.

During the polymerase chain reaction, NcoI and SpeI restriction sites were generated at the 5' and 3' ends of the E7 sequences allowing insertion into the same sites of plasmid pMGMCS Prot D1/3 to give plasmid TCA316 (=pRiT14532). The insert was sequenced and a modification versus E7/HPV 18 prototype sequence was identified in E7 gene (nucleotide 128 G→A) generating a substitution of a glycine by a glutamic acid (aa 43 in E7, position 156 in fusion protein). The sequence for the fusion protein-D1/3-E7-His/HPV 18 is described in FIG. 16.

1)b. Construction of plasmid TCA313 (=pRIT14523): a plasmid expressing thioredoxin
Starting Materials
a)—Plasmid pBBR1MCS4(Antoine R. and C. Locht, Mol.Microbiol. 1992,6,1785–1799; M. E. Kovach et al. Biotechniques 16, (5), 800–802 )which is compatible with plasmids containing Co1E1 or P15a origins of replication.
b)—Plasmid pMG42 (described in WO93/04175) containing the sequence of promoter pL of Lambda phage
c)—Plasmid pTRX (Invitrogen, kit Thiofusion K350–01) bearing the coding sequence for thioredoxin followed by AspA transcription terminator.
Construction of Plasmid TCA313(=pRIT14523)

Figure 17:
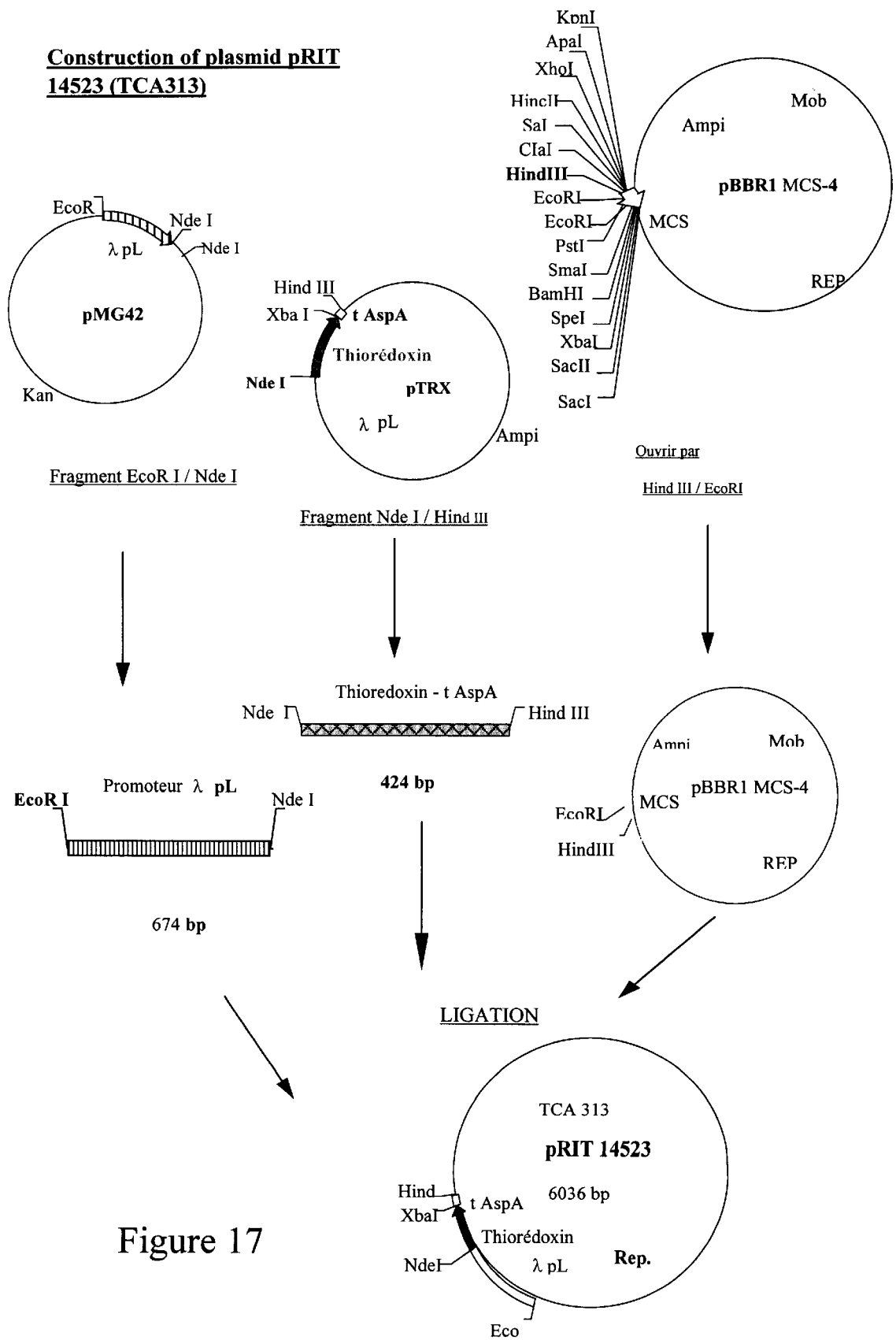
FIG. 17 is a diagram describing the construction of plasmid TCA313.

The fragment EcoRI-NdeI fragment from pMG42, bearing pL promoter and the NdeI-HindIII fragment from pTRX, bearing the coding sequence for thioredoxin followed by AspA terminator, were purified and ligated into the EcoRI and HindIII sites of plasmid vector pBBR1MCS4 to give plasmid TCA313(=pRIT14523) (see FIG. 17).

The sequence for thioredoxin is described in FIG. 18.
2)—Transformation of AR58 Strain
2).a. To obtain strain B1011 expressing ProtD1/3-E7-His/HPV18

Plasmid pRIT14532 was introduced into *E. coli* AR58 (Mott et al., 1985, Proc. Natl. Acad. Sci., 82:88) a defective λ lysogen containing a thermosensitive repressor of the λ pL promoter, by selection for transformants resistant to kanamycine.

2).b. Construction of strain B1012 expressing ProtD1/3-E7-His/HPV18 and thioredoxin Plasmid pRIT14532 and pRIT14523 were introduced into *E. coli* AR58 (Mott et al., 1985, Proc. Natl. Acad. Sci., 82:88) a defective λ lysogen containing a thermosensitive repressor of the λ pL promoter, by double selection for transformants resistant to kanamycin and ampicillin.

3)—Growth and Induction of Bacterial Strains B1011 and B1012—of Expression Prot-D1/3-E7-His/HPV18 Without and with Thioredoxin in Trans Cells of AR58 transformed with plasmids pRIT14532 (B1011 strain) and Cells of AR58 transformed with plasmids pRIT14532 and pRIT14523 (B1012 strain) were grown at 30° c in 100 ml of LB medium supplemented with 50 µgr/ml of Kanamycin for B1011 strain and supplemented 50 µgr/ml of Kanamycin and 100 µgr/ml of Ampicillin for B1012 strain. During the logarithmic phase of growth bacteria were shifted to 39° C. to inactivate the λ repressor and turn on the synthesis of protein D1/3-E7-his/HPV18 and thioredoxin. The incubation at 39° C. was continued for 4 hours. Bacteria were pelleted and stored at –20° C.

Characterization of Fusion Protein D1/3-E7-his /HPV18
Preparation of Extracts

Frozen cells are thawed and resuspended in 10 ml of PBS buffer. Cells are broken in a French pressure cell press SLM Aminco at 20,000 psi (three passages). The extract is centrifuged at 16,000 g for 30 minutes at 4° C.

Analysis on Coomassie-Stained SDS-polyacrylamide Gels and Western Blots

After centrifugation of extracts described above, aliquots of supernatant and pellet were analysed by SDS-polyacrylamide gel electrophoresis and Western blotting.

The fusion protD1/3-E7-His (about 31 kDa) was visualised by Coomassie stained gels in the pellet fraction for strain B1011 and partially localized (30% ) in the supernatant fraction for strain B1012 and was identified in Western blots by rabbit polyclonal anti-protein-D and by Ni-NTA conjugate coupled to calf intestinal alkaline phosphatase (Qiagen cat. no° 34510) which detects accessible histidine tail. The level of expression represents about 1–3% of total protein as shown on a Coomassie-stained SDS-polyacrylamide gel.

For the extract of strain B 1012 the thioredoxin ( about 12 KDa) was visualised by coomassie stained gel in the supernatant and identified in western blots by monoclonal anti thioredoxin ( Invitrogen R920-25)

Purification of Prot D 1/3 E7-his/HPV18

Recombinant HPV 18-ProtD 1/3-E7-His is expressed in *E. coli* (as described above) AR58 strain. All steps are performed at room temperature (RT≅22° C.). Proteins are followed by monitoring $OD_{280\ nm}$. Between steps, antigens positive fractions are kept at –20° C.

Purified antigen is stable one week at –20° C. and 4° C. (no degradation) but appears more susceptible to oxidation after incubation at 37° C.

d)—Solubility

Protein solubility is pH dependent (see below) with decrease of solubility for pH<7.4:

| | | |
|---|---|---|
| PBS pH 7.4 | 686 µg/ml | 100% |
| PBS pH 7.2 | 560 µg/ml | 81% |
| PBS pH 7.0 | 498 µg/ml | 72% |
| PBS pH 6.8 | 327 µg/ml | 48% | e)—The HPV 18 Prot D1/3 E7 protein is composed of 227 amino acids. Its theoretical molecular weight is 25.9 kDa, and a theoretical isoelectric point of 5.83. It migrates at about 31.5 kDa in reducing SDS PAGE.

EXAMPLE XIV

Purification of HPV 18 Protein D1/3 E7
a)—Solubilisation

Cell paste is suspended to 60 $OD_{600}$ in 2 M NaCl, 20 mM Phosphate.

($NaH_2PO4/K_2HPO4$) pH 7.6 prior cell lysis by two passes through a Rannie disruptor. Lysed cells are pelleted 30 min at 9,000 rpm in a JA 10 rotor at 4° C. In order to reduce endotoxin level, bacterial cell pellet containing the recombinant protein is washed once in 5 mM EDTA, 2 M NaCl, PBS pH 7.4; once in 4 M urea, 20 mM Phosphate pH 7.4 and finally once in PBS pH 7.4 to eliminate trace of EDTA (each wash is performed in twice volume used for cell suspension). HPV18-Prot.D1/3-E7-His (TIT for Thioredoxin In Trans) is solubilised (in the same volume used for cell suspension) by 6 M Guanidine-Chloride, 50 mM PO4 pH 7.6 overnight at 4° C. Cell debris are pelleted 30 min at 9,000 rpm in a JA 10 rotor at 4° C. Supernatant is supplemented with 0.5% Empigen BB and incubated 30 min at RT.

b)—Purification

1).a.Immobilized Metal Affinity Chromatography 125. ml of sample are loaded onto a $Zn^{2+}$-Chelating Sepharose FF column (XK 26/20, Pharrmcia; 50 ml gel/125 ml solubilisation) preequilibrated in 0.5% Empigen BB, 6 M Guanidine-Chloride, 50 mM PO4 pH 7.6 at 4 ml/min. Column is washed by Guanidine Chloride 6M, PO4 50 mM pH 7.6 until the base line is reached then by 6 M urea, 0.5 M NaCl, 50 mM PO4 pH 7.6. Antigen is eluted by 0.25 M-Imidazole in 6 M urea, 0.5 M NaCl, 50 mM PO4 pH 7.6, at 2 ml/min (FIG. 1B). IMAC-eluted sample is dialyzed at 4° C. versus PBS pH 7.4

1).b. Affi-Prep® Polymixin (Bio-Rad)

To reduce endotoxin level, 28 mg (37 ml) of antigen are incubated in batch mode with 2 ml of Affiprep Polymyxin resin prequilibrated in PBS pH 7.4, over night at room temperature. Protein recovery is estimate at 60% and endotoxin content is reduced 6.5 times.

1).c. Analysis

Purified antigen analyzed on reducing-SDS-PAGE presents a major 30 kDa band with a second one at 55 kDa, after Coomassie Blue or Silver Staining. In a non reducing SDS-PAGE, HPV-18-ProtD1/3-E7-His appears mainly like a smear with Molecular Weight≧175 kDa. However this oxidation can be reversed by addition of 5 mM of β-Mercapto-Ethanol. This pattern is confirmed by anti ProtD or by anti His Western Blotting analysis.

c)—Stability

Purified antigen is stable one week at −20° C. and 4° C. (no degradation) but appears more susceptible to oxidation after incubation at 37° C.

d)—Solubility

Protein solubility is pH dependent (see below) with decrease of solubility for pH<7.4:

| | | |
|---|---|---|
| PBS pH 7.4 | 686 µg/ml | 100% |
| PBS pH 7.2 | 560 µg/ml | 81% |
| PBS pH 7.0 | 498 µg/ml | 72% |
| PBS pH 6.8 | 327 µg/ml | 48% |

HPV18-ProtD1/3-E7-His protein is composed of 227 amino acids. Its theoretical molecular weight is 25.9 kDa. It migrates at about 31.5 kDa in reducing SDS-PAGE. Theoretical isoelectric point is 5.83.

EXAMPLE XV

Construction of *E.coli* Strain B1098 Expressing Fusion ProtD1/3-E7

Mutated (cys27→gly,glu29→gln3 type HPV18

1)—Construction of Expression Plasmid

Starting Material a)—Plasmid pRIT 14532 (=TCA 316) which codes for fusion ProtD1/3-E7 -His b)—Plasmid LITMUS 28 (New England Biolabs cat n° 306–28), a cloning vector pUC-derived c)—Plasmid pMG MCS ProtD1/3 (pRIT 14589), a derivative of pMG81 (described supra) in which the codons 4–81 of NS1 coding region from Influenza were replaced by the codons corresponding to residues Ser 20→Thr 127 of mature protein D of Haemophilus Influenzae strain 772, biotype 2 (H. Janson et al., 1991, Infection and Immunity, Jan. p.119–125). The sequence of Prot-D1/3 is followed by a multiple cloning site (11 residues) and a coding region for a C-terminal histidine tail (6 His)

Construction of Plasmid pRIT 14831 (=TCA355): a Plasmid Expressing the Fusion Protein-D1/3-E7 Mutated (cys27→gly ,glu29→gln) with His Tail The NcoI-XbaI fragment from pRIT 14532 (=TCA 316), bearing the coding sequence of E7 gene from HPV18, elongated with an His tail, was subcloned in an intermediate vector Litmus 28 useful for mutagenesis to give pRIT 14910 (=TCA348) By analogy with E7/HPV16 mutagenesis, double mutations cys27→gly and glu29→gln were chosen to impair the binding to the antioncogene product of Retinoblastome gene (pRB).

Figure 19:
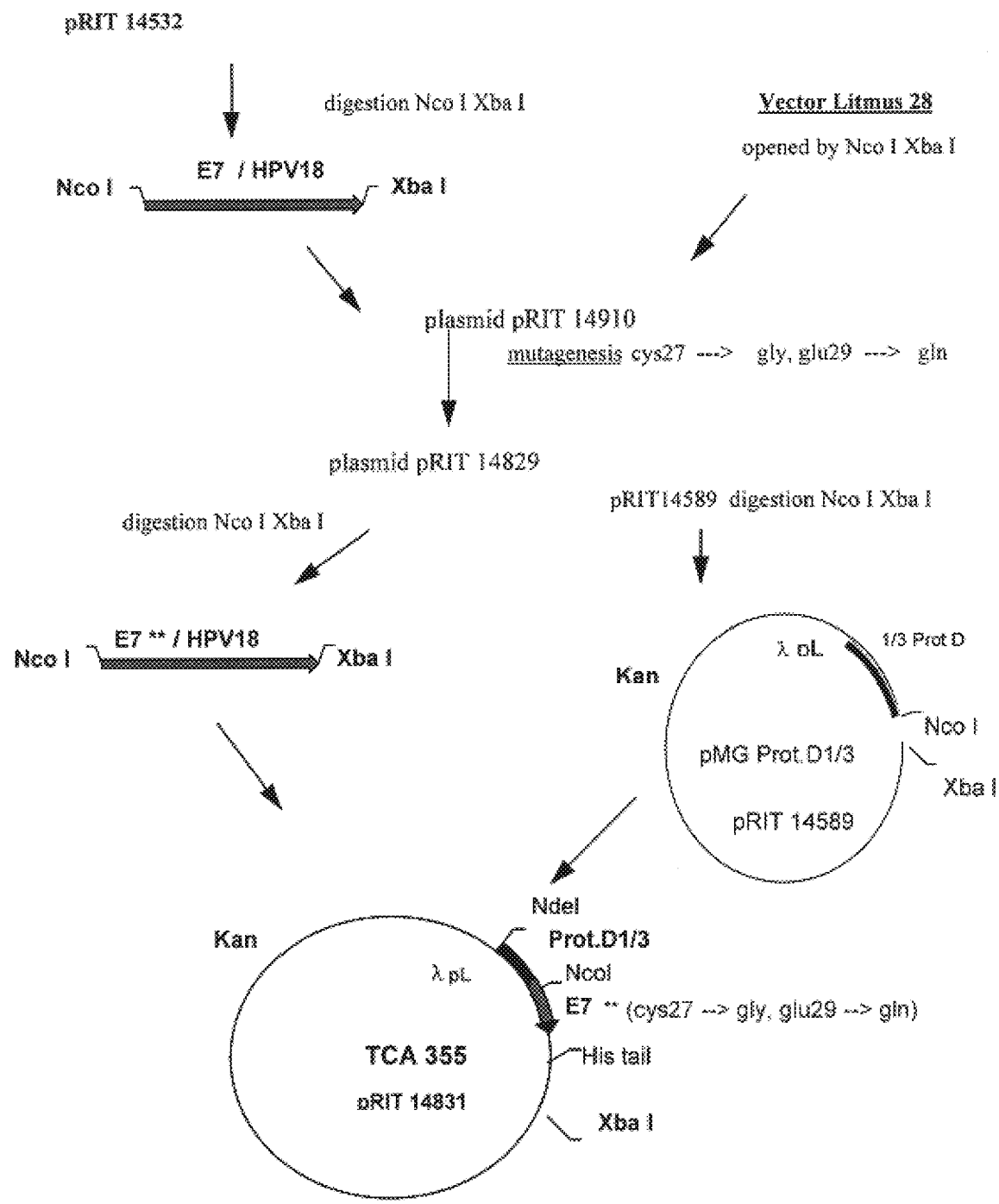
FIG. 19 is a diagram describing the construction of plasmid TCA355.

The introduction of mutations in E7 gene was realized with the kit "Quick Change Site directed Mutagenesis (Stratagene cat n° 200518). As the sequencing of pRIT14532 had pointed out the presence of a glutamic acid in position 43 of E7 instead of a glycine in the prototype sequence of HPV18, a second cycle of mutagenesis was realized to introduce a glycine in position 43. We obtained plasmid pRIT 14829 (=TCA353). After verification of presence of mutations and integrity of the complete E7 gene by sequencing, the mutated E7 gene was introduced into vector pRIT 14589 (=pMG MCS ProtD1/3) to give plasmid pRIT 14831 (=TCA355) (see FIG. 19).

The sequence for the fusion protein-D1/3-E 7 mutated (cys27→gly, glu29→gln) -His is described in the FIG. 20.

2)Construction of Strain B1098 Expressing ProtD1/3-E7Mutated (cys 27→gly, glu29→gln)-His/HPV18

Plasmid pRIT 14831 was introduced into *E.coli* AR58 (Mott et al.,1985, Proc. Natl. Acad. Sci., 82:88) a defective λ lysogen containing a thermosensitive repressor of the λ pL promoter, to give strain B1098, by selection for transformants resistant to kanamycin.

3)—Growth and Induction of Bacterial Strain B1098— Expression of ProtD1/3-E7 Mutated (cys 27→gly, glu29→gln)-His/HPV18

Cells of AR58 transformed with plasmid pRIT 14831 (B1098 strain) were grown at 30° C. in 100 ml of LB medium supplemented with 50 µgr/ml of Kanamycin. During the logarithmic phase of growth bacteria were shifted to 39° C. to inactivate the λ repressor and tun on the synthesis ofProtD1/3-E7 mutated-His/HPV18. The incubation at 39° C. was continued for 4 hours. Bacteria were pelleted and stored at −20° C.

4)—Characterization of Fusion ProtD1/3E7 mut (cys24→gly, glu26→gln)-His Type HPV16

Frozen cells were thawed and resuspended in 10 ml of PBS buffer. Cells were broken in a French Pressure cell press SLM Aminco at 20,000 psi (three passages). The extract was centrifuged at 16000 g for 30 minutes at 4° C. Analysis on Coomassie stained SDS-polyacrylamide gels and Western blots After centrifugation of extracts described above, aliquots of supernatant and pellet were analysed by SDS-polyacrylamide gel electrophoresis and Western blotting. A major band of about 31 kDa, localized in the pellet fraction, was visualised by Coomassie stained gels and identified in Western blots by rabbit polyclonal 22 J 70 anti-protein D and by monoclonal Penta-His (Qiagen cat. n° 34660) which detects accessible histidine tail. The level of expression represents about 3 to5 % of total protein.

EXAMPLE XVI

Construction of an *E.coli* Strain Expressing Fusion Protein-D1/3-E6-his/HPV18

1. Construction of Expression Plasmid a) Plasmid pMG MCS prot D1/3 (=pRIT14589) is a derivative of pMG81 (described supra) in which the codons 4–81 of NS1 coding region from Influenza were replaced by the codons corresponding to residues Ser 20→Thr 127 of mature protein D of Haemophilus Influenzae strain 772, biotype 2 (H. Janson et al., 1991, Infection and Immunity, Jan. p. 119–125). The sequence of Prot-D1/3 is followed by a multiple cloning site (11 residues) and a coding region for a C-terminal histidine tail (6 His). This plasmid is used to express the fusion protein D1/3-E6-his. HPV genomic E6 and E7 sequences type HPV18 (Cole et al., J. Mol. Biol. 1987, 193, p.599–608.) were amplified from HPV18 full length genome cloned in pBR322

(obtained from Deutsches Krebsforschungszentrum (DKFZ), Referenzzentrum für human pathogen Papillomavirnses—D 69120—Heidelberg) and were subcloned into pUC19 to give TCA 302 (=pRIT14467).

Construction of Plasmid TCA 314(=pRIT14526): a Plasmid Expressing the Fusion Protein-D1/3-E6-His/HIPV18

Figure 21:
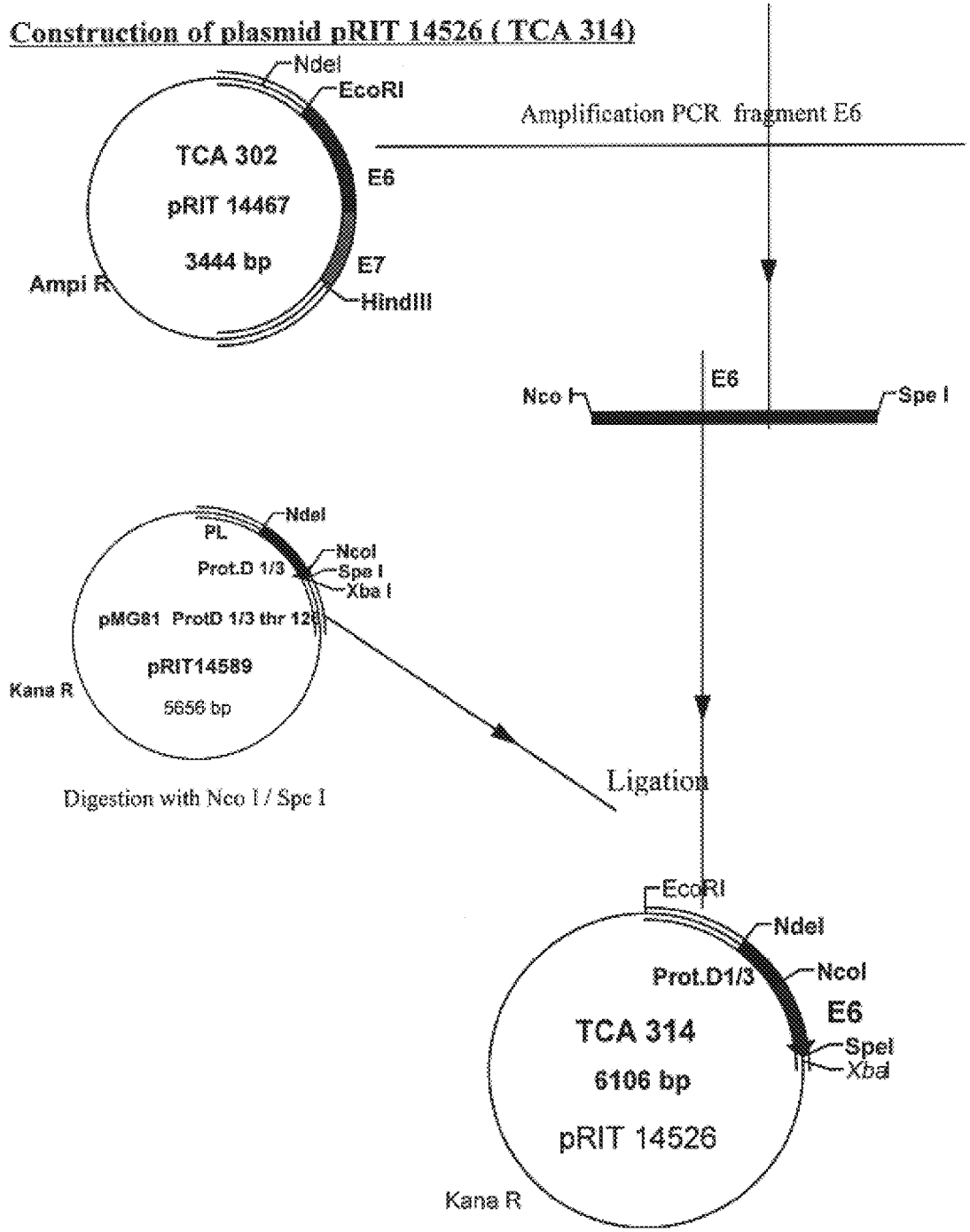
FIG. 21 is a diagram describing the construction of plasmid TCA314.

The nucleotides sequences corresponding to amino acids 1→158 of E6 protein were amplified from pRIT14467. During the polymerase chain reaction, NcoI and SpeI restriction sites were generated at the 5' and 3' ends of the E6 sequences allowing insertion into the same sites of plasmid pMGMCS Prot D1/3 to give plasmid TCA314 (=pRIT14526) (see FIG. 21). The insert was sequenced to verify that no modification had been generated during the polymerase chain reaction. The coding sequence for the fusion protein-D1/3-E6-His is described in FIG. 22.

Transformation of AR58 Strain

Plasmid pRIT14526 was introduced into *E. coli* AR58 (Mott et al., 1985, Proc. Natl. Acad. Sci., 82:88) a defective λ lysogen containing a thermosensitive repressor of the λ pL promoter.

3. Growth and Induction of Bacterial Strain—Expression of Prot-D1/3-E6-His

Cells of AR58 transformed with plasmid pRIT14526 were grown in 100 ml of LB medium supplemented with 50 μgr/ml of Kanamycin at 30° C. During the logarithmic phase of growth bacteria were shifted to 39° C. to inactivate the λ repressor and turn on the synthesis of protein D1/3-E6-his. The incubation at 39° C. was continued for 4 hours. Bacteria were pelleted and stored at −20 C.

4. Characterization of Fusion Protein D1/3-E6-his

Frozen cells are thawed and resuspended in 10 ml of PBS buffer. Cells are broken in a French pressure cell press SLM Aminco at 20.000 psi (three passages). The extract is centrifuged at 16.000 g for 30 minutes at 4° C. After centrifugation of extracts described above, aliquots of supernatant and pellet were analysed by SDS-polyacrylamide gel electrophoresis and Western blotting. A major band of about 32 kDa, localized in the pellet fraction, was visualised by Coomassie stained gels and identified in Western blots by rabbit polyclonal anti-protein-D and by Ni-NTA conjugate coupled to calf intestinal alkaline phosphatase (Qiagen cat. n° 34510) which detects accessible histidine tail. The level of expression represents about 3–5% of total protein.

EXAMPLE XVII

Construction of an *E. coil* Strain Expressing Fusion Protein-D1/3-E6E7-his/HPV18

1. Construction of Expression Plasmid a) Plasmid pMG MCS prot D1/3 (=pRIT14589) is a derivative of pMG81 (described supra) in which the codons 4–81 of NS1 coding region from Influenza were replaced by the codons corresponding to residues Ser 20→Thr 127 of mature protein D of Haemophilus Influenzae strain 772, biotype 2 (H. Janson et al., 1991, Infection and Immunity, Jan. p.119–125). The sequence of Prot-D1/3 is followed by a multiple cloning site (11 residues) and a coding region for a C-terminal histidine tail (6 His). This plasmid is used to express the fusion protein D1/3-E6E7-his.

b) HPV genomic E6 and E7 sequences type HPV18 (Cole et al.,J.Mol.Biol. 1987, 193, 599–608) were amplified from HPV 18 full length genome cloned in pBR322 (obtained from Deutsches Krebsforschungszentrum (DKFZ), Referenzzentrum für human pathogen Papillomaviruses—D 69120—Heidelberg) and were subcloned into pUC19 to give TCA 302 (=pRIT14467).

c) The coding sequences for E6 and E7 in TCA302 (=pRIT 14467) were modified with a synthetic oligonucleotides adaptor (inserted between Hga I and Nsi I sites) introducing a deletion of 11 nucleotides between E6 and E7 genes, removing the stop codon of E6 and creating fused E6 and E7 coding sequences in the plasmid TCA320(=pRIT 14618 ) see FIG. 23.

Construction of Plasmid TCA 328(=pRIT14567): a Plasmid Expressing the Fusion Protein-D1/3-E6E7-His/HPV18

Figure 24:
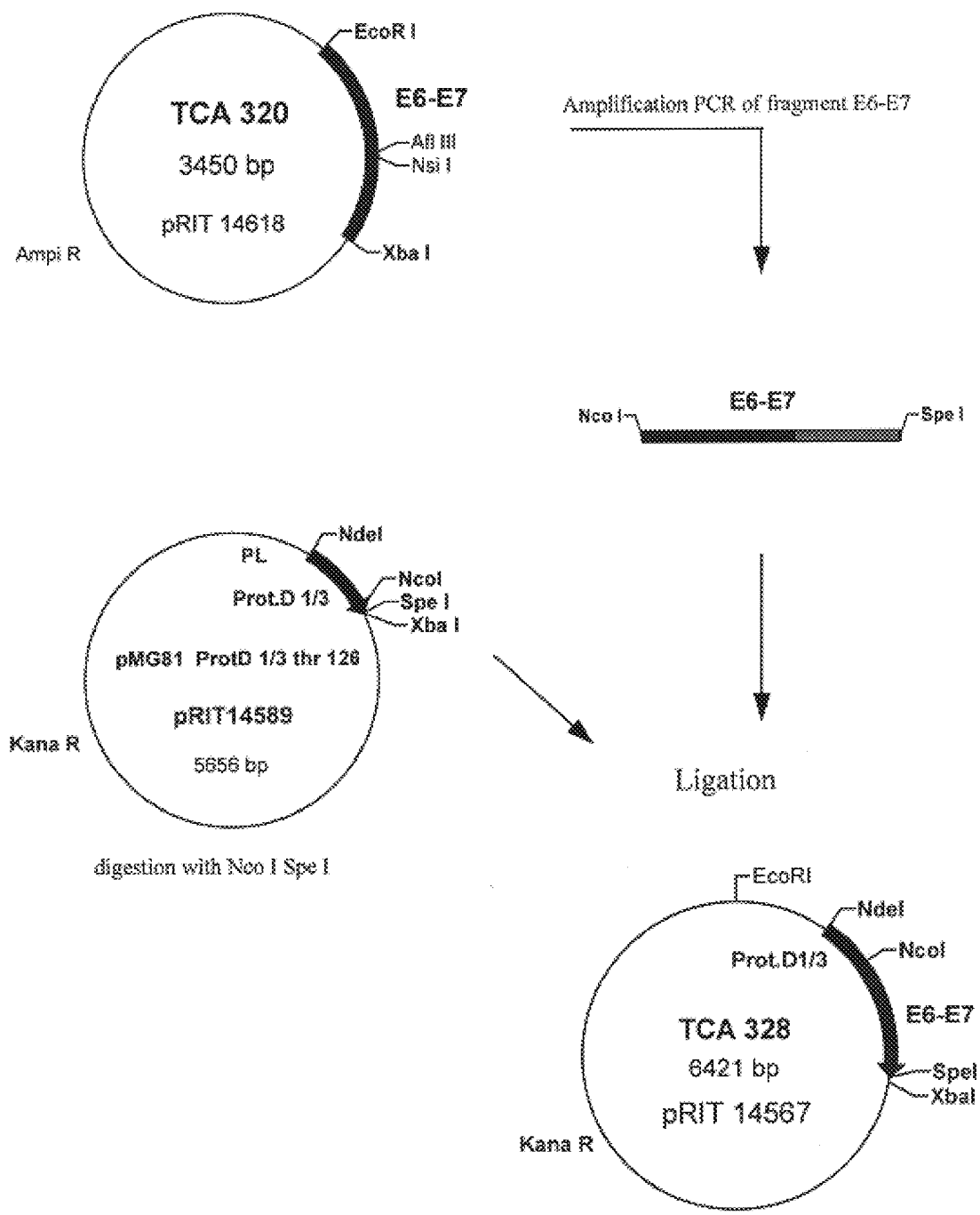
FIG. 24 is a diagram describing the construction of plasmid TCA328.

The nucleotides sequences corresponding to amino acids 1→263 of fused E6E7 protein were amplified from pRIT14618. During the polymerase chain reaction, NcoI and SpeI restriction sites were generated at the 5' and 3' ends of the E6E7 fused sequences allowing insertion into the same sites of plasmid pMGMCS Prot D1/3 to give plasmid TCA328 (=pRIT14567) (see FIG. 24). The insert was sequenced to verify that no modification had been generated during the polymerase chain reaction. The coding sequence for the fusion protein-D1/3-E6E7-His is described in FIG. 25.

2. Transformation of AR58 Strain

Plasmid pRIT14567 was introduced into *E. coli* AR58 (Mott et al., 1985, Proc. Natl. Acad. Sci., 82:88) a defective λ lysogen containing a thermosensitive repressor of the λ pL promoter.

3. Growth and Induction of Bacterial Strain—Expression of Prot-D1/3-E6E7-His

Cells of AR58 transformed with plasmid pRIT14512 were grown in 100 ml of LB medium supplemented with 50 μgr/ml of Kanamycin at 30° C. During the logarithmic phase of growth bacteria were shifted to 39° C. to inactivate the λ repressor and turn on the synthesis of protein D1/3-E6E7-his. The incubation at 39° C. was continued for 4 hours. Bacteria were pelleted and stored at −20 C.

4.Characterization of Fusion Protein D1/3-E6E7-His

Frozen cells are thawed and resuspended in 10 ml of PBS buffer. Cells are broken in a French pressure cell press SLM Aminco at 20.000 psi (three passages). The extract is centrifuged at 16.000 g for 30 minutes at 40° C. After centrifugation of extracts described above, aliquots of supernatant and pellet were analysed by SDS-polyacrylamide gel electrophoresis and Western blotting. A major band of about 48 kDa, localized in the pellet fraction, was visualised by Coomassie stained gels and identified in Western blots by rabbit polyclonal anti-protein-D and by Ni-NTA conjugate coupled to calf intestinal alkaline phosphatase (Qiagen cat. n° 34510) which detects accessible histidine tail. The level of expression represents about 1% of total protein.

EXAMPLE XVIII

Vaccine Formulations

Vaccines are formulated with a Protein from the above examples expressed in *E. coli* from the strain AR58, and as adjuvant, the formulation comprising a mixture of 3 de-O-acylated monophosphoryl lipid A (3D-MPL) and aluminium hydroxide or 3D-MPL and/or QS21 optionally in an oil/water emulsion, and optionally formulated with cholesterol.

3D-MPL: is a chemically deoxidized form of the lipopolysaccharide (LPS) of the Gram-negative bacteria Salmonella minnesota. Experiments performed at Smith Kline Beecham Biologicals have shown that 3D-MPL combined with various vehicles strongly enhances both the humoral and a TH1 type of cellular immunity.

QS21: is one saponin purified from a crude extract of the bark of the Quillaja Saponaria Molina tree, which has a strong adjuvant activity: it activates both antigen-specific lymphoproliferation and CTLs to several antigens.

Vaccine containing an antigen of the invention containing 3D-MPL and alum may be prepared in analogous manner to that described in WO93/19780 or 9216231.

Experiments performed at Smith Kline Beecham Biologicals have demonstrated a clear synergistic effect of combinations of 3D-MPL and QS21 in the induction of both humoral and TH1 type cellular immune responses. Vaccines containing an antigen such antigens are described in U.S. Pat. No. 5,750,110.

The oil/water emulsion is composed of 2 oils (a tocopherol and squalene), and of PBS containing Tween 80 as emulsifier. The emulsion comprised 5% squalene 5% tocopherol 0.4% Tween 80 and had an average particle size of 180 nm and is known as SB62 (see WO 95/17210).

Experiments performed at Smith Kline Beecham Biologicals have proven that the adjunction of this O/W emulsion to MPL/QS21 further increases their immunostimulant properties.

Preparation of Emulsion SB62 (2 Fold Concentrate)

Tween 80 is dissolved in phosphate buffered saline (PBS) to give a 2% solution in the PBS. To provide 100 ml two fold concentrate emulsion 5 g of DL alpha tocopherol and 5 ml of squalene are vortexed to mix thoroughly. 90 ml of PBS/Tween solution is added and mixed thoroughly. The resulting emulsion is then passed through a syringe and finally microfluidised by using an M110S mcirofluidic machine. The resulting oil droplets have a size of approximately 180 nm.

Preparation of Prot.D1/3 E7 QS21/3D MPL Oil in Water Formulation

ProtD1/3-E7 (5 μg) was diluted in 10 fold concentrated PBS pH 6.8 and $H_2O$ before consecutive addition of SB62, 3 D MPL (5 μg), QS21 (5 μg) and 50 μg/ml thiomersal as preservative at 5 min interval. The emulsion volume is equal to 50% of the total volume (50 μl for a dose of 100 μl). All incubations were carried out at room temperature with agitation. The adjuvants controls without antigen were prepared by replacing the protein by PBS.

Tumour Regression Experiments (HPV 16) with PROT D E7

Vaccine Antigen: Fusion Protein ProtD E7

Protein D is a lipoprotein exposed on the surface of the Gram-negative bacteria Haemophilus influenzae. The inclusion of the 109 first residues of the protein D as fusion partner is incorporated to provide the vaccine antigen with bystander help properties. The antigen was formulated with QS21 3D-MPL and SB62 as described supra.

EXAMPLE XIX

In vivo Tumour Regression Experiments Tumour Cell line TC1:

Primary lung epithelial cells from C57BL.6 mice were immortalised by HPV 16 E6 and E7 and then transformed with an activated ras oncogene, producing a tumourigenic cell line expressing E6 and E7 (Lin KY et al 1996). The E7 expression has been verified by FACS analysis of fixed and permeabilised TC1 cells using the mouse anti-HPV 16 E7 Mab (Triton Corp. Alameda, Calif.)

Tumour Growth

Figure 26:
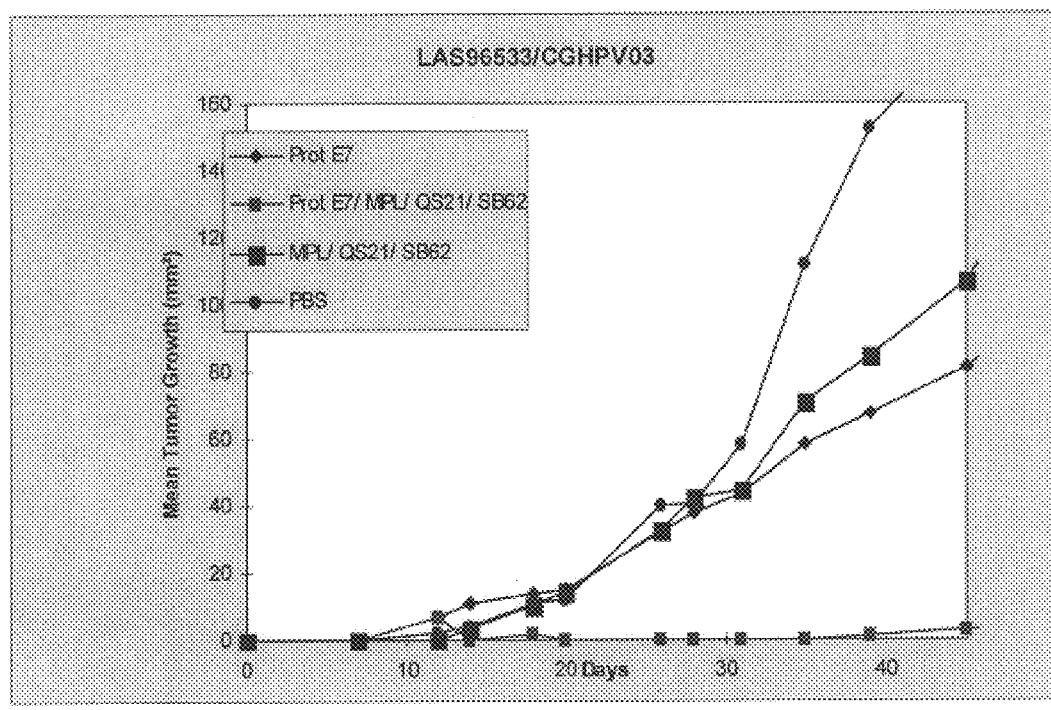
FIG. 26 graphically presents the therapeutic effect of vaccination with Protein-D1/3-E7-His /HPV16 formulations on TC1 tumor growth.

TC1 cells growing in vitro culture were trypsinised, washed two times in serum-free medium and were injected S.C. in the right flank of the mice. To assess treatment of established tumours, TC1 cells were injected at a dose of 3×10e4 cells/mouse. One and two weeks after the tumour cell injection, mice were vaccinated with 5 μg in 100 μl of protD 1/3 E7 His intra foot pad (50 μl/foot pad) in PBS or in the 3D-MPL, QS21 and SB62 or with PBS or with the adjuvant alone. Five C57BL/6 mice (Iffa Credo) were used in each group. Mice were monitored twice a week for tumour growth. The mean tumour mass/group is shown in FIG. 26, the mice vaccinated with protD 1/3 E7 His in PBS or with PBS or the adjuvant alone developed progressively growing tumours (0–1 tumour-free animal/group). On the contrary, four out of five mice vaccinated with protD1/3 E7 His in adjuvant did not develop a tumour, one animal developed a very small and stable tumour at day 40. This results indicate that the protein protD1/3 E7 His from HPV 16 formulated in adjuvant is able to induce the regression of small established tumours expressing this antigen.

Immunological Read Out

Proliferation Assay

For in vitro assay, Lymphocytes were prepared by crushing the spleen or the popliteal lymph nodes from the vaccinated mice at day 69. An aliquot of 2×10e5 cells was plated in triplicate in 96 well plates with decreasing concentrations (10, 1, 0.1 μg/ml) of protD 1/3 E7 His coated or not onto latex microbeads (Sigma) to restimulate the cells in vitro (72 Hrs). T cell proliferation was measured by 3H thymidine incorporation.

Figure 27:
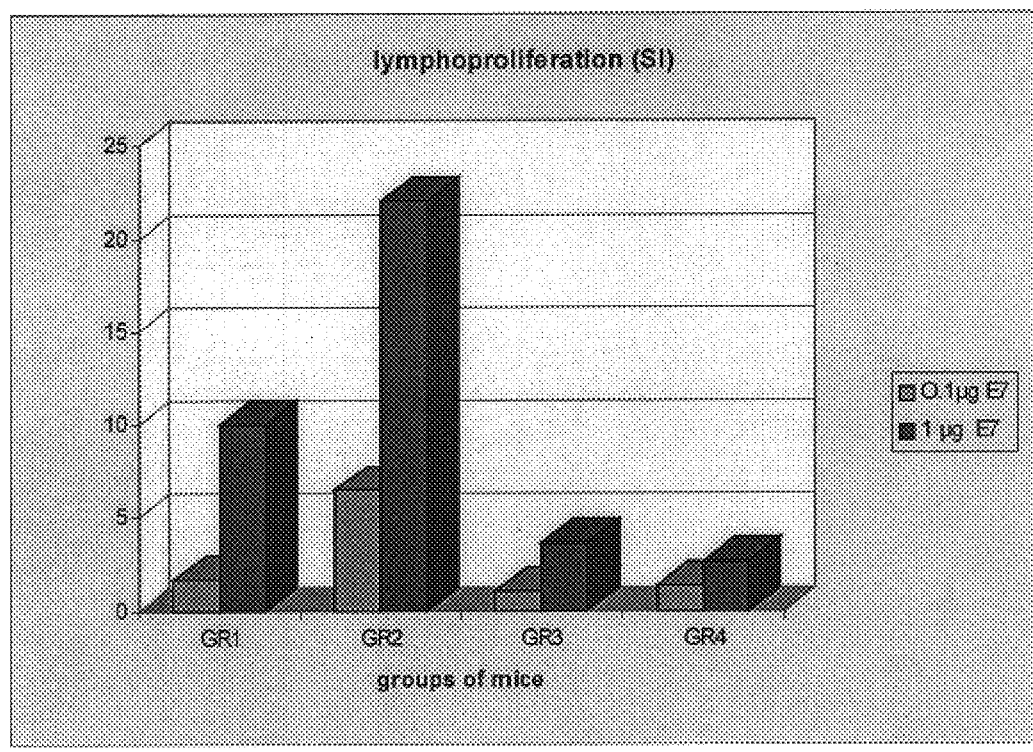
FIG. 27 presents data on lymphproliferation of splenocytes obtained from mice treated with Protein-D1/3-E7-His /HPV16 formulations after tumor establishment.
Figure 28:
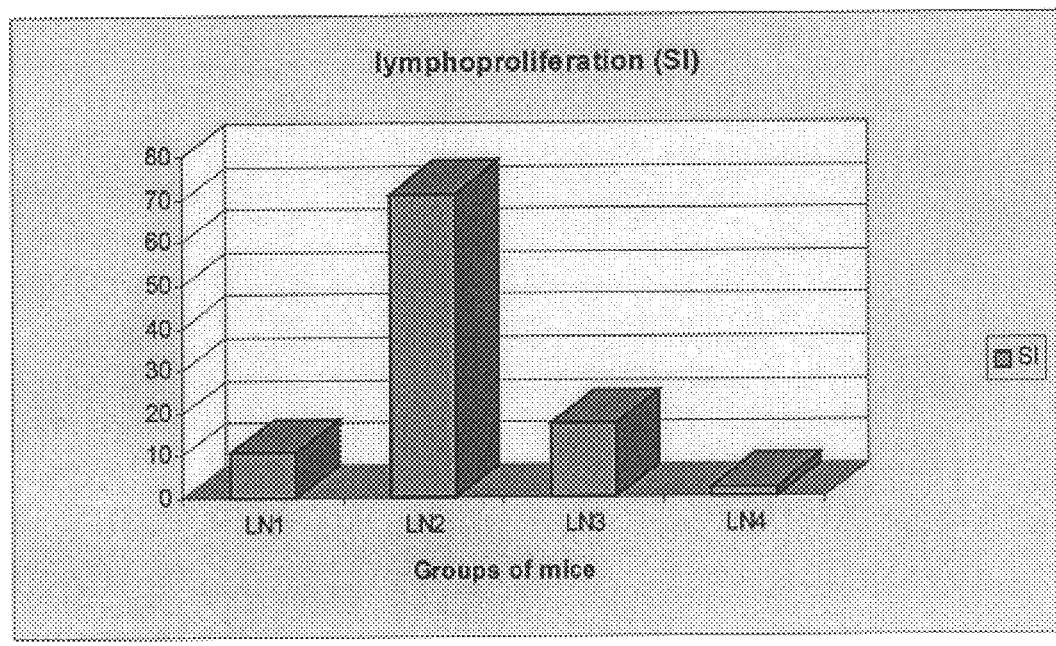
FIG. 28 presents data on lymphproliferation of lymph node cells obtained from mice treated with Protein-D1/3-E7-His /HPV16 formulations after tumor establishment.
Figure 29A:
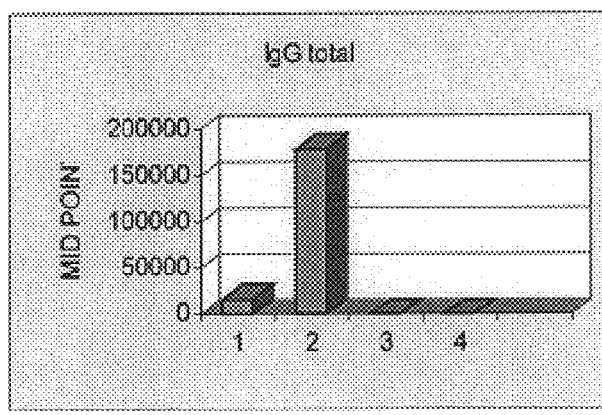
FIG. 29a presents the total IgG titer.
Figure 29B:
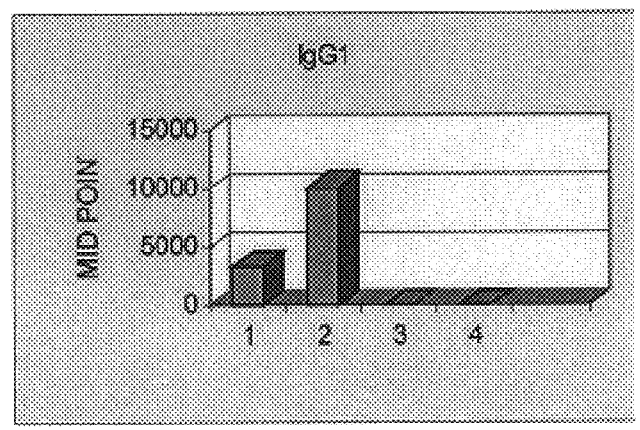
FIG. 29b presents the IgG1 titer.
Figure 29C:
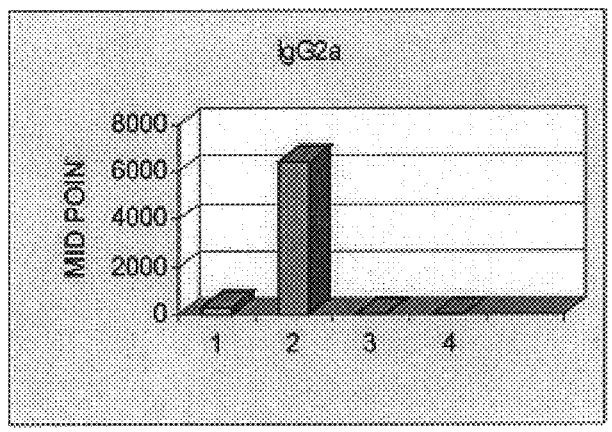
FIG. 29c presents the IgG2a titer.
Figure 29D:
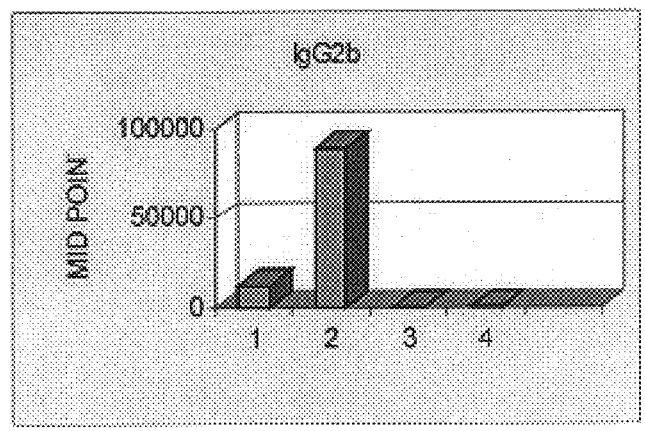
FIG. 29d presents the IgGb titer.

FIGS. 27 and 28 compares the ability of protD E7 to stimulate the proliferation of splenocytes and lymph node cells primed in vivo either by PBS, 3D-MPL, QS21 SB62, ProtD1/3 E7 His and ProtD1/3 E7 His +the adjuvant of 3D-MPL, QS21, SB62 and shows that high proliferative responses in spleen were detected only in mice immunised with protD1/3 E7 His in adjuvant compared to the other groups.

Antibody Response

Individual serum were taken at the same time as the organs were taken and submitted to indirect ELISAs.

5 μg/ml of purified E7 protein was used as coated antigen. After saturation in PBS+1% newborn calf serum 1 Hr at 37° C., the sera were serially diluted (starting at 1/100) in the saturation buffer and incubated O/N at 4° C. or 90 min at 37° C. After washing in PBS Tween 200.1%, biotinylated goat Anti mouse Ig (1/1000) or goat anti mouse Ig subclass (total IgG, IgG1, IgG2a, IgG2b) antisera (1/5000) were used as second antibodies, after an incubation of 90 min at 37° C., streptavidin coupled to peroxydase was added and TMB (tetra-methyl-benzidine/peroxide) was used as substrate, after 10 min. the reaction was stopped with H2SO4 0.5 M and the O.D.450 was determined.

The subclass-specific anti E7 titers elicited by the vaccinations in the different groups of mice are shown in FIG. 29 as a comparison of the relative mean midpoint dilution of the serum.

These results show that a weak antibody response is triggered with 2 injections of ProtD 1/3 E7 HPV16 alone.

Much more anti-E7 antibodies are generated when ProtD1/3 E7 was injected in the presence of the adjuvant SB62, QS21+3D-MPL.

No IgA nor IgM were detected in any of the serum samples even in the serum of the mice that received ProtD 1/3 E7 in the adjuvant SB62, QS21+3D-MPL (data not shown) On the contrary, the total IgG level was slightly increased by the vaccination of the mice with ProtD 1/3 E7 alone and was greatly increased by the addition of the adjuvant SB62, QS21+3DMPL to the protein. The analysis of the concentrations of the different IgG subclass show that a mixed antibody response has been induced as the concentration of all types of IgG subclass analyzed (IgG1, IgG2a, and IgG2b) were increased in the serun of the mice that received the adjuvanted antigen, compared to the concentration observed in the serum of mice that received the antigen or the adjuvant alone. The predominant isotype found was IgG2b which represented more than 80% of the total of IgG), this isotype is generally said to be associated with the induction of a TH1 type immune response.

EXAMPLE XX
In vivo Tumour Protection Experiments

Mice were immunised 2 times at 14 days interval with either PBS, adjuvant of example 1, 5 µg of protD1/3 E7 His or 5 µg of protD1/3 E7 His in the adjuvant of example 1 intra foot pad in a volume of 100 µl (50 µl/foot pad).

Tumour Growth

Four weeks after the latest vaccination mice were challenged with 2X10e5 TC1 cells/mouse S.C. in the flank. TC1 cells growing in vitro culture, were trypsinised and washed two times in serum-free medium and injected. 5 mice used in each group were monitored twice a week for tumour growth.

Figure 30:
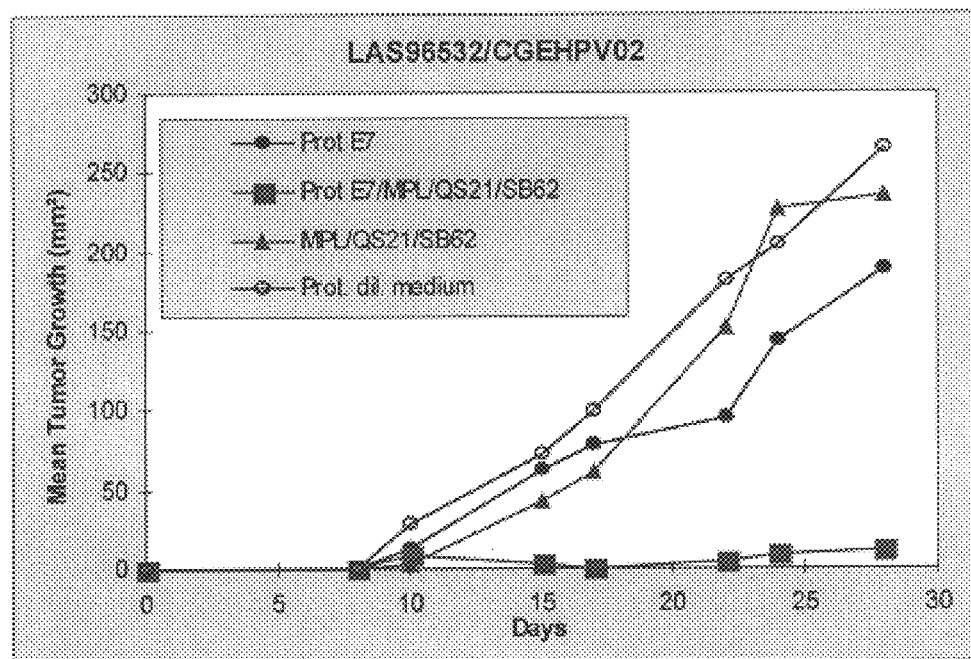
FIG. 30 graphically presents the protective effect of vaccination with Protein-D1/3-E7-His /HPV16 formulations against TC1 tumor challenge.

FIG. 30 shows that vaccination with the E7 protein in the SB62 QS21, 3D-MPL adjuvant protect the mice against the development of tumour (only one animal/5 has a very small and stable tumour) in all the other groups, that received the E7 protein without the adjuvant or the adjuvant alone developed growing tumours.

Immunological Read Out

Three weeks after the latest vaccination, before the tumour challenge 5 mice in each group were sacrificed for immunological read out.

Proliferation Assay

For in vitro assay, Lymphocytes were prepared as described above from the spleen and from the popliteal draining lymph nodes. An aliquot of 2×10e5 cells was plated in triplicate in 96 well plates with decreasing concentrations (10, 1, 0.1 µg/ml) of protD 1/3 E7 His coated or not onto latex microbeads (Sigma) to restimulate the cells in vitro (72 Hrs). T cell proliferation was measured by 3H thymidine incorporation.

Figure 31A:
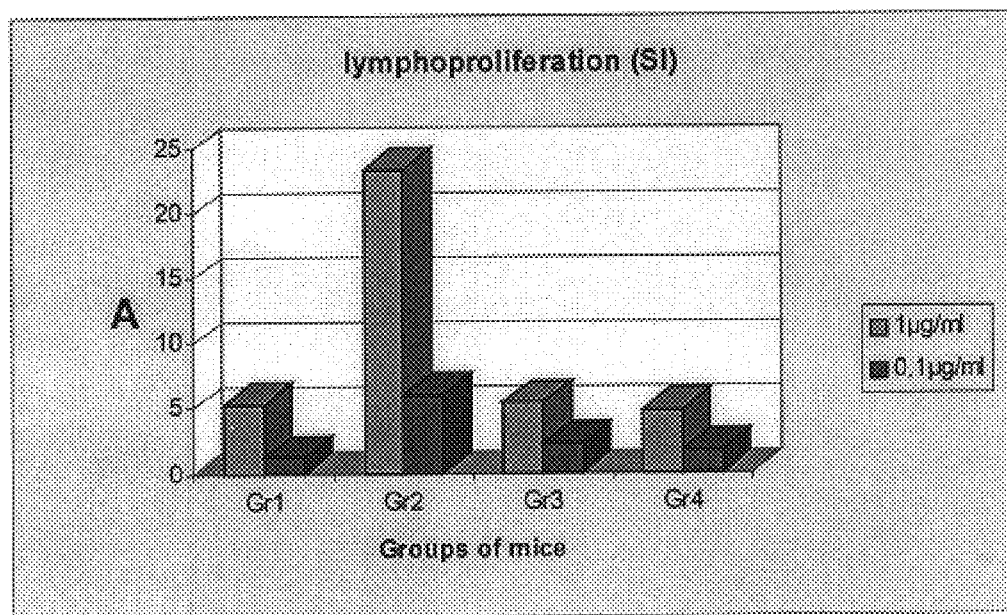
FIG. 31a presents data on lymphproliferation of splenocytes obtained from mice immunized with Protein-D1/3-E7-His /HPV16 formulations prior to tumor challenge, wherein the splenocytes were stimulated in vitro with soluble Protein-D1/3-E7-His /HPV16.
Figure 31B:
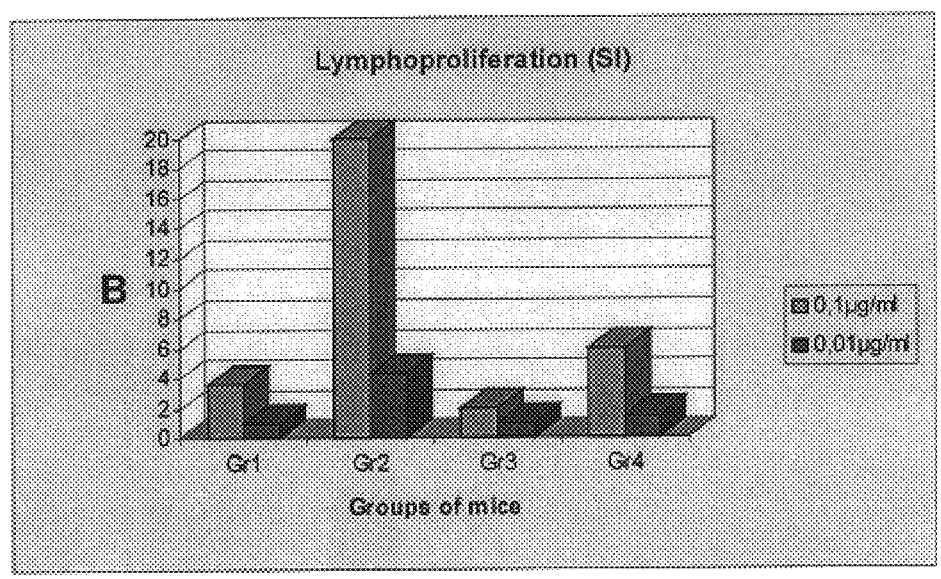
Figure 32:
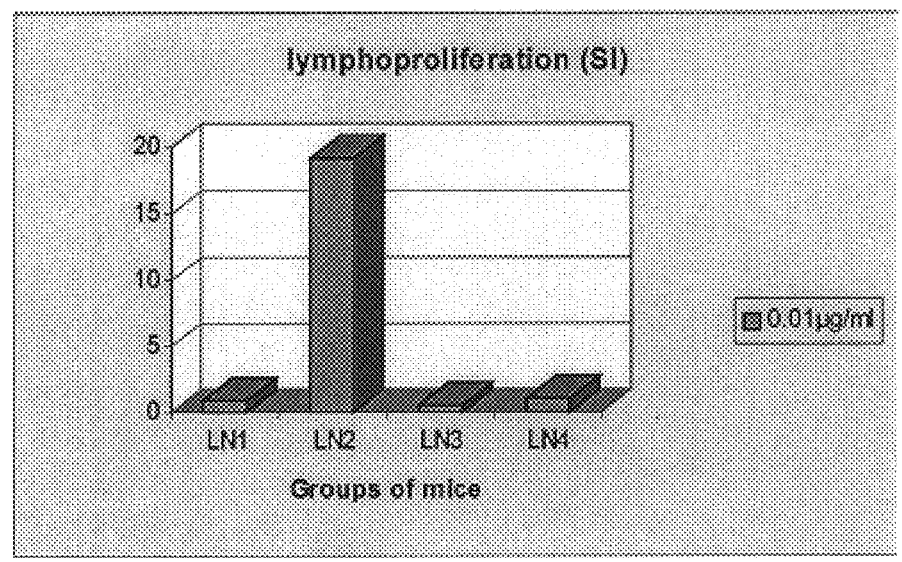
FIG. 32a presents data on lymphproliferation of lymph node cells obtained from mice immunized with Protein-D1/3-E7-His /HPV16 formulations prior to tumor challenge, wherein the lymph node cells were stimulated in vitro with soluble Protein-D1/3-E7-His /HPV16.
FIG. 32b presents data on lymphproliferation of lymph node cells obtained from mice immunized with Protein-D1/3-E7-His /HPV16 formulations prior to tumor challenge, wherein the lymph node cells were stimulated in vitro with latex microbeads coated with Protein-D1/3-E7-His /HPV16.
Figure 32B:
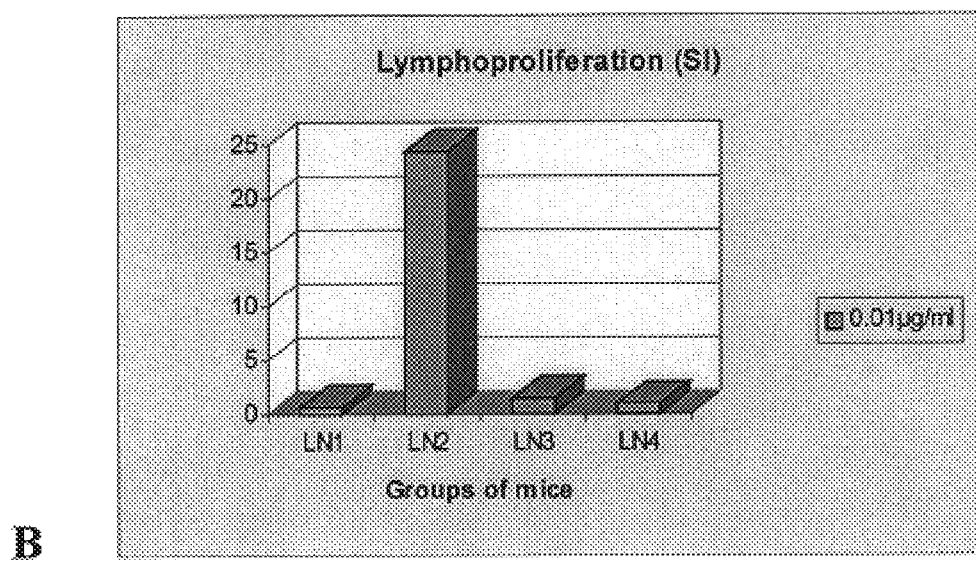
Figure 33A:
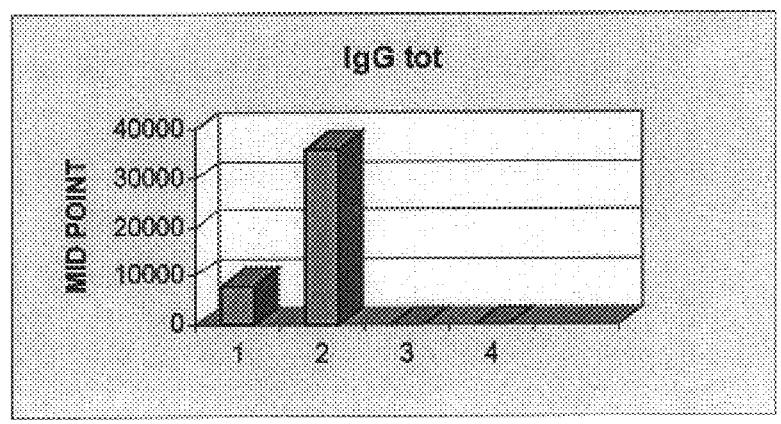
FIG. 33a presents the total IgG titer.
Figure 33B:
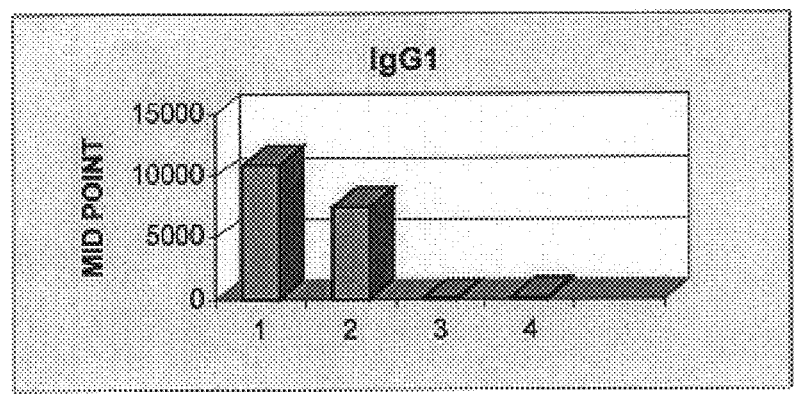
FIG. 33b presents the IgG1 titer.
Figure 33C:
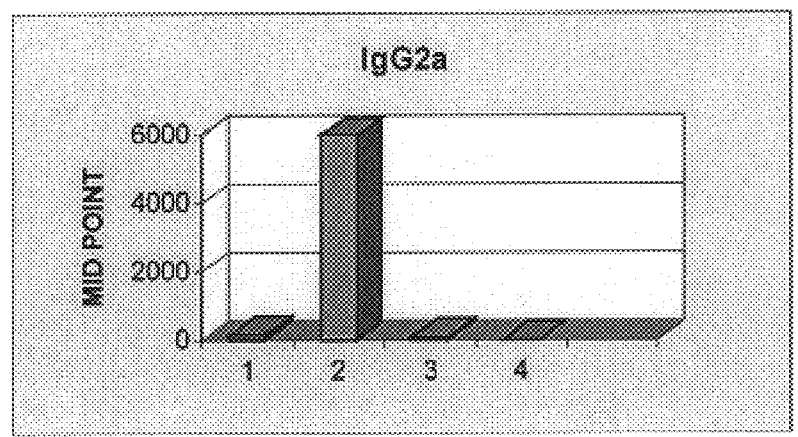
FIG. 33c presents the IgG2a titer.
Figure 33D:
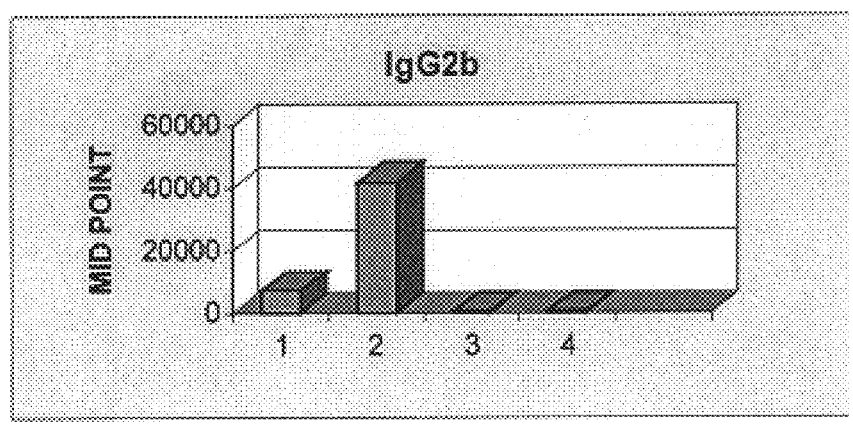
FIG. 33d presents the IgG2b titer.

FIGS. 31 and 32 show respectively that, both with splenocytes or popliteal lymph node cells, as it was observed in the therapeutic settings, a better lymphoproliferative activity was obtained for the mice that received the E7 protein in the SB62 QS21, 3D-MPL adjuvant antibody response.

FIG. 33 shows that as in the therapeutic settings, a better antibody response was observed in the serum of mice vaccinated with the ProtD1/3 E7 protein formulated in the 3D-MPL, QS21 O/W adjuvant. A mixed antibody response was triggered, as all the IgG subclass tested (IgG2a, IgG2b, IgG1), in this case also, IgG2b was the predominant isotype found, representing 75% of the total IgG.

EXAMPLE XXI
Vaccination Experiments with Prot D1/3 E7 (HPV 18)

Mice were vaccinated twice, 2 weeks apart, with 5 µg in 100 µl of protD 1/3 18 E7 His intra foot pad (50 µl/foot pad) in PBS or QS21, 3D-MPL and SB62, DQ MPL as described in WO96/33739 or DQ alum MPL as described in WO98/15827. Eight 6–8 weeks old Balb/c mice (Iffa Credo) were used in each group. 14 days post II, the spleen and lymph nodes were taken for immunological read out and blood sampling for serology.

Immunological Read Out

Proliferation Assay

For in vitro assay, lymphocytes were prepared by crushing the spleen or the popliteal lymph nodes from the vaccinated mice at day 28

An aliquot of 2×10e5 cells was plated in triplicate in 96 well plates with decreasing concentrations (10, 1, 0.1, 0.01 µg/ml) of protD 1/3 18 E7 His to restimulate the cells in vitro (72 Hrs). T cell proliferation was measured by 3H thymidine incorporation. The results are expressed as stimulation index (cpm sample/cpm baseline)

Figure 34:
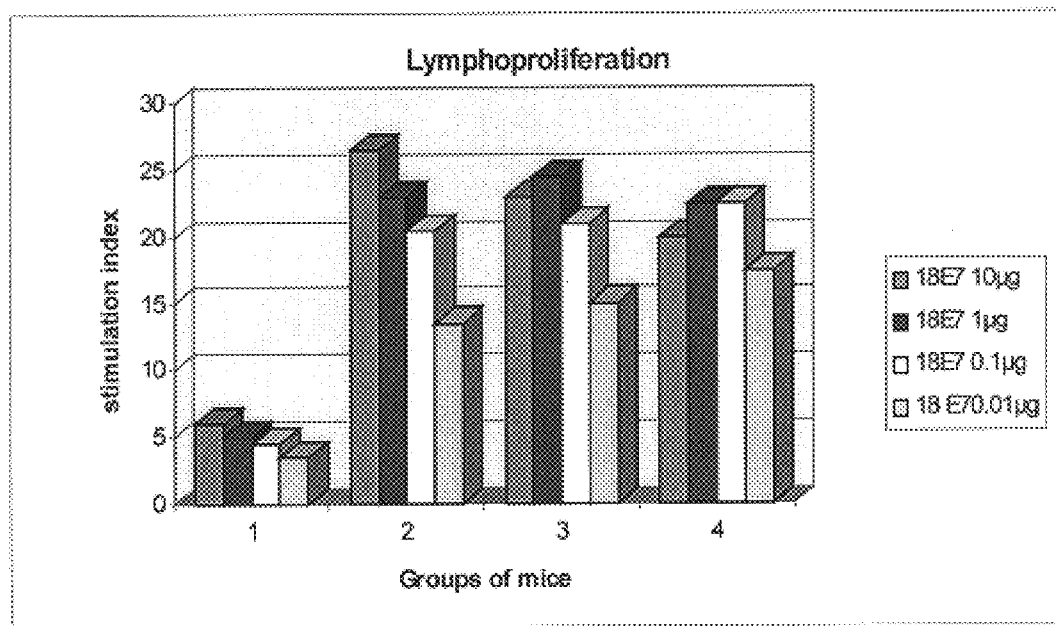
FIG. 34 presents data on lymphproliferation of splenocytes obtained from mice immunized with Protein-D1/3-E7-His /HPV18 formulations.
Figure 35:
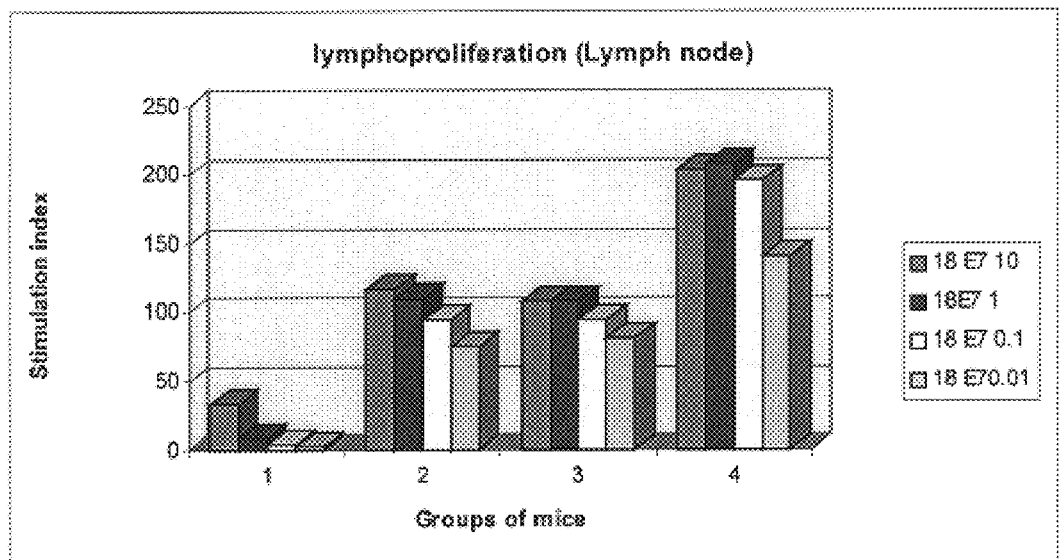
FIG. 35 presents data on lymphproliferation of lymph node cells obtained from mice immunized with Protein-D1/3-E7-His /HPV18.

FIGS. 34 and 35 compares the ability of protD 1/3 18 E7 to stimulate the proliferation of splenocytes or lymph node cells primed in vivo either by ProtD1/3 18 E7 His or Prot D1/3 18 E7 His+adjuvant and shows that only a basal lymphoproliferation is seen in mice that received the protein alone, on the contrary, high proliferative responses in spleen and very high responses in lymph nodes were detected in mice immunised with protD1/3 18 E7 His in adjuvant.

Cytokine Production

The cytokines (IL-5 and IFNg) produced in the culture supernatant after a 96 Hrs period of in vitro re-stimulation of spleen or lymph node cells, with medium or with the ProtD1/3 18E7 (1 or 3 µg/ml) was measured by ELISA as described:

IFNG (Genzyme)

Quantitation of IFNγ was performed by Elisa using reagents from Genzyme. Samples and antibody solutions were used at 50 µl per well. 96-well microtiter plates (Maxisorb Immnuno-plate, Nunc, Denmark) were coated overnight at 4° C. with 50 µl of hamster anti-mouse IFNg diluted at 1.5 µg/ml in carbonate buffer pH 9.5. Plates were then incubated for 1 hr at 37° C. with 100 µl of PBS containing 1% bovine serum albumin and 0.1% Tween 20 (saturation buffer). Two-fold dilutions of supernatant from in vitro stimulation (starting at ½) in saturation buffer were added to the anti-IFNg-coated plates and incubated for 1 hr 30 at 37° C. The plates were washed 4 times with PBS Tween 0.1% (wash buffer) and biotin-conjugated goat anti-mouse IFNg diluted in saturation buffer at a final concentration of 0.5 µg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 µl of TMB (Biorad) for 15 min. The reaction was stopped with $H_2SO_4$ 0.4N and read at 450 nm. Concentrations were calculated using a standard curve (mouse IFNγ standard) by SoftmaxPro (four parameters equation) and expressed in pg/ml.

IL5 (Pharmingen)

Quantitation of IL5 was performed by Elisa using reagents from Pharmingen. Samples and antibody solutions were used at 50 µl per well. 96-well microtiter plates (Maxisorb Immuno-plate, Nunc, Denmark) were coated overnight at 4° C. with 50 µl of rat anti-mouse IL5 diluted at 1 µg/ml in carbonate buffer pH 9.5. Plates were then incubated for 1 hr at 37° C. with 100 µl PBS containing 1% bovine serum albumin and 0.1% Tween 20 (saturation buffer). Two-fold dilutions of supernatant from in vitro stimulation (starting at ½) in saturation buffer were added to the anti-IFNg-coated plates and incubated for 1 hr 30 at 37° C. The plates were washed 4 times with PBS Tween 0.1% (wash buffer) and biotin conjugated rat anti-mouse IL5 diluted in saturation buffer at a final concentration of 1 µg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 µl of TMB (Biorad) for 15 min. The reaction was stopped with $H_2SO_4$ 0.4N and read at 450 nm. Concentrations were calculated using a standard curve (recombinant mouse IL5) by SoftmaxPro (four parameters equation) and expressed in pg/ml.

Starting with spleen cells, no IL-5 could be detected whatever the group tested, on the contrary, a very high production of IFNg production was observed in all groups, with only a slight increase in the group of mice that received the SBAS1c adjuvanted protein compared to the other groups. This suggest the induction of a TH1 type of immune response.

Regarding lymph node cells, a very weak IFNg production was obtained in the group of mice that received the protein alone and a 5–10 fold increase is observed with the adjuvanted protein. IL5 could only be detected in the group of mice receiving the SBAS2 adjuvanted protein.

Figure 36A:
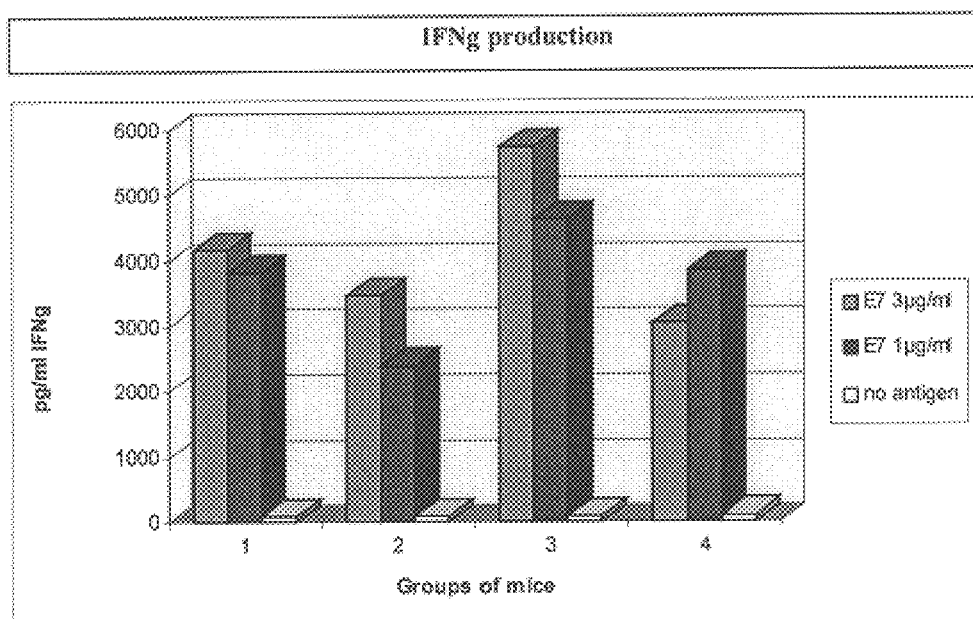
FIG. 36a presents data on production of IFNγ by splenocytes obtained from mice immunized with Protein-D1/3-E7-
Figure 36B:
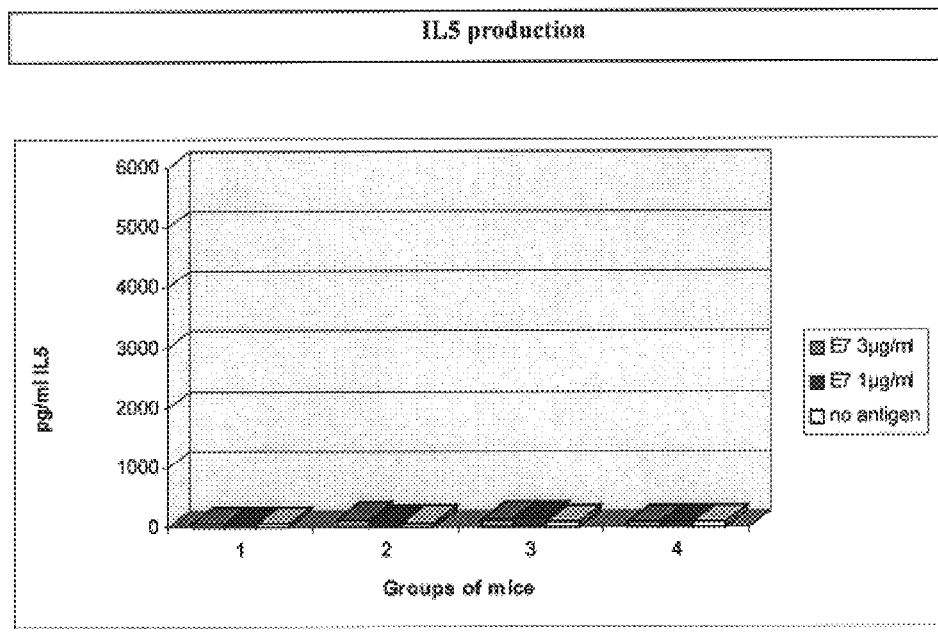
FIG. 36b presents data on production of IL-5 by splenocytes obtained from mice immunized with Protein-D1/3-E7-His HPV18 formulations.
Figure 37A:
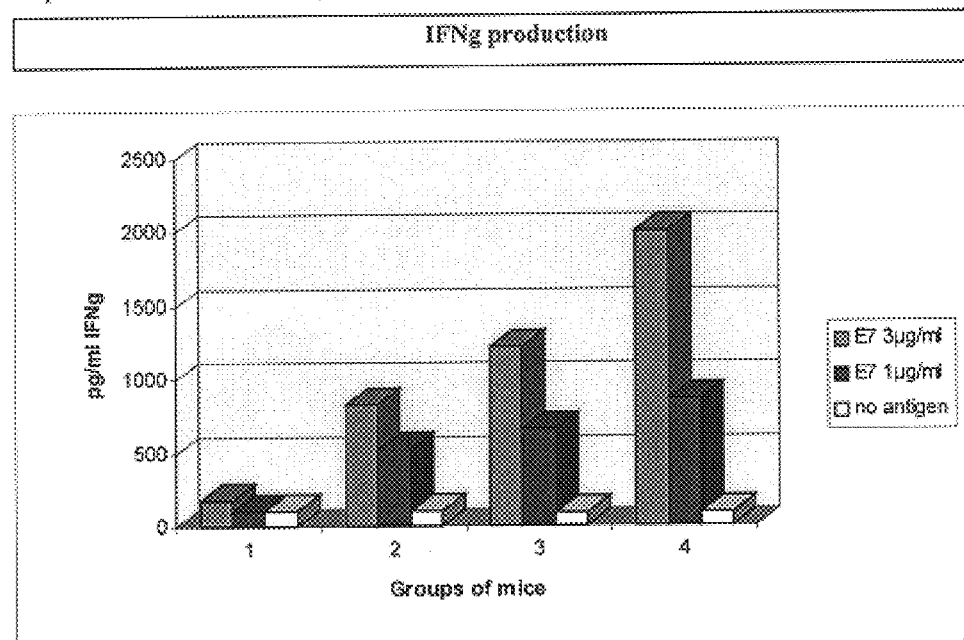
FIG. 37a presents data on production of IFNγ by lymph node cells obtained from mice immunized with Protein-D1/3-E7-His /HPV18 formulations.
Figure 37B:
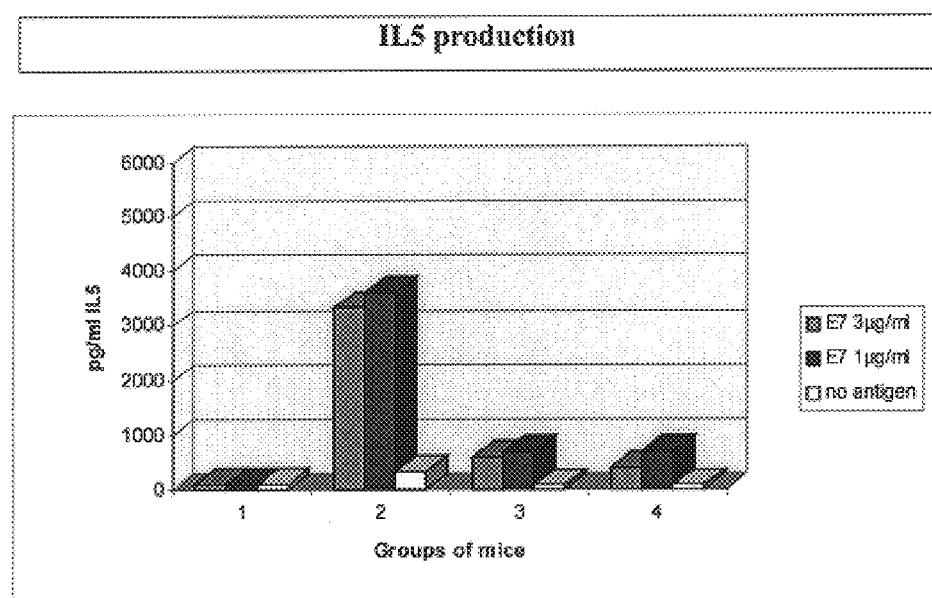
FIG. 37b presents data on production of IL-5 by lymph node cells obtained from mice immunized with Protein-D1/3-E7-His /HPV18 formulations.

FIGS. 36 and 37 compares the ability of ProtD1/3 18 E7 His to stimulate the production of cytokines 'IFNg and IL5) after in vitro re-stimulation of spleen or lymph node cells respectively.

Antibody response

Individual serum were taken at the same time as the organs and submitted to indirect ELISAs.

2.5 µg/ml of purified of protD1/3 18E7 protein HPV18 was used as coated antigen. After saturation in PBS+1% newborn calf serum 1 Hr at 37° C., the sera were serially diluted (starting at 1/100) in the saturation buffer and incubated O/N at 4° C. or 90 min at 37° C. After washing in PBS Tween 20 0.1%, biotinylated goat Anti mouse Ig (1/1000) or goat anti mouse Ig subclass (total IgG, IgG1, IgG2a, IgG2b) antisera (1/5000) were used as second antibodies, after an incubation of 90 min at 37° C., streptavidin coupled to peroxydase was added and TMB (tetra-methyl-benzidine/peroxide) was used as substrate, after 10 min. the reaction was stopped with H2SO4 0.5 M and the O.D.450 was determined.

A very weak antibody response is triggered with 2 injections of ProtD 1/3 18 E7 alone. The total IgG level was greatly increased by the addition of adjuvants to the protein vaccine.

The analysis of the concentrations of the different IgG subclass show that when the protein was injected in the presence of adjuvants, DQS21 3D-MPL or SB62, QS21/3D-MPL, a slight increase of the IgG2a subtype percentage was obtained: 28% IgG1, 48% IgG2a and 43% IgG1, 44% IgG2a respectively, compared to 46% of IgG1, 32% of IgG2a with the non adjuvanted protein. The strongest antibody response is obtained with the protein formulated in DQ alum with a clear shift in the isotype concentration (80% IgG1, 8% IgG2a). As the IgG2a isotype in Balb/c mice is generally considered to be associated with the induction of a TH1 type of immune. response, these results suggested that the DQS21, 3D-MPL and SB62 QS21/3D-MPL adjuvants tend to increase the TH1 type profile of the humoral response while SBAS5 induce a clear TH2 type of response.

Figure 38A:
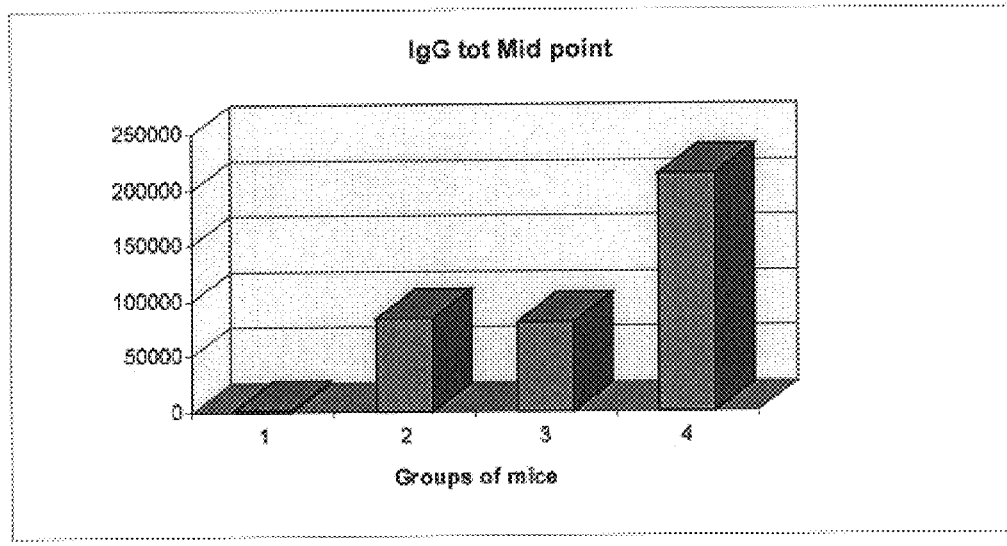
FIG. 38a presents the total IgG titer.
Figure 38B:
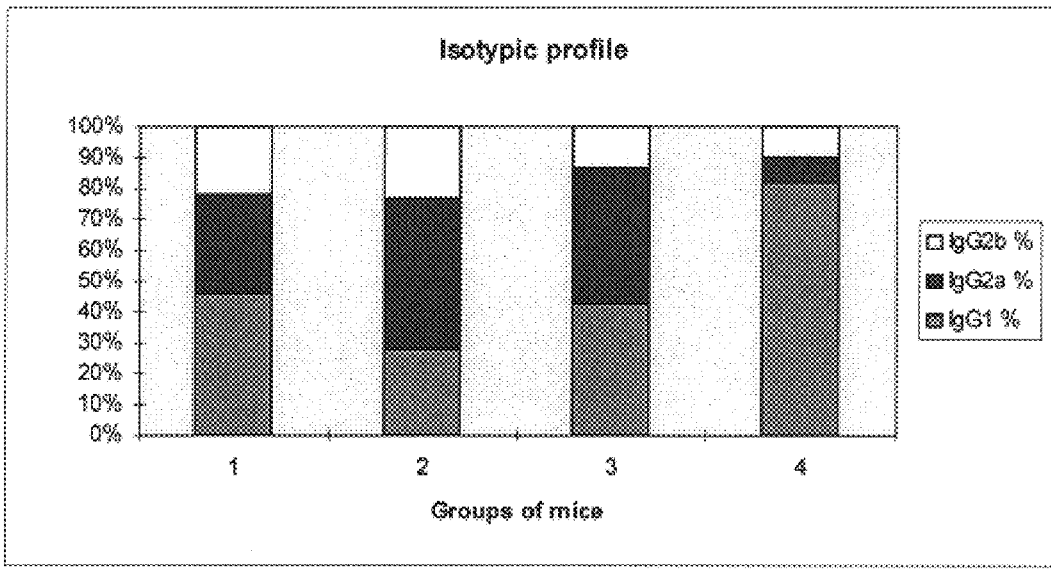
FIG. 38b presents the isotypic profile.

FIG. 38. The comparison of the midpoint dilution of the serum and relative percentage of the different isotypes elicited by the vaccinations in the different groups of mice are shown.

Conclusion

We have demonstrated that the fused protein: 1/3 Prot D and early protein E7 of HPV 16 induced a potent systemic antitumour immunity and the fusion protein ProtD1/3 and E7 of HPV18 has also been showed to be immunogenic in mice Vaccination with the prot D1/3 E7 HPV6 fusion protein protected the mice from a tumour challenge with E7 expressing tumour cells and eliminated small pre-established tumours expressing the E7 of HPV16 injected at a distant site from the vaccination site.

We have demonstrated that the ProtD1/3 E7 HPV16 protein in adjuvant is capable of enhancing helper T cell proliferation suggesting that the antitumour immune response induced by this vaccine is at least in part associated with a CD4+T cell response.

We have also demonstrated that a better antibody response was triggered by the vaccination with the ProtD1/3 E7 in the presence of the 3D-MPL containing adjuvant. The predominant isotype found in the serum of C57BL/6 mice being IgG2b suggesting that a TH1 type immune response was raised.

What is claimed is:

1. A fusion protein comprising Human papilloma virus antigen selected from the group consisting of fusion proteins E6, E7 and E6E7, linked to protein D or derivative therof from Haemophilius influenzae B, wherein the derivative thereof comprises approximately the first N-terminal 100 amino acids of protein D.

2. A protein as claimed in claim 1 wherein the E6 or E7 proteins are derived from HPV16 or HPV18.

3. A protein as claimed in claim 1 wherein the E7 proteins are mutated to reduce the binding for the retinoblastoma gene product.

4. The protein of claim 3 wherein the mutated HPV 16 E7 protein comprises a member selected from the group consisting of (i) replacement of $Cys_{24}$ with Glycine, (ii) replacement of Glutamic $acid_{26}$ with Glutamine, and (iii) replacement of $Cys_{24}$ with Glycine and Glutamic $acid_{26}$ with Glutamine.

5. The protein of claim 3 wherein the mutated HPV 18 E7 protein comprises a member selected from the group consisting of (i) replacement of $Cys_{27}$ with Glycine, (ii) replacement of Glutamic $acid_{29}$ with Glutamine, and (iii) replacement of $Cys_{27}$ with Glycine and Glutamic $acid_{29}$ with Glutamine.

6. A protein as claimed in claim 1 wherein a mutation is introduced into the E6 protein wherein inactivation of the p53 tumor suppressor protein by E6 is eliminated.

7. A protein as claimed in claim 1 additionally comprising a histidine tag of at least 4 histidine residues.

8. The fusion protein of claim 1 wherein the derivative thereof comprises approximately the first ⅓ of protein D.

9. The fusion protein of claim 1 wherein the derivative therof comprises amino acid residues 4-111 SEQ ID NO:1.

10. The fusion protein of claim 1 wherein the protein D or derivative thereof is lipidated.

11. A vaccine containing a protein as claimed in claim 1 and a pharmaceutically acceptable diluent or excipient.

12. A vaccine as claimed in claim 11 additionally comprising an adjuvant.

13. A vaccine as claimed in claim 12 wherein the protein is presented in an oil in water emulsion vehicle.

14. A vaccine as claimed in claim 13 comprising an additional HPV antigen.

15. The vaccine of claim 14 wherein the additional HPV antigen is one or more members selected from the group consisting of E2, E5, L1 and L2.

16. The vaccine of claim 15 wherein L1 and L2 are presented together as a virus like particle or wherein L1 alone is presented as a visus like particle or capsomere structure.

17. A vaccine as claimed in claim 12 wherein the adjuvant comprises 3D-MPL or QS21 or both.

18. A vaccine as claimed in claim 17 comprising an additional HPV antigen.

19. The vaccine of claim 18 wherein the additional HPV antigen is one or more members selected from the group consisting of E2, E5, L1 and L2.

20. The vaccine of claim 19 wherein L1 and L2 are presented together as a virus like particle or wherein L1 alone is presented as a virus like particle or capsomere structure.

21. A vaccine as claimed in claim 12 comprising an additional HPV antigen.

22. The vaccine of claim 21 wherein the additional HPV antigen is one or more members selected from the group consisting of E2, E5, L1 and L2.

23. The vaccine of claim 22 wherein L1 and L2 are presented together as a virus like particle or wherein L1 alone is presented as a virus like particle or capsomere structure.

24. A vaccine as claimed in claim 11 wherein the protein is presented in an oil in water emulsion vehicle.

25. A vaccine as claimed in claim 24 wherein the adjuvant comprises 3D-MPL or QS21 or both.

26. A vaccine as claimed in claim 25 comprising an additional HPV antigen.

27. The vaccine of claim 26 wherein the additional HPV antigen is one or more members selected from the group consisting of E2, E5, L1 and L2.

28. The vaccine of claim 27 wherein L1 and L2 are presented together as a virus like particle or wherein L1 alone is presented as a virus like particle or capsomere structure.

29. A vaccine as claimed in claim 24 comprising an additional HPV antigen.

30. The vaccine of claim 29 wherein the additional HPV antigen is one or more members selected from the group consisting of E2, E5, L1 and L2.

31. The vaccine of claim 30 wherein L1 and L2 are presented together as a virus like particle or wherein L1 alone is presented as a virus like particle or capsomere structure.

32. A vaccine as claimed in claim 11 comprising an additional HPV antigen.

33. The vaccine of claim 32 wherein the additional HPV antigen is one or more members selected from the group consisting of E2, E5, L1 and L2.

34. The vaccine of claim 33 wherein L1 and L2 are presented together as a virus like particle or wherein L1 alone is presented as a virus like particle or capsomere structure.

35. A process for the production of a vaccine as claimed in any of claims 11–34 to 28, comprising admixing the protein with a suitable adjuvant, diluent or other pharmaceutically acceptable excipient.

36. A method of treating a mammal suffering from HPV induced tumour lesions (benign or malignant), comprising administering a therapeutically effective amount of the vaccine of any of claims 11 to 26 and 33 to 28.

37. A DNA sequence encoding a protein as claimed in claim 1.

38. A vector containing a DNA sequence of claim 37.

39. A host transformed with a DNA sequence of claim 37.

40. A host as claimed in claim 39 additionally transformed with a DNA sequence encoding thioredoxin allowing co-expression of the fusion protein with thioredoxin in trans.

41. A vector containing a DNA sequence as claimed in claim 37 and a DNA sequence encoding thioredoxin allowing co-expression of the fusion protein with thioredoxin in trans.

42. A host transformed with a vector of claim 38 or 41.

43. A process for the production of a protein as claimed in any of claims 1 to 6 comprising transforming a host cell with a DNA sequence encoding the protein, expressing said sequence and isolating the desired product.

* * * * *